(12) United States Patent
Salvino et al.

(10) Patent No.: US 6,392,010 B1
(45) Date of Patent: May 21, 2002

(54) PROCESS FOR THE SOLID PHASE SYNTHESIS OF ALDEHYDE, KETONE, OXIME, AMINE, HYDROXAMIC ACID AND αβ-UNSATURATED CARBOXYLIC ACID AND ALDEHYDE COMPOUNDS

(75) Inventors: Joseph M. Salvino, Schwenksville; George C. Morton, Collegeville, both of PA (US); Helen J. Mason, Skillman, NJ (US); Richard F. Labaudiniere, Collegeville, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/469,829

(22) Filed: Dec. 22, 1999

Related U.S. Application Data

(63) Continuation-in-part of application No. PCT/US99/14251, filed on Jun. 23, 1999, which is a continuation-in-part of application No. 09/103,872, filed on Jun. 24, 1998, now Pat. No. 6,133,409, which is a continuation-in-part of application No. PCT/US97/23920, filed on Dec. 17, 1997, which is a continuation-in-part of application No. 08/928,943, filed on Sep. 12, 1997, now Pat. No. 6,057,369, which is a continuation of application No. PCT/US97/00264, filed on Jan. 2, 1997

(60) Provisional application No. 60/032,453, filed on Dec. 19, 1996, and provisional application No. 60/033,881, filed on Dec. 24, 1996.

(51) Int. Cl.$^7$ .................................................. C08J 3/00
(52) U.S. Cl. ....................... 528/486; 528/492; 528/493; 528/494; 528/495; 528/497; 528/498
(58) Field of Search .......................... 534/346; 528/486, 528/492, 493, 494, 495, 497, 498

(56) References Cited

FOREIGN PATENT DOCUMENTS

| | | |
|---|---|---|
| EP | 0 921 120 | 6/1999 |
| WO | WO 95/18623 | 7/1995 |
| WO | WO 96/26223 | 8/1996 |
| WO | WO97/24117 | 7/1997 |
| WO | WO98/05629 | 2/1998 |
| WO | WO98/18754 | 5/1998 |
| WO | WO98/29376 | 7/1998 |
| WO | WO99/41216 | 8/1999 |
| WO | WO99/57097 | 11/1999 |

OTHER PUBLICATIONS

U.S. Ser. No. 08/928943(456057369), filed Sep. 12, 1997.
Richter et al., A TFA–Cleavable Linking for Solid–Phase Synthesis of Hydroxamic Acids, Tetrahedron Letters, vol. 38, No. 3, pp.321–322, 1997.
Wipf et al., Solid–Phase Synthesis of Peptide Mimetics with (E) –Alkene Amide Bond Replacements Derived from Alkenylaziridines, J. Org. Chem, 1997, 62, 1586–1587.
Fehrentz et al., Improved Solid Phase Synthesis of C–terminal Peptide Aldehydes, Tetrahedron Letters, vol. 36, No. 43, pp. 7871–7874, 1995.
Johnson et al., Solid Phase Synthesis of Alkenes Using The Horner–Wadsworth–Emmons Reaction and Monitoring by Gel Phase 31P NMR, Tetrahedron Letters, vol. 36, No. 51, pp. 9253–9256, 1995.
Dinh et al., Synthesis of Ketones and Aldehydes via Reactions of Weinreb–Type Amides on Solid Support, Tetrahedron Letters, vol. 37, No. 8, pp. 1161–1164, 1996.
Prasad et al., Solid–Phase Reagents for the Isolation and Protection of Carbonyl Compounds, J. Steroid Biochem, vol. 18, No. 3, pp. 257–261, 1983.
Salvino et al., Automated Parallel Synthesis of Olefins, ISLAR '97 Proceedings, pp. 99–106.

*Primary Examiner*—Brian J. Davis
(74) *Attorney, Agent, or Firm*—George G. Wang; Irving Newman

(57) ABSTRACT

This invention is directed to a process for the solid phase synthesis of aldehyde, ketone, oxime, amine, hydroxamic acid and α,β-unsaturated carboxylic acid and aldehyde compounds and to polymeric hydroxylamine resin compounds useful therefor.

6 Claims, No Drawings

PROCESS FOR THE SOLID PHASE SYNTHESIS OF ALDEHYDE, KETONE, OXIME, AMINE, HYDROXAMIC ACID AND α,β-UNSATURATED CARBOXYLIC ACID AND ALDEHYDE COMPOUNDS

CROSS REFERENCE TO RELATED APPLICATIONS

This application is a continuation-in-part of International Patent Application No. PCT/US99/14251, filed Jun. 23, 1999, which is a continuation-in-part of U.S. patent application Ser. No. 09/103,872, filed Jun. 24, 1998 now U.S. Pat. No. 6,133,409, which application is a continuation-in-part of International Patent Application No. PCT/US97/23920, filed Dec. 17, 1997, which claims benefit of U.S. patent application Ser. No. 60/032,453, filed Dec. 19, 1996, and U.S. patent application Ser. No. 60/033,881, filed Dec. 24, 1996; and a continuation in part of U.S. patent application Ser. No. 08/928,943, filed Sep. 12, 1997 now U.S. Pat. No. 6,057,369, which in turn is a continuation of International Patent Application No.PCT/US97/00264, filed Jan. 2, 1997.

FIELD OF THE INVENTION

This invention is directed to processes for the solid-phase synthesis of aldehyde, ketone, oxime, amine, and hydroxamic acid and α,β-unsaturated carboxylic acid and aldehyde compounds and to polymeric hydroxylamine resin compounds useful therefor.

BACKGROUND OF THE INVENTION

Solid-phase synthetic techniques, in which a reagent is immobilized on a polymeric material which is inert to the reagents and reaction conditions employed, as well as being insoluble in the media used, are important synthetic tools for preparing amides, peptides and hydroxamic acids. For solid phase peptide synthesis, a summary of the many techniques may be found in J. M. Stewart and J. D. Young, *Solid Phase Peptide Synthesis*, 2nd. Ed., Pierce Chemical Co. (Chicago, Ill., 1984); J. Meienhofer, *Hormonal Proteins and Peptides*, vol. 2, p. 46, Academic Press (New York), 1973; and E. Atherton and R. C. Sheppard, *Solid Phase Peptide Synthesis: A Practical Approach*, IRL Press at Oxford University Press (Oxford, 1989). For the use of solid phase methodology in the preparation of non-peptide molecules see Leznoff, C. C., *Acc. Chem. Res.*, 11, 327–333 (1978).

A number of polymeric reagents have found synthetic use in simple functional group transformations. See A. Akelah and D. C. Sherrington, Application of Functionalized Polymers in Organic Synthesis, *Chem Rev.*, 81, 557–587 (1981) and W. T. Ford and E. C. Blossey, *Polymer Supported Reagents, Polymer supported Catalysts, and Polymer Supported Coupling Reactions*, in *Preparative Chemistry using Supported Reagents*, Pierre Laszlo, ed., Academic Press, Inc., 193–212 (1987). For the use of polymeric reagents in oxidation reactions see J. M. J. Frechet et al., *J. Org. Chem.*, 43, 2618 (1978) and G. Cainelli et al., *J. Am. Chem. Soc.*, 98, 6737 (1976). For the use of polymeric reagents in halogenation reactions see J. M. J. Frechet et al., *J. Macromol. Sci. Chem.*, A-11, 507 (1977) and D. C. Sherrington et al., *Eur. Polym. J.*, 13, 73, (1977). For the use of polymeric reagents in epoxidation reactions see J. M. J. Frechet et al., *Macromolecules*, 8, 130 (1975) and C. R. Harrison et al., *J. Chem. Soc. Chem. Commun.*, 1009 (1974). For the use of polymeric reagents in acylation reactions see M. B. Shambhu et al., *Tet. Lett.*, 1627 (1973) and M. B. Shambhu et al., *J. Chem. Soc. Chem. Commun.*, 619 (1974). For the use of polymeric reagents in Wittig reactions see S. V. McKinley et al., *J. Chem. Soc. Chem. Commun.*, 134 (1972).

Polymeric reagents also have found widespread use in combinatorial synthesis and for preparing combinatorial libraries. See F. Balkenhohl et al., *Angew. Chem. Int. Ed. Engl.*, 35, 2288–2337 (1996) and L. A. Thompson et al., *Chem Rev.*, 96, 555–600 (1996).

A polymeric reagent has the advantage of ease of separation from low molecular weight reactants or products by filtration or selective precipitation. The polymeric reagent also can be used in excess to effect fast and quantitative reactions, such as in the case of acylations, or a large excess of reactants may be used to drive the equilibrium of the reaction towards product formation to provide essentially quantitative conversion to product, as in solid phase peptide synthesis. A further advantage of supported reagents and catalysts is the fact that they are recyclable and that they lend easily to automated processes. In addition, supported analogs of toxic and odorous reagents are safer to use.

PCT application publication no. WO96/26223 discloses the synthesis of hydroxamic acid compounds using a solid phase hydroxylamine substrate.

Prasad et al. disclose a O-methylhydroxylamine-polystyrene resin compound in J. Steroid Biochem., 18, 257–261 (1983).

Resin-bound Weinreb-like amides are disclosed by Fehrentz et al., *Tet. Lett.*, 1995, 36, 7871–7874 and Dinh et al., *Tet. Lett.*, 1996, 37, 1161–1164.

Polymeric Horner-Wadsworth-Emmons reagents are disclosed by Wipf et al., *J. Org. Chem.*, 1997, 62, 1586 and Johnson et al., *Tetrahedron Lett.*, 1995, 36, 9253.

SUMMARY OF THE INVENTION

This invention is directed to a process for the preparation of a ketone compound of formula

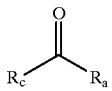

wherein $R_c$ and $R_a$ are independently aliphatic or aromatic, this process comprising (a) reacting an N-alkylated polymeric hydroxamic acid resin compound of formula

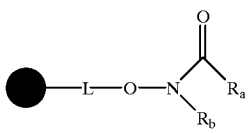

wherein

● is a solid support, L is absent or a linking group and $R_b$ is aliphatic or aryl with an organometallic reagent of formula $R_cM$ wherein $R_c$ is an aliphatic or aryl anion and M is a metal cation; and (b) liberating the ketone compound from the resin.

In another aspect, this invention is directed to a process for the preparation of an aldehyde compound of formula $R_aCHO$ wherein $R_a$ is defined above, comprising (a) reacting an N-alkylated polymeric hydroxamic acid resin compound of formula

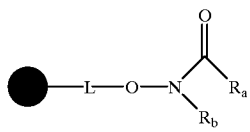

wherein

L and $R_a$ and $R_b$ are defined above;

with a reducing agent; and (b) liberating the aldehyde compound from the resin.

In another aspect, this invention is directed to a process for the preparation of an N-alkylated polymeric hydroxamic acid resin compound of formula

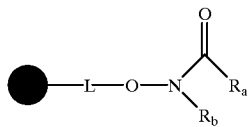

wherein

L and $R_a$ and $R_b$ are defined above, comprising (a) coupling a carboxylic acid compound of formula $R_aCO_2H$ with a polymeric hydroxylamine resin compound formula

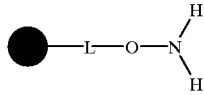

to form a polymeric hydroxamic acid resin compound of formula

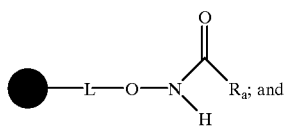

(b) reacting the polymeric hydroxamic acid resin compound with an alkylating agent of formula $R_bLG$ wherein LG is a leaving group.

In another aspect, this invention is directed to a process for the preparation of an N-alkylated polymeric hydroxamic acid resin compound of formula

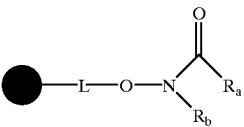

wherein

L and $R_a$ and $R_b$ are defined above, comprising (a) reacting an N-protected polymeric hydroxamic acid resin compound of formula

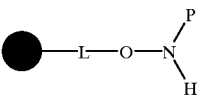

wherein P is an amine protecting group, with an alkylating agent of formula $R_bLG$ wherein LG is defined above, to form a polymeric N-protected N-alkylated hydroxylamine resin compound of formula

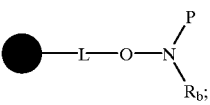

(b) removing the amine protecting group to form a polymeric N-alkylated hydroxylamine resin compound of formula

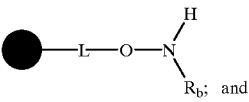

(c) coupling the polymeric N-alkylated hydroxylamine resin compound with a carboxylic acid compound of formula $R_aCO_2H$.

In another aspect, this invention is directed to a process for preparing a hydroxamic acid compound of formula

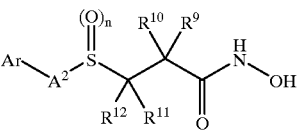

wherein $A^2$ is a direct bond, alkylene, or $NR^{13}$;

$R^{13}$ is hydrogen or alkyl;

$R^9$ is $-L^1-R^{14}$ or $-L^2-R^{15}$;

$L^1$ is a direct bond or alkylene;

$R^{14}$ is hydrogen, aryl, carboxy, cyano, cycloalkyl, cycloalkenyl, cyclocarbamoyl, cycloimidylalkyl, heterocyclyl, heteroaryl, $-NH-C(=O)-NH_2$, (N-carbamoyl)cyclic amine, $-C=N-O-C(=O)-NH_2$, $-C(=O)-NY^1Y^2$, $-NY^1SO_2aryl$, $-NHR^{13}$, $-SR^{13}$ or $-OR^{13}$;

$L^2$ is alkenylene or alkynylene;

$R^{15}$ is hydrogen, aryl, carboxy, cyano, cycloalkyl, cycloalkenyl, heterocyclylalkyl or heteroaryl;

$R^{10}$ and $R^{12}$ are independently hydrogen or alkyl; or $R^{10}$ and $R^{12}$ together form a bond, or $R^{10}$ and $R^9$ taken together with the carbon atom through which $R^{10}$ and $R^9$ are attached form spirocycloalkyl;

$R^{11}$ is a group —$L^3$—$R^{16}$, or $R^{11}$ and $R^9$ taken together with the carbon atoms through which $R^{11}$ and $R^9$ are attached form cycloalkylene; or $R^{11}$ and $R^{12}$ taken together with the carbon atom through which $R^{11}$ and $R^{12}$ are attached form spirocycloalkyl;

$L^3$ is a direct bond, alkylene, alkenylene or alkynylene;

$R^{16}$ is hydrogen, cycloalkyl, cycloalkenyl, heterocyclyl, heterocyclenyl, aryl, heteroaryl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, fused cycloalkenylaryl, fused cycloalkylaryl, fused heterocyclylaryl, fused heterocyclenylaryl, fused cycloalkylheteroaryl, fused cycloalkenylheteroaryl, fused heterocyclenylheteroaryl, fused heterocyclylheteroaryl, —NH—C(=O)—NH$_2$, —C=N—O—C(=O)—NH$_2$, —C(=O)—NY$^1$Y$^2$; —NY$^1$SO$_2$aryl, —NR$^{13}$, —SR$^{13}$, or —OR$^{13}$ $Y^1$ and $Y^2$ are independently selected from hydrogen, alkyl, aralkyl, and aryl, or $Y^1$ and $Y^2$ taken together with the nitrogen atom to which $Y^1$ and $Y^2$ are attached form azaheterocyclyl;

Ar is selected from the group of formulae

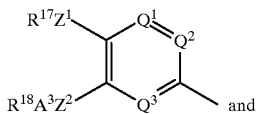

(i)

and

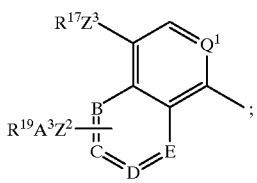

(ii)

$R^{17}$ is alkyl, or, when $Z^3$ is a direct bond, then $R^{17}$ is selected from hydrogen, alkyl, alkenyl and alkynyl;

$R^{18}$ is cycloalkyl, cycloalkenyl, heterocyclyl, heterocyclenyl, aryl, heteroaryl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, fused cycloalkenylaryl, fused cycloalkylaryl, fused heterocyclylaryl, fused heterocyclenylaryl, fused cycloalkylheteroaryl, fused cycloalkenylheteroaryl, fused heterocyclenylheteroaryl, fused cycloalkenylheteroaryl- heteroaryl or fused heterocyclylheteroaryl;

$R^{19}$ is $R^{20}$, —OR$^{20}$, —SR$^{20}$, —SOR$^{20}$, —SO$_2$R$^{20}$, —SO$_2$NR$^{20}$R$^{21}$, —NR$^{20}$SO$_2$R$^{21}$, —NR$^{20}$R$^{21}$, —O(C=O)NR$^{20}$R$^{21}$, —NR$^{20}$C(=O)R$^{21}$, —N(OH)C(=O)R$^{20}$, or —C(=O)N(OH)R$^{21}$, $R^{20}$ and $R^{21}$ are independently hydrogen, alkyl, alkenyl, cycloalkyl, cycloalkenyl, heterocyclyl, heterocyclenyl, aryl, heteroaryl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, fused cycloalkenylaryl, fused cycloalkylaryl, fused heterocyclylaryl, fused heterocyclenylaryl, fused cycloalkylheteroaryl, fused cycloalkenylheteroaryl, fused heterocyclenylheteroaryl, fused heterocyclylheteroaryl, aralkyl or heteroaralkyl; or $R^{20}$ and $R^{21}$ taken together with the nitrogen atom to which $R^{20}$ and $R^{21}$ are attached form azaheterocyclyl;

$A^3$ is a direct bond, alkylene, alkenylene or alkynylene;

$Z^1$ and $Z^3$ are independently a direct bond, oxygen, sulfur or NH;

$Z^2$ is a direct bond, oxygen or sulfur;

B, C, D, and E are independently CH or a heteroatom selected from O, S, N, NOR$^{22}$ and NR$^{22}$, or three of B, C, D and E are independently CH or a heteroatom selected from O, S, N or NR$^{22}$, and the other of B, C, D and E is a direct bond; and one of B, C, D and E that are in adjacent positions is other than O or S;

$R^{22}$ is hydrogen, alkyl, aryl, lower aralkyl, heteroaryl or lower heteroaralkyl $Q^1$, $Q^2$ and $Q^3$ independently are CH, CX$^1$ or N;

$X^1$ is halogen; and n is 0, 1 or 2; or a prodrug thereof, acid isostere thereof, pharmaceutically acceptable salt thereof, or solvate thereof, this process comprising treating a polymeric hydroxamic acid resin compound of formula

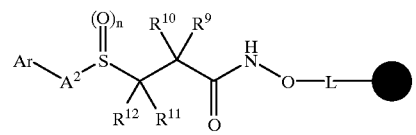

with acid.

In another aspect, this invention is directed to a process for the preparation of a polymeric oxime ether resin compound of formula

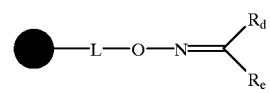

wherein

and L are as defined herein and $R_d$ and $R_e$ are independently H, aliphatic or aromatic, this process comprising reacting a polymeric hydroxylamine resin compound of formula

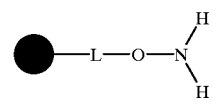

with a carbonyl compound of formula

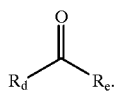

In another aspect, this invention is directed to a process for the preparation of an α-amine compound of formula

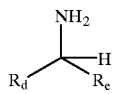

wherein $R_d$ and $R_e$ are independently H, aliphatic or aryl, provided that $R_d$ and $R_e$ are not both H, comprising reductively cleaving a polymeric oxime ether resin compound of formula

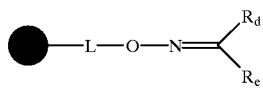

wherein

and L are as defined herein.

In another aspect, this invention is directed to a process for the preparation of a substituted α-amine compound of formula

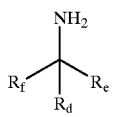

wherein $R_d$ and $R_e$ are independently H, aliphatic or aromatic, provided that $R_d$ and $R_e$ are not both H, and $R_f$ is aliphatic or aromatic, comprising (a) reacting a polymeric oxime ether compound of formula

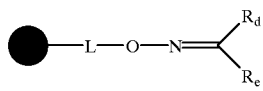

wherein

and L are as defined herein, with an organometallic reagent of formula $R_fM$ wherein $R_f$ is an aliphatic or aromatic anion and M is a metal cation, to form a polymeric α-substituted hydroxylamine resin compound of formula

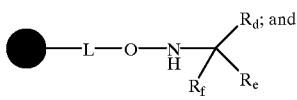

(b) reductively cleaving the α-substituted hydroxylamine resin compound.

In another aspect, this invention is directed to a process for the preparation of a lactone compound of formula

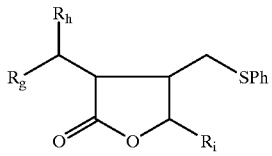

wherein $R_g$, $R_h$ and $R_i$ are independently aliphatic or aromatic and Ph is phenyl, comprising (a) treating an α,β-unsaturated polymeric hydroxamic acid ester resin compound of formula

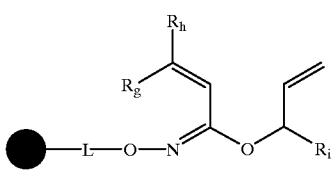

wherein

and L are as defined herein, with thiophenol and a free radical initiator to form a polymeric oximyl lactone compound of formula

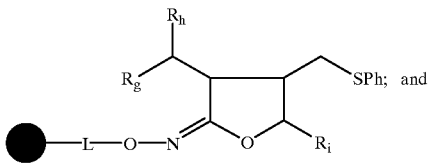

(b) treating the polymeric oximyl lactone compound with aqueous acid.

In another aspect, this invention is directed to a process for the preparation of an α,β-unsaturated polymeric hydroxamic acid ester resin compound of formula

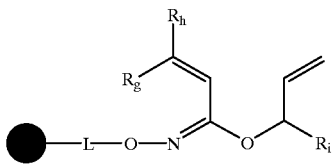

wherein

,

L and $R_g$ and $R_h$ and $R_i$ are as defined herein, comprising reacting a polymeric hydroxylamine resin compound of formula

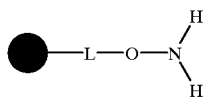

with an α,β-unsaturated carboxylic acid ester compound of formula

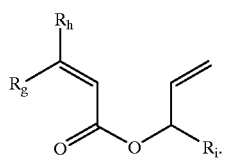

In another aspect, this invention is directed to a process for the preparation of an α-cyclic hydroxylamine compound of formula

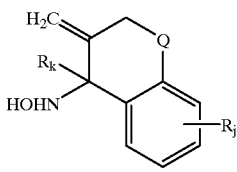

wherein $R_j$ and $R_k$ are aliphatic or aromatic and Q is —O— or —CH$_2$—, comprising (a) treating a polymeric acetophenone oxime compound of formula

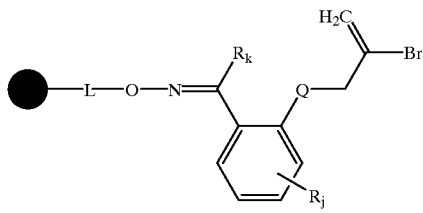

wherein

● and L are as defined herein, with trialkyltin hydride and a free radical initiator to form a polymeric α-cyclic hydroxylamine resin compound of formula

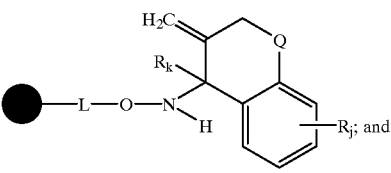

(b) treating the polymeric α-cyclic hydroxylamine resin compound with aqueous acid.

In another aspect, this invention is directed to a process for the preparation of an α-cyclic amino compound of formula

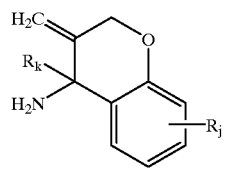

wherein $R_j$ and $R_k$ are aliphatic or aromatic and Q is —O— or —CH$_2$—, comprising reductively cleaving a polymeric α-cyclic hydroxylamine resin compound of formula

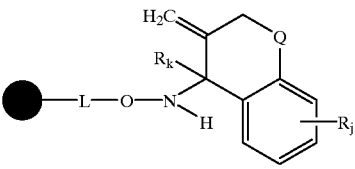

wherein

● and L are as defined herein.

In another aspect, this invention is directed to a process for the preparation of an α-cyclic hydroxylamine compound of formula

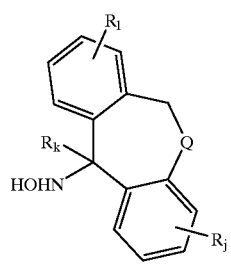

wherein $R_j$, $R_k$ and $R_l$ are aliphatic or aromatic and Q is —O— or —CH$_2$—, comprising (a) treating a polymeric acetophenone oxime compound of formula

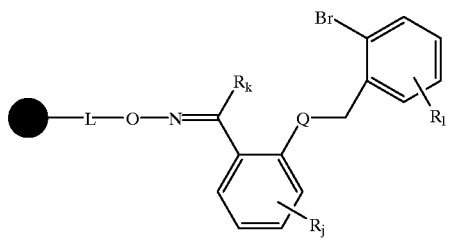

wherein

● and L are as defined herein, with trialkyltin hydride and a free radical initiator to form a polymeric α-cyclic hydroxylamine resin compound of formula

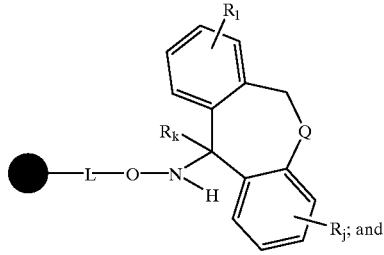

(b) treating the polymeric α-cyclic hydroxylamine resin compound with aqueous acid.

In another aspect, this invention is directed to a process for the preparation of an α-cyclic amino compound of formula

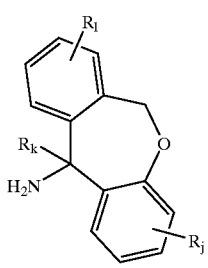

wherein $R_j$, $R_k$ and $R_l$ are aliphatic or aromatic and Q is —O— or —CH$_2$—, comprising reductively cleaving a polymeric α-cyclic hydroxylamine resin compound of formula

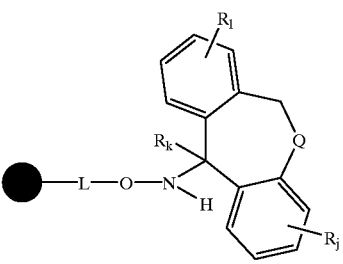

wherein

● and L are as defined herein.

In another aspect, this invention is directed to an N-protected hydroxylamine resin compound of formula

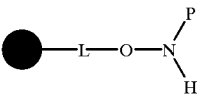

wherein

● and L are as defined herein and P is an amine protecting group, provided that P is other than 4-methoxybenzyl or 2,4-dimethoxybenzyl.

In another aspect, this invention is directed to a polymeric fluorophenyl hydroxylamine resin compound of formula

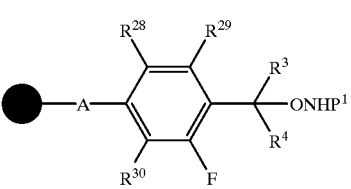

wherein

●,

A, $R^3$ and $R^4$ are as defined herein, $P^1$ is an amine protecting group, and $R^{28}$, $R^{29}$, and $R^{30}$ are ring system substituents, or $R^{28}$ and $R^{29}$ taken together with the carbon atoms through which they are linked form a 6 membered aryl or a 5 to 6 membered heteroaryl.

In another aspect, this invention is directed to a process for preparing an αα, unsaturated alkenoate resin compound of formula

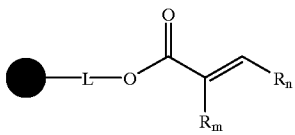

wherein

, and L are as defined herein; $R_m$ is H or aliphatic; and $R_n$ is aliphatic or aromatic, comprising (a) treating a mixture in a reaction vessel of a first solvent and a polymeric phosphonoacetoxy resin compound of formula

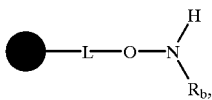

wherein $R_{20}$ and $R_{20}$ are alkyl, with excess base;

(b) draining the solvent from the reaction vessel; and
(c) adding a solution of an aldehyde of formula $R_nCHO$ in a less polar second solvent.

In another aspect, this invention relates to the N-alkylated polymeric hydroxamic acid resin compound of formula

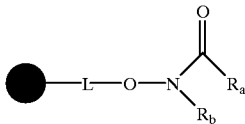

wherein

is a solid support containing one or more fluorine atoms.

In another aspect, this invention is directed to the use of the N-alkylated polymeric hydroxamic acid resin compound of formula

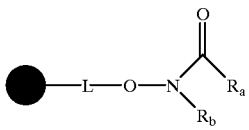

wherein

is a solid support containing one or more fluorine atoms, for the solid-phase synthesis of aldehyde, ketone, oxime, amine, and hydroxamic acid and α,β-unsaturated carboxylic acid and aldehyde compounds, wherein the solid support containing one or more fluorine atoms facilitates monitoring and quantifying the solid-phase reactions by $^{19}F$ NMR. A detailed discussion of the method of quantifying solid-phase reactions by $^{19}F$ NMR, and the synthesis of fluorinated resins is described in PCT/US98/26512 filed Dec. 14, 1998, the contents of which are incorporated herein by reference.

DETAILED DESCRIPTION OF THE INVENTION

Definitions of Terms

As used above, and throughout the description of the invention, the following terms, unless otherwise indicated, shall be understood to have the following meanings.

"Solid support" means a substrate which is inert to the reagents and reaction conditions described herein, as well as being substantially insoluble in the media used. Representative solid supports include inorganic substrates such as kieselguhr, silica gel, and controlled pore glass; organic polymers including polystyrene, including 1–2% copolystyrene divinyl benzene (gel form) and 20–40% copolystyrene divinyl benzene (macroporous form), polypropylene, polyethylene glycol, polyacrylamide, cellulose, and the like; and composite inorganic/polymeric compositions such as polyacrylamide supported within a matrix of kieselguhr particles. See J. M. Stewart and J. D. Young, *Solid Phase Peptide Synthesis*, 2 nd. Ed., Pierce Chemical Co. (Chicago, Ill., 1984). Solid support is designated generally as

throughout the description.

In addition, "solid support" includes a solid support as described above which is affixed to a second inert support such as the pins described in Technical Manual, Multipin™ SPOC, Chiron Technologies (1995) and references therein which comprise a detachable polyethylene- or polypropylene-based head grafted with an amino functionalized methacrylate copolymer and an inert stem.

In addition, "solid support" includes polymeric supports such as the polyethylene glycol supports described by Janda et al., *Proc. Natl. Acad. Sci. USA*, 92, 6419–6423 (1995) and S. Brenner, WO 95/16918, which are soluble in many solvents but can be precipitated by the addition of a precipitating solvent.

In addition "solid support" includes polymeric supports as described above, containing one or more fluorine atoms. Polymeric supports containing one or more fluorine atoms are prepared by polymerization using methods known in the art so as to incorporate one or more fluorine-containing monomers into the solid support. Representative suitable fluorine-containing monomers include 4-fluorostyrene, 4-trifluoromethylstyrene, 2-fluoro-4-vinylbenzyl chloride and the like. Polymeric supports containing one or more fluorine atoms are readily prepared, for example by copolymerizing mixtures of 4-fluorostyrene, styrene, 1,4-divinylbenzene and 4-vinylbenzyl chloride. A detailed discussion of the method of synthesizing fluorinated resins is described in PCT/US98/26512 filed Dec. 14, 1998, the contents of which are incorporated herein by reference. Solid supports containing one or more fluorine atoms may be designated as or

throughout the description.

"Polymeric hydroxylamine resin compound" means a solid support as defined above which is chemically modified as is known in the art to incorporate a plurality of hydroxylamine (—ONH$_2$) or protected hydroxylamine (—ONHP) groups. The hydroxylamine or protected hydroxylamine groups are covalently bound directly to the solid support or attached to the solid support by covalent bonds through a linking group. The polymeric hydroxylamine resin compounds according to the process aspect of this invention are designated herein as

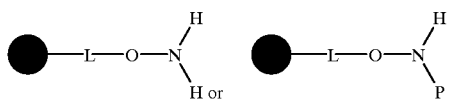

wherein

is a solid support as defined herein, L is absent or a linking group and P is an amine protecting group.

"Linking group" and "linker" mean a group through which the amino, aminomethyl or other functionality may be covalently linked to the solid support. The linking group is generally inert to the reagents and reaction conditions described herein.

"Amine protecting group" means an easily removable group which is known in the art to protect an amino group against undesirable reaction during synthetic procedures and to be selectively removable. The use of N-protecting groups is well known in the art for protecting nitrogen-containing groups against undesirable reactions during a synthetic procedure, and many such protecting groups are known. CF, for example, T. H. Greene and P. G. M. Wuts, Protective Groups in Organic Synthesis, 2 nd edition, John Wiley & Sons, New York (1991), the contents of which are hereby incorporated herein by reference. Preferred N-protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy, including methoxycarbonyl; 9-fluorenylmethoxycarbonyl; 2,2,2-trifluoroethoxycarbonyl; 2-trimethylsilylethxoycarbonyl; vinyloxycarbonyl; allyloxycarbonyl; t-butyloxycarbonyl (BOC); 1,1-dimethylpropynyloxycarbonyl; benzyloxycarbonyl (CBZ); p-nitrophenylsulfinyl; p-nitrobenzyloxycarbonyl; 2,4-dichlorobenzyloxycarbonyl; allyloxycarbonyl (Alloc), and the like.

"Carboxylic acid protecting group" and "acid protecting group" mean an easily removable group which is known in the art to protect a carboxylic acid (—CO$_2$H) group against undesirable reaction during synthetic procedures and to be selectively removable. The use of carboxylic acid protecting groups is well known in the art, and many such protecting groups are known. CF, for example, T. H. Greene and P. G. M. Wuts, Protective Groups in Organic Synthesis, 2nd edition, John Wiley & Sons, New York (1991), the contents of which are hereby incorporated herein by reference. Examples of carboxylic acid protecting groups include esters such as methoxymethyl, methylthiomethyl, tetrahydropyranyl, benzyloxymethyl, substituted and unsubstituted phenacyl, 2,2,2-trichloroethyl, tert-butyl, cinnamyl, substituted and unsubstituted benzyl, trimethylsilyl, allyl, and the like, and amides and hydrazides including N,N-dimethyl, 7-nitroindolyl, hydrazide, N-phenylhydrazide, and the like. Especially preferred carboxylic acid protecting groups are tert-butyl and benzyl.

"Hydroxy protecting group" means an easily removable group which is known in the art to protect a hydroxy group against undesirable reaction during synthetic procedures and to be selectively removable. The use of hydroxy protecting groups is well known in the art, and many such protecting groups are known. See., for example, T. H. Greene and P. G. M. Wuts, Protective Groups in Organic Synthesis, 2nd edition, John Wiley & Sons, New York (1991). Examples of hydroxy protecting groups include ethers such as methyl; substituted methyl ethers such as methoxymethyl (MOM), methylthiomethyl (MTM), 2-methoxyethoxymethyl (MEM), bis(2-chloroethoxy)methyl, tetrahydropyranyl (THP), tetrahydrothiopyranyl, 4-methoxytetrahydropyranyl, 4-methoxytetrahydrothiopyranyl, tetrahydrofuranyl, tetrahydrothiofuranyl, and the like; substituted ethyl ethers such as 1-ethoxyethyl, 1-methyl-1-methoxyethyl, 2-(phenylselenyl)ethyl, t-butyl, allyl, benzyl, o-nitrobenzyl, triphenylmethyl, a-naphthyidiphenylmethyl, p-methoxyphenyidiphenylmethyl, 9-(9-phenyl-10-oxo) anthranyl (tritylone), and the like; silyl ethers such as trimethylsilyl (TMS), isopropyidimethylsilyl, t-butyidimethylsilyl (TBDMS), 1-butyidiphenylsilyl, tribenzylsilyl, tri-p-xylylsilyl, triisopropylsilyl, and the like; esters such as formate, acetate, trichloroacetate, phenoxyacetate, isobutyrate, pivaloate, adamantoate, benzoate, 2,4,6-trimethylbenzoate, and the like; and carbonates such as methyl, 2,2,2-trichloroethyl, allyl, p-nitrophenyl, benzyl, p-nitrobenzyl, S-benzyl thiocarbonate, and the like.

"Amino acid" means an amino acid selected from the group consisting of natural and unnatural amino acids as defined herein.

"Natural amino acid" means an α-amino acid selected from the group consisting of alanine, valine, leucine, isoleucine, proline, phenylalanine, tryptophan, methionine, glycinc, serine, threonine, cysteinc, tyrosine, asparagine, glutamine, lysine, arginine, histidine, aspartic acid and glutamic acid.

"Unnatural amino acid" means an amino acid for which there is no nucleic acid codon. Examples of unnatural amino acids include, for example, the D-isomers of the natural α-amino acids as indicated above, aminobutyric acid (Aib), 3-aminoisobutyric acid (bAib), norvaline (Nva), β-Ala, 2-aminoadipic acid (Aad), 3-aminoadipic acid (bAad), 2-aminobutyric acid (Abu), γ-aminobutyric acid (Gaba), 6-aminocaproic acid (Acp), 2,4-diaminobutryic acid (Dbu), α-aminopimelic acid, trimethylsilyl-Ala (TMSA), allo-isoleucine (aIle), norleucine (Nle), tert-Leu, citrulline (Cit), ornithine (Orn), 2,2'-diaminopimelic acid) (Dpm), 2,3-diaminopropionic acid (Dpr), α- or β-Nal, cyclohexyl-Ala (Cha), hydroxyproline, sarcosine (Sar), and the like; cyclic amino acids; N$^\alpha$-alkylated amino acids such as N$^\alpha$-methylglycine (MeGly), N$^\alpha$-ethylglycine (EtGly) and N$^\alpha$-ethylasparagine (EtAsn); and amino acids in which the α-carbon bears two side-chain substituents.

"Equivalent amino acid" means an amino acid which may be substituted for another amino acid in the peptides according to the invention without any appreciable loss of function. In making such changes, substitutions of like amino acids is made on the basis of relativelsimilarity of side chain substituents, for example regarding size, charge, hydrophilicity, hydropathicity and hydrophobicity as described herein.

"Peptide" and "polypeptide" mean a polymer in which the monomers are natural or unnatural amino acid residues joined together through amide bonds. The term "peptide backbone" means the series of amide bonds through which the amino acid residues are joined. The term "amino acid residue" means the individual amino acid units incorporated into the peptides or polypeptides.

"Aliphatic" means a radical derived from a non aromatic C—H bond by removal of the hydrogen atom. The aliphatic radical may be further substituted by additional aliphatic or aromatic radicals as defined herein. Representative aliphatic groups include alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, heteroaralkynyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, and the like. "Aliphatic", as used herein, also encompasses the residual, non-carboxyl portion of natural and unnatural amino acids as defined herein.

"Aromatic" means a radical derived from an aromatic C—H bond by removal of the hydrogen atom. Aromatic includes both aryl and heteroaryl rings as defined herein. The aryl or heteroaryl ring may be further substituted by additional aliphatic or aromatic radicals as defined herein. Representative aromatic groups include aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, fused heterocyclylheteroaryl, and the like.

"Acid bioisostere" means a group which has chemical and physical similarities producing broadly similar biological properties to a carboxylic group (see Lipinski, Annual Reports in Medicinal Chemistry, 1986,21,p283 "Bioisosterism In Drug Design"; Yun, Hwahak Sekye, 1993,33, p576–579 "Application Of Bioisosterism To New Drug Design"; Zhao, Huaxue Tongbao, 1995,p34–38 "Bioisosteric Replacement And Development Of Lead Compounds In Drug Design"; Graham, Theochem, 1995,343,p105–109 "Theoretical Studies Applied To Drug Design: ab initio Electronic Distributions In Bioisosteres"). Examples of suitable acid bioisosteres include: —C(=O)—NH—OH, C(=O)—CH$_2$OH, —C(=O)—CH$_2$SH, —C(=O)—NH—CN, sulpho, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Acylamino" is an acyl-NH— group wherein acyl is as defined herein.

"Alkenoyl" means an alkenyl-CO— group wherein alkenyl is as defined herein.

"Alkenyl" means a straight or branched aliphatic hydrocarbon group of 2 to about 15 carbon atoms which contains at least one carbon—carbon double bond. Preferred alkenyl groups have 2 to about 12 carbon atoms; more preferred alkenyl groups have 2 to about 4 carbon atoms. The alkenyl group is optionally substituted with one or more alkyl group substituents as defined herein. Representative alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" means an alkenyl-O— group wherein the alkenyl group is as herein described. Representative alkenyloxy groups include allyloxy or 3-butenyloxy.

"Alkoxy" means an alkyl-O— group wherein the alkyl group is as defined herein. Representative alkoxy groups include methoxy, ethoxy, n-propoxy, i-propoxy, n-butoxy, heptoxy, and the like.

"Alkoxyalkyl" means an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxyalkoxy" means an alkyl-O-alkylenyl-O— group. Representative alkoxyalkoxy include methoxymethoxy, methoxyethoxy, ethoxyethoxy, and the like.

"Alkoxycarbonyl" means an ester group; i.e. an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" means an alkyl-O—CO-alkylene- group wherein alkyl and alkylene are as defined herein. Representative alkoxycarbonylalkyl include methoxycarbonylmethyl, and ethoxycarbonylmethyl, methoxycarbonyl ethyl, and the like.

"Alkyl" means an aliphatic hydrocarbon group, which may be straight or branched-chain, having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means 1 to about 4 carbon atoms in the chain, which may be straight or branched. The alkyl is optionally substituted with one or more "alkyl group substituents" which may be the same or different, and include halo, cycloalkyl, hydroxy, alkoxy, amino, carbamoyl, acylamino, aroylamino, carboxy, alkoxycarbonyl, aralkyloxycarbonyl, or heteroaralkyloxycarbonyl. Representative alkyl groups include methyl, trifluoromethyl, cyclopropylmethyl, cyclopentylmethyl, ethyl, n-propyl, i-propyl, n-butyl, 1-butyl, n-pentyl, 3-pentyl, methoxyethyl, carboxymethyl, methoxycarbonylethyl, benzyloxycarbonylmethyl, and pyridylmethyloxycarbonylmethyl.

"Alkylene" means a straight or branched bivalent hydrocarbon chain of 1 to about 6 carbon atoms. The alkylene is optionally substituted with one or more "alkylene group substituents" which may be the same or different, and include halo, cycloalkyl, hydroxy, alkoxy, carbamoyl, carboxy, cyano, aryl, heteroaryl or oxo. The alkylene is optionally interrupted by, i.e., a carbon thereof is substituted by, —O—, —S(=O)$_m$ (where m is 0–2), phenylene or —NR'— (where R' is lower alkyl). Preferred alkylene groups are the lower alkylene groups having 1 to about 4 carbon atoms. Representative alkylene groups include methylene, ethylene, and the like.

"Alkenylene" means a straight or branched bivalent hydrocarbon chain containing at least one carbon—carbon double bond. The alkenylene is optionally substituted with one or more "alkylene group substituents" as defined herein. The alkenylene is optionally interrupted by, i.e., a carbon thereof is substituted by, —O—, —S(O)$_m$ (where m is 0–2), phenylene or —NR'— (where R' is lower alkyl). Representative alkenylene include —CH=CH—, —CH$_2$CH=CH—, —C(CH$_3$)=CH—, —CH$_2$CH=CHCH$_2$—, and the like.

"Alkynylene" means a straight or branched bivalent hydrocarbon chain containing at least one carbon—carbon triple bond. The alkynylene is optionally substituted with one or more "alkylene group substituents" as defined herein. The alkynylene is optionally interrupted by, i.e., a carbon thereof is substituted for, —O—, —S(O)$_m$ (where m is 0–2), phenylene or —NR'— (where R' is lower alkyl). Representative alkynylene include —C≡C—, —C≡C—CH$_2$—, —C≡C—CH(CH$_3$)—, and the like.

"Alkylsulfinyl" means an alkyl-SO— group wherein the alkyl group is as defined above. Preferred alkylsulfinyl groups are those wherein the alkyl group is lower alkyl.

"Alkylsulfonyl" means an alkyl-SO$_2$— group wherein the alkyl group is as defined herein. Preferred alkylsulfonyl groups are those wherein the alkyl group is lower alkyl.

"Alkylsulfonylcarbamoyl" means an alkyl-SO$_2$—NH—CO— group wherein alkyl group is defined herein. Preferred alkylsulfonylcarbamoyl groups are those wherein the alkyl group is lower alkyl.

"Alkylthio" means an alkyl-S— group wherein the alkyl group is as defined herein. Preferred alkylthio groups are those wherein the alkyl group is lower alkyl. Representative alkylthio groups include methylthio, ethylthio, i-propylthio, heptylthio, and the like.

"Alkynyl" means a straight or branched aliphatic hydrocarbon group of 2 to about 15 carbon atoms which contains at least one carbon—carbon triple bond. Preferred alkynyl groups have 2 to about 12 carbon atoms. More preferred alkynyl groups contain 2 to about 4 carbon atoms. "Lower alkynyl" means alkynyl of 2 to about 4 carbon atoms. The alkynyl group may be substituted by one or more alkyl group substituents as defined herein. Representative alkynyl groups include ethynyl, propynyl, n-butynyl, 2-butynyl, 3-methylbutynyl, n-pentynyl, heptynyl, octynyl, decynyl, and the like.

"Alkynyloxy" means an alkynyl-O— group wherein the alkynyl group is as defined herein. Representative alkynyloxy groups include propynyloxy, 3-butynyloxy, and the like.

"Alkynyloxyalkyl" means alkynyl-O-alkylene- group wherein alkynyl and alkylene are as defined herein.

"Amidino" or "amidine" means a group of formula

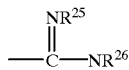

wherein R$^{25}$ is hydrogen; R$^{27}$O$_2$C— wherein R$^{27}$ is hydrogen, alkyl, aralkyl or heteroaralkyl; R$^{27}$O—; R$^{27}$C(O)—; cyano; alkyl; nitro; or amino, and R$^{26}$ is selected from hydrogen; alkyl; aralkyl; and heteroaralkyl.

"Amino" means a group of formula Y$^1$Y$^2$N— wherein Y$^1$ and Y$^2$ are independently hydrogen; acyl; or alkyl, or Y$^1$ and Y$^2$ taken together with the N through which Y$^1$ and Y$^2$ are linked form a 4 to 7 membered azaheterocyclyl. Representative amino groups include amino (H$_2$N—), methylamino, dimethylamino, diethylamino, and the like.

"Aminoalkyl" means an amino-alkylene- group wherein amino and alkylene are defined herein. Representative aminoalkyl groups include aminomethyl, aminoethyl, dimethylaminomethyl, and the like.

"Aralkenyl" means an aryl-alkenylene- group wherein aryl and alkenylene are as defined herein. Preferred aralkenyls contain a lower alkenylene moiety. A representative aralkenyl group is 2-phenethenyl.

"Aralkyloxy" means an aralkyl-O— group wherein aralkyl is defined herein. Representative aralkyloxy groups include benzyloxy, naphth-1-ylmethoxy, naphth-2-ylmethoxy, and the like.

"Aralkyloxyalkyl" means an aralkyl-O-alkylene- group wherein aralkyl and alkylene are as defined herein. A representative aralkyloxyalkyl group is benzyloxyethyl.

"Aralkyloxycarbonyl" means an aralkyl-O—CO— group wherein aralkyl is as defined herein. A representative aralkoxycarbonyl group is benzyloxycarbonyl.

"Aralkyloxycarbonylalkyl" means an aralkoxycarbonyl-alkylene- group wherein aralkyloxycarbonyl and alkylene are as defined herein. Representative aralkoxycarbonylalkyls include benzyloxycarbonylmethyl, and benzyloxycarbonylethyl.

"Aralkyl" means an aryl-alkylene- group wherein aryl and alkylene are as defined herein. Preferred aralkyls contain a lower alkyl moiety. Representative aralkyl groups include benzyl, 2-phenethyl, naphthlenemethyl, and the like.

"Aralkyloxyalkenyl" means an aralkyl-O-alkenylene- group wherein aralkyl and alkenylene are as defined herein. A representative aralkyloxyalkenyl group is 3-benzyloxyallyl.

"Aralkylsulfonyl" means an aralkyl-SO$_2$— group wherein aralkyl is as defined herein.

"Aralkylsulfinyl" means an aralkyl-SO— group wherein aralkyl is as defined herein.

"Aralkylthio" means an aralkyl-S— group wherein aralkyl is as defined herein. A representative aralkylthio group is benzylthio.

"Aroyl" means an aryl-CO— group wherein aryl is defined herein. Representative aroyl include benzoyl, naphth-1-oyl and naphth-2-oyl.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl is optionally substituted with one or more "ring system substituents" which may be the same or different, and are as defined herein, or where R$^{18}$ is a substituted cycloalkyl, the cycloalkyl is substituted by one or more (e.g. 1, 2 or 3) substituents chosen from OR$^{23}$, SR$^{24}$, SOR$^{24}$, SO$_2$R$^{24}$, NH$_2$, NR$^{22}$R$^{24}$, =NOR$^{24}$, =NOH, =NNHR$^{24}$, =NOCONHR$^{24}$, =NCO$_2$R$^{24}$, SOR$^{24}$, NHCOR$^{24}$, NHSO$_2$R$^{24}$, SO$_2$NR$^{22}$R$^{24}$, R$^{23}$, CONHR$^{24}$, CONHCH$_2$CO$_2$R$^{22}$, CONR$^{24}$R$^{22}$, N$_3$ or azaheterocyclyl; wherein R$^{22}$ is as defined herein; R$^{23}$ is hydrogen, alkyl, cycloalkyl, aryl, arylalkyl, heteroaryl or heteroarylalkyl; and R$^{24}$ is alkyl, cycloalkyl, cycloalkenyl, heterocycloalkyl, aryl, arylalkyl, heteroaryl or heteroarylalkyl. Representative monocyclic cycloalkyl include cyclopentyl, cyclohexyl, cycloheptyl, and the like. Representative multicyclic cycloalkyl include 1-decalin, norbornyl, adamantyl, and the like. The prefix spiro before cycloalkyl means that geminal substituents on a carbon atom are replaced to form 1,1-cycloalkyl. "Cycloalkylene" means a bivalent cycloalkyl having about 4 to about 8 carbon atoms. Preferred cycloalkylenyl groups include 1,2-, 1,3-, or 1,4- cis or trans-cyclohexylene.

"Cycloalkenyl" means a non-aromatic mono- or multicyclic ring system of about 3 to about 10 carbon atoms, preferably of about 5 to about 10 carbon atoms which contains at least one carbon—carbon double bond. Preferred cycloalkylene rings contain about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl.

"Cyclocarbamoylalkyl" means a compound of formula

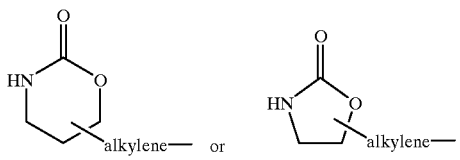

which the cyclocarbamoyl group consists of the oxooxazaheterocyclyl ring moiety, and the alkylene group is as defined herein. The alkylene moiety may be attached to the carbamoyl through either a carbon atom or the nitrogen atom of the carbamoyl moiety. An exemplary cyclocarbamoylalkyl group is N-oxazolidinylpropyl.

"Cycloimidylalkyl" means a compound of formula

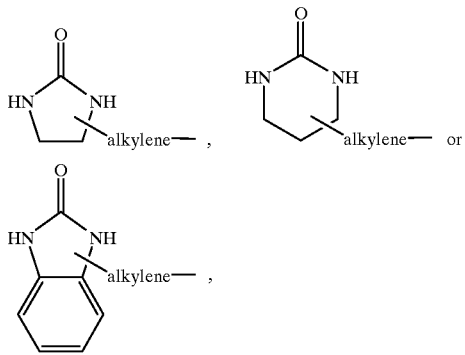

in which the imide group consists of the oxodiazaheterocyclyl ring moiety, and alkylene is as defined herein. The alkylene moiety may be attached to the carbamoyl through either a carbon atom or nitrogen atom of the carbamoyl moiety. An exemplary cycloimidylalkyl group is N-phthalimidepropyl.

"Heterocyclenyl" means a non-aromatic monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur atoms, and which contains at least one carbon—carbon double bond or carbon-nitrogen double bond. Preferred heterocyclenyl rings contain about 5 to about 6 ring atoms. The prefix aza, oxa or thia before heterocyclenyl means that at least a nitrogen, oxygen or sulfur atom, respectively, is present as a ring atom. The heterocyclenyl is optionally substituted by one or more ring system substituents, wherein "ring system substituent" is as defined herein. The nitrogen or sulphur atom of the heterocyclenyl is optionally oxidized to the corresponding N-oxide, S-oxide or S,S-dioxide. Representative monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Representative oxaheterocyclenyl groups include 3,4-dihydro-2H-pyran, dihydrofuranyl, fluorodihydrofuranyl, and the like. A representative multicyclic oxaheterocyclenyl group is 7-oxabicyclo[2.2.1]heptenyl. Representative monocyclic thiaheterocyclenyl rings include dihydrothiophenyl, dihydrothiopyranyl, and the like "Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to about 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein, or wherein $R^{18}$ is a substituted heterocyclyl, the heterocyclyl is substituted the ring carbon atoms by one or more (e.g. 1, 2 or 3) substituents chosen from oxo, cyano, $CO_2R^{22}$, $CONHCH_2CO_2R^{22}$, aryl, arylalkyl, alkyl or hydroxyalkyl, or is substituted on a ring nitrogen atom by a substituent chosen from $R^{22}$, $(CH_2)_nCO_2H$, $(CH_2)_nCO_2R^{24}$, $(CH_2)_nCONR^{22}R^{24}$, $(CH_2)_nCOR^{24}$, $CONH_2$, $CONHR^{24}$, $COR^{24}$, $SO_2R^{24}$, or $OR^{24}$, wherein $R^{22}$ and $R^{24}$ are as defined herein. The nitrogen or sulphur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aryl" means an aromatic monocyclic or multicyclic ring system of 6 to about 14 carbon atoms, preferably of 6 to about 10 carbon atoms. The aryl is optionally substituted with one or more "ring system substituents" which may be the same or different, and are as defined herein. Representative aryl groups include phenyl and naphthyl.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to about 6 ring atoms. The "heteroaryl" is optionally substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Fused arylcycloalkenyl" means a radical derived from a fused aryl and cycloalkenyl as defined herein by removal of hydrogen atom from the cycloalkenyl portion. Preferred fused arylcycloalkenyls are those wherein aryl is phenyl and the cycloalkenyl consists of about 5 to about 6 ring atoms. The fused arylcycloalkenyl is optionally substituted by one or more ring system substituents, wherein "ring system substituent" is as defined herein. Representative fused arylcycloalkenyl include 1,2-dihydronaphthalene, indene, and the like, in which the bond to the parent moiety is through a nonaromatic carbon atom.

"Fused cycloalkenylaryl" means a radical derived from a fused aryl and cycloalkenyl as defined herein by removal of hydrogen atom from the aryl portion. Representative fused cycloalkenylaryl are as described herein for a fused arylcycloalkenyl, except that the bond to the parent moiety is through an aromatic carbon atom.

"Fused arylcycloalkyl" means a radical derived from a fused aryl and cycloalkyl as defined herein by removal of a hydrogen atom from the cycloalkyl portion. Preferred fused arylcycloalkyls are those wherein aryl is phenyl and the cycloalkyl consists of about 5 to about 6 ring atoms. The fused arylcycloalkyl is optionally substituted by one or more ring system substituents, wherein "ring system substituent" is as defined herein. Representative fused arylcycloalkyl includes 1,2,3,4-tetrahydronaphthyl, and the like, in which the bond to the parent moiety is through a non-aromatic carbon atom.

"Fused cycloalkylaryl" means a radical derived from a fused aryl and cycloalkyl as defined herein by removal of a hydrogen atom from the aryl portion. Representative fused cycloalkylaryl are as described herein for a fused arylcycloalkyl radical, except that the bond to the parent moiety is through an aromatic carbon atom.

"Fused arylheterocyclenyl" means a radical derived from a fused aryl and heterocyclenyl as defined herein by removal of a hydrogen atom from the heterocyclenyl portion. Preferred fused arylheterocyclenyls are those wherein aryl is phenyl and the heterocyclenyl consists of about 5 to about 6 ring atoms. The prefix aza, oxa or thia before the heterocyclenyl portion of the fused arylheterocyclenyl means that at least a nitrogen, oxygen or sulfur atom respectively is present as a ring atom. The fused arylheterocyclenyl is optionally substituted by one or more ring system substituents, wherein "ring system substituent" is as defined herein. The nitrogen or sulphur atom of the heterocyclenyl portion of the fused arylheterocyclenyl is optionally oxidized to the corresponding N-oxide, S-oxide or S,S-dioxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like, in which the bond to the parent moiety is through a non-aromatic carbon atom.

"Fused heterocyclenylaryl" means a radical derived from a fused aryl and heterocyclenyl as defined herein by removal of a hydrogen atom from the aryl portion. Representative fused heterocyclenylaryl are as defined herein for a fused arylheterocyclenyl radical, except that the bond to the parent moiety is through an aromatic carbon atom.

"Fused arylheterocyclyl" means a radical derived from a fused aryl and heterocyclyl as defined herein by removal of a hydrogen atom from the heterocyclyl portion. Preferred fused arylheterocyclyls are those wherein aryl is phenyl and the heterocyclyl consists of about 5 to about 6 ring atoms. The prefix aza, oxa or thia before heterocyclyl means that at least a nitrogen, oxygen or sulfur atom respectively is present as a ring atom. The fused arylheterocyclyl is optionally substituted by one or more ring system substituents, wherein "ring system substituent" is as defined herein. The nitrogen or sulphur atom of the heterocyclyl portion of the fused arylheterocyclyl is optionally oxidized to the corresponding N-oxide, S-oxide or S,S-dioxide. Representative preferred fused arylheterocyclyl ring systems include phthalimide, 1,4-benzodioxane, indolinyl, 1,2,3,4-tetrahydroisoquinoline, 1,2,3,4-tetrahydroquinoline, 1H-2,3-dihydroisoindolyl, 2,3-dihydrobenz[f]isoindolyl, 1,2,3,4-tetrahydrobenz[g]isoquinolinyl, and the like, in which the bond to the parent moiety is through a non-aromatic carbon atom.

"Fused heterocyclylaryl" means a radical derived from a fused aryl and heterocyclyl as defined herein by removal of a hydrogen atom from the heterocyclyl portion. Representative preferred fused heterocyclylaryl ring systems are as described for fused arylheterocyclyl, except that the bond to the parent moiety is through an aromatic carbon atom.

"Fused heteroarylcycloalkenyl" means a radical derived from a fused heteroaryl and cycloalkenyl as defined herein by removal of a hydrogen atom from the cycloalkenyl portion. Preferred fused heteroarylcycloalkenyls are those wherein the heteroaryl and the cycloalkenyl each contain about 5 to about 6 ring atoms. The prefix aza, oxa or thia before heteroaryl means that at least a nitrogen, oxygen or sulfur atom respectively is present as a ring atom. The fused heteroarylcycloalkenyl is optionally substituted by one or more ring system substituents, wherein "ring system substituent" is as defined herein. The nitrogen atom of the heteroaryl portion of the fused heteroarylcycloalkenyl is optionally oxidized to the corresponding N-oxide. Representative fused heteroarylcycloalkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like, in which the bond to the parent moiety is through a non-aromatic carbon atom.

"Fused cycloalkenylheteroaryl" means a radical derived from a fused heteroaryl and cycloalkenyl as defined herein by removal of a hydrogen atom from the heteroaryl portion. Representative fused cycloalkenylheteroaryl are as described herein for fused heteroarylcycloalkenyl, except that the bond to the parent moiety is through an aromatic carbon atom.

"Fused heteroarylcycloalkyl" means a radical derived from a fused heteroaryl and cycloalkyl as defined herein by removal of a hydrogen atom from the cycloalkyl portion. Preferred fused heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The fused heteroarylcycloalkyl is optionally substituted by one or more ring system substituents, wherein "ring system substituent" is as defined herein. The nitrogen atom of the heteroaryl portion of the fused heteroarylcycloalkyl is optionally oxidized to the corresponding N-oxide. Representative fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like, in which the bond to the parent moiety is through a non-aromatic carbon atom.

"Fused cycloalkylheteroaryl" means a radical derived from a fused heteroaryl and cycloalkyl as defined herein by removal of a hydrogen atom from the heteroaryl portion. Representative fused cycloalkylheteroaryl are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl as defined herein by the removal of a hydrogen atom from the heterocyclenyl portion. Preferred fused heteroarylheterocyclenyls are those wherein the heteroaryl thereof consists of about 5 to about 6 ring atoms and the heterocyclenyl consists of about 5 to about 6 ring atoms. The prefix aza, oxa or thia before heteroaryl or heterocyclenyl means that at least a nitrogen, oxygen or sulfur atom is present respectively as a ring atom. The fused heteroarylheterocyclenyl is optionally substituted by one or more ring system substituents, wherein "ring system substituent" is as defined herein. The nitrogen atom of the heteroaryl portion of the fused heteroarylheterocyclenyl is optionally oxidized to the corresponding N-oxide. The nitrogen or sulphur atom of the heterocyclenyl portion of the fused heteroarylheterocyclenyl is optionally oxidized to the corresponding N-oxide, S-oxide or S,S-dioxide. Representative fused heteroarylheterocyclenyl include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like, in which the bond to the parent moiety is through a non aromatic carbon atom.

"Fused heterocyclenylheteroaryl" means a radical derived from a fused heteroaryl and heterocyclenyl as defined herein by the removal of a hydrogen atom from the heteroaryl portion. Representative fused heterocyclenylheteroaryl are as described herein for fused heteroarylheterocyclenyl, except that the bond to the parent moiety is through an aromatic carbon atom.

"Fused heteroarylheterocyclyl" means a radical derived from a fused heteroaryl and heterocyclyl as defined herein, by removal of a hydrogen atom from the heterocyclyl portion. Preferred fused heteroarylheterocyclyls are those wherein the heteroaryl thereof consists of about 5 to about 6 ring atoms and the heterocyclyl consists of about 5 to about 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroaryiheterocyclyl is optionally substituted by one or more ring system substituents, wherein "ring system substituent" is as defined herein. The nitrogen atom of the heteroaryl portion of the fused heteroarylheterocyclyl is optionally oxidized to the corresponding N-oxide. The nitrogen or sulphur atom of the heterocyclyl portion of the fused heteroarylheterocyclyl is optionally oxidized to the corresponding N-oxide, S-oxide or S,S-dioxide. Representative fused heteroarylheterocyclyl include 2,3-dihydro-1H pyrrol [3,4-b]quinolin-2-yl, 1,2,3,4-tetrahydrobenz[b][1,7] naphthyridin-2-yl, 1,2,3,4-tetrahydrobenz[b][1,6] naphthyridin-2-yl, 1,2,3,4-tetrahydro-9H-pyrido[3,4-b]indol-2-yl, 1,2,3,4-tetrahydro-9H-pyrido[4,3-b]indol-2yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2 yl, 5,6,7,8-tetrahydro[1,7]napthyridinyl, 1,2,3,4-tetrhydro[2,7]naphthyridyl, 2,3-dihydro[1,4]dioxino[2,3-b]pyridyl, 2,3-dihydro[1,4]dioxino[2,3-b]pryidyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]napthyridinyl, 1,2,3,4-tetrahydro[1,6] napthyridinyl, 1,2,3,4-tetrahydro[1,7]napthyridinyl, 1,2,3,4-tetrahydro[1,8]napthyridinyl, 1,2,3,4-tetrahydro[2,6] napthyridinyl, and the like, in which the bond to the parent moiety is through a non-aromatic carbon atom.

"Fused heterocyclylheteroaryl" means a radical derived from a fused heteroaryl and heterocyclyl as defined herein, by removal of a hydrogen atom from the heteroaryl portion. Representative fused heterocyclylheteroaryl are as described herein for fused heteroarylheterocyclyl, except that the bond to the parent moiety is through an aromatic carbon atom.

"Aralkynyl" means an aryl-alkynylene- group wherein aryl and alkynylene are defined herein. Representative aralkynyl groups include phenylacetylenyl and 3-phenylbut-2-ynyl.

"Aryldiazo" means an aryl-N=N— group wherein aryl is defined herein. Representative aryidiazo groups include phenyldiazo and naphthyidiazo.

"Arylcarbamoyl" means an aryl-NHCO— group, wherein aryl is defined herein.

"Benzyl" means a phenyl-$CH_2$— group. Substituted benzyl means a benzyl group in which the phenyl ring is substituted with one or more ring system substituents. Representative benzyl include 4-bromobenzyl, 4-methoxybenzyl, 2,4-dimethoxybenzyl, and the like.

"Carbamoyl" means a group of formula $Y^1Y^2NCO$— wherein $Y^1$ and $Y^2$ are defined herein. Representative carbamoyl groups include carbamyl ($H_2NCO$—), dimethylaminocarbamoyl ($Me_2NCO$—), and the like.

"Carboxy" and "carboxyl" mean a HO(O)C— group (i.e. a carboxylic acid).

"Carboxyalkyl" means a HO(O)C-alkylene- group wherein alkylene is defined herein. Representative carboxyalkyls include carboxymethyl and carboxyethyl.

"Cycloalkyloxy" means a cycloalkyl-O— group wherein cycloalkyl is as defined herein. Representative cycloalkyloxy groups include cyclopentyloxy, cyclohexyloxy, and the like.

"Diazo" means a bivalent —N=N— radical.

"Ethylenyl" means a —CH=CH— group.

"Halo" or "halogen" mean fluoro, chloro, bromo, or iodo.

"Heteroaralkenyl" means a heteroaryl-alkenylene- group wherein heteroaryl and alkenylene are as defined herein. Preferred heteroaralkenyls contain a lower alkenylene moiety. Representative heteroaralkenyl groups include 4-pyridylvinyl, thienylethenyl, pyridylethenyl, imidazolylethenyl, pyrazinylethenyl, and the like.

"Heteroaralkyl" means a heteroaryl-alkylene- group wherein heteroaryl and alkylene are as defined herein. Preferred heteroaralkyls contain a lower alkylene group. Representative heteroaralkyl groups include thienylmethyl, pyridylmethyl, imidazolylmethyl, pyrazinylmethyl, and the like.

"Heteroaralkyloxy" means an heteroaralkyl-O— group wherein heteroaralkyl is as defined herein. A representative heteroaralkyloxy group is 4-pyridylmethyloxy.

"Heteroaralkyloxyalkenyl" means a heteroaralkyl-O-alkenylene- group wherein heteroaralkyl and alkenylene are as defined herein. A representative heteroaralkyloxyalkenyl group is 4-pyridylmethyloxyallyl.

"Heteroaralkyloxyalkyl" means a heteroaralkyl-O-alkylene- group wherein heteroaralkyl and alkylene are as defined herein. A representative heteroaralkyloxy group is 4-pyridylmethyloxyethyl.

"Heteroaralkynyl" means an heteroaryl-alkynylene-group wherein heteroaryl and alkynylene are as defined herein. Preferred heteroaralkynyls contain a lower alkynylene moiety. Representative heteroaralkynyl groups include pyrid-3-ylacetylenyl, quinolin-3-ylacetylenyl, 4-pyridylethynyl, and the like.

"Heteroaroyl" means an means a heteroaryl-CO— group wherein heteroaryl is as defined herein. Representative heteroaroyl groups include thiophenoyl, nicotinoyl, pyrrol-2-ylcarbonyl, pyridinoyl, and the like.

"Heteroaryidiazo" means an heteroaryl-N=N— group wherein heteroaryl is as defined herein.

"Heteroarylsulphonylcarbamoyl" means a heteroaryl-$SO_2$—NH—CO— group wherein heteroaryl is as defined herein.

"Heterocyclylalkyl" means a heterocyclyl-alkylene-group wherein heterocyclyl and alkylene are as defined herein. Preferred heterocyclylalkyls contain a lower alkylene moiety. A representative heteroaralkyl group is tetrahydropyranylmethyl.

"Heterocyclylalkyloxyalkyl" means a heterocyclylalkyl-O-alkylene group wherein heterocyclylalkyl and alkylene are as defined herein. A representative heterocyclylalkyloxyalkyl group is tetrahydropyranylmethyloxymethyl.

"Heterocyclyloxy" means a heterocyclyl-O— group wherein heterocyclyl is as defined herein. Representative heterocyclyloxy groups include quinuclidyloxy, pentamethylenesulfideoxy, tetrahydropyranyloxy, tetrahydrothiophenyloxy, pyrrolidinyloxy, tetrahydrofuranyloxy, 7-oxabicyclo[2.2.1]heptanyloxy, hydroxytetrahydropyranyloxy, hydroxy-7-oxabicyclo[2.2.1]heptanyloxy, and the like.

"Hydroxyalkyl" means an alkyl group as defined herein substituted with one or more hydroxy groups. Preferred hydroxyalkyls contain lower alkyl. Representative hydroxyalkyl groups include hydroxymethyl and 2-hydroxyethyl.

"N-oxide" means a

group.

"Oxo" means a group of formula >C=O (i.e., a carbonyl group).

"Phenoxy" means a phenyl-O— group wherein the phenyl ring is optionally substituted with one or more ring system substituents as defined herein.

"Phenylene" means a -phenyl- group wherein the phenyl ring is optionally substituted with one or more ring system substituents as defined herein.

"Phenylthio" means a phenyl-S— group wherein the phenyl ring is optionally substituted with one or more ring system substituents as defined herein.

"Pyridyloxy" means a pyridyl-O— group wherein the pyridyl ring is optionally substituted with one or more ring system substituents as defined herein.

"Ring system substituents" mean substituents attached to aromatic or non-aromatic ring systems inclusive of hydrogen, alkyl, aryl, heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, nitrile, $NO_2$ heteroarylthio, aralkylthio, heteroaralkylthio, cycloalkyl, cycloalkenyl, heterocyclyl, heterocyclenyl, aryidiazo, heteroaryldiazo, amidino, $Y^1Y^2N$—, $Y^1Y^2N$-alkyl-, $Y^1Y^2NCO$— or $Y^1Y^2NSO_2$—, wherein $Y^1$ and $Y^2$ are independently hydrogen, alkyl, aryl, and aralkyl, or where the substituent is $Y^1Y^2N$— or $Y^1Y^2N$-alkyl- then one of $Y^1$ and $Y^2$ is acyl or aroyl and the other of $Y^1$ and $Y^2$ is hydrogen, alkyl, aryl, and aralkyl. When a ring system is saturated or partially saturated, the "ring system substituent" further comprises methylene (H2C=), oxo (O=) and thioxo (S=). Preferred ring system substituents are hydrogen, $CF_3$, fluoro, alkyl, alkoxy, nitrile or $NO_2$.

"Sulfamoyl" means a group of formula $Y^1Y^2NSO_2$— wherein $Y^1$ and $Y^2$ are defined herein. Representative sulfamoyl groups are sulfamoyl ($H_2NSO_2$—) and dimethylsulfamoyl ($Me_2NSO_2$—).

PREFERRED EMBODIMENTS

A process for the preparation of aldehydes and ketones according to this invention is outlined in Scheme 1 wherein $R_a$ and $R_b$ independently represent any aliphatic or aromatic group amenable to the solvents and reagents utilized in the processes described herein. The groups $R_a$ and $R_b$ may be further substituted and may contain functional groups suitable for further chemical transformations while attached to the hydroxylamine resin. Such functional groups may be suitable protected to prevent interference with the reactions described below. For a comprehensive treatise on the protection and deprotection of common functional groups see T. H. Greene and P. G. M. Wuts, Protective Groups in Organic Synthesis, 2nd edition, John Wiley & Sons, New York (1991), incorporated herein by reference. $R_c$ represents any aliphatic or aromatic group suitable for use as an organometallic reagent.

Scheme 1

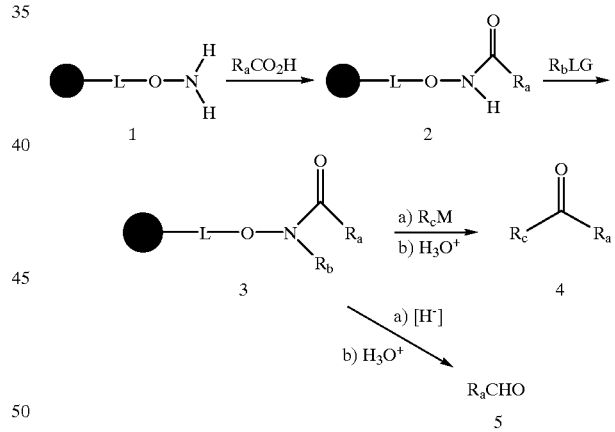

According to the foregoing Scheme 1, a polymeric hydroxylamine resin compound 1 is coupled with a carboxylic acid derivative of formula $R_aCO_2H$ to form the polymeric hydroxamic acid resin compound 2. The coupling reaction is accomplished in the presence of an activating agent as is known in the art of peptide synthesis. Representative activating agents include isopropyl chloroformate, diisopropylcarbodiimide (DIC), 1-(3-dimethylaminopropyl)-3-ethylcarbodiimide (EDC), 1-hydroxybenzotriazole (HOBT), bis(2-oxo-3-oxazolidinyl)-phosphonic chloride (BOP-Cl), benzotriazole-1-yloxy-tris((dimethylamino)phosphonium) hexafluorophosphate (BOP), benzotriazole-1-yloxy-tris-pyrrolidino-phosphonium hexafluorophosphate (PyBROP), bromo-tris-pyrrolidino-phosphonium hexafluorophosphate (PyBOP), 2-(1H-benzotriazole-1-yl)-1.1.3.3-tetramethyluronium tetrafluoroborate (TBTU), 2-(1H-benzotriazole-1-yl)-1.1.3.3-tetramethyluronium hexafluoroborate (HBTU), 2-[2-oxo-1-(2H)-pyridyl]-1,1,3,3-bispentamethyleneuronoium tetrafluoroborate (TOPPipU), N,N'-dicyclohexylcarbodiimide (DCC), and the like. Suitable solvents for the coupling reaction include dichloromethane, DMF, DMSO, THF, and the like. Coupling times range from about 2 to about 24 hours, depending upon the resin and carboxylic acid derivative to be coupled, activating agent, solvent and temperature. The coupling is accomplished at from about −10° C. to about 50° C., preferably at about ambient temperature.

The coupling reaction is preferably accomplished at ambient temperature in DMF using 1-(3-dimethylaminopropyl)-3-ethylcarbodiimide hydrochloride over about 12 hours.

The polymeric hydroxamic acid resin compound 2 is then alkylated with an alkylating agent of formula $R_bLG$, where LG is a leaving group, in the presence of a non-nucleophilic base such as 1,8-diazabicyclo[5.4.0]undec-7-ene (DBU) in an inert organic solvent such as toluene to form the N-alkylated polymeric hydroxamic acid resin compound 3. The alkylating agent $R_bLG$ may be added in an equimolar amount to an excess of to about 25 molar equivalents. About 15 molar equivalents is preferred. The non-nucleophilic base may be added in an equimolar amount to an excess of to about 10 molar equivalents. About 5 molar equivalents is preferred. The leaving group LG is any group amenable to nucleophilic displacement by the nitrogen atom of the polymeric hydroxamic acid resin compound 2 under the reaction conditions described above. A preferred leaving group is halogen. A sample of the N-alkylated polymeric hydroxamic acid resin compound 3 may be subjected to acidolysis to cleave the substituted hydroxamic acid to confirm that the reaction proceeded satisfactorily.

Reaction of the polymeric N-alkylated hydroxamic acid resin compound 3 with an organometallic reagent of formula $R_cM$, wherein $R_c$ is an aliphatic or aromatic anion and M is a metal cation, followed by acid hydrolysis provides the ketone 4. Preferred organometallic reagents are organolithium reagents of formula $R_cLi$ and Grignard reagents of formula $R_cMgX$ wherein X is halogen. In a preferred preparation of ketones according to this aspect of the invention, the polymeric N-alkylated hydroxamic acid resin compound 3 is treated with $R_cMgX$ in diethyl ether at ambient temperature over about 18 hours, and the reaction mixture is then quenched by addition of aqueous HCl or aqueous $KHSO_4$ to liberate the ketone 4.

Aldehydes are prepared by treatment of the polymeric N-alkylated hydroxamic acid resin compound 3 with a hydride reducing agent, followed by acid hydrolysis as shown in Scheme 1 above. Representative hydride reducing agents include $LiAlH_4$, $(iso-Bu)_2AlH$, $LiAlH(O-t-Bu)_3$, $LiAlH_4$—EtOH, $LiAlH_4$—MeOH, and the like. Preferred reducing agents are $LiAlH_4$ and $LiAlH_4$—MeOH. The acid hydrolysis is preferably accomplished aqueous $KHSO_4$.

As shown in Scheme 1, the N-alkylated polymeric hydroxamic acid resin compound 3 is a Weinreb-like amide useful for the synthesis of aldehydes and ketones (S. Nahm and S. Weinreb, Tet Lett. 1981, 22, 3815–3818). This N-alkylated polymeric hydroxamic acid resin compound has advantages over the previous examples of resin bound Weinreb-like amides (See Fehrentz et al., Tet. Lett., 1995, 36, 7871–7874 and Dinh et al., Tet. Lett., 1996, 37, 1161–1164) in that it can be N-alkylated with bulky lipophilic groups such as benzyl, substituted benzyl, naphthyl or any alkyl group necessary to optimize the reaction on the solid phase. The N-benzyl-O-methylpolystyrenyl moiety, for example, is well suited to form a stable metal chelated intermediate. The lipophilic benzyl group is believed to help shield the chelate adding to its stability.

A preferred process for the preparation of aldehydes and ketones is outlined in Scheme 2. In Scheme 2, "P" designates an amine protecting group as defined herein.

Scheme 2

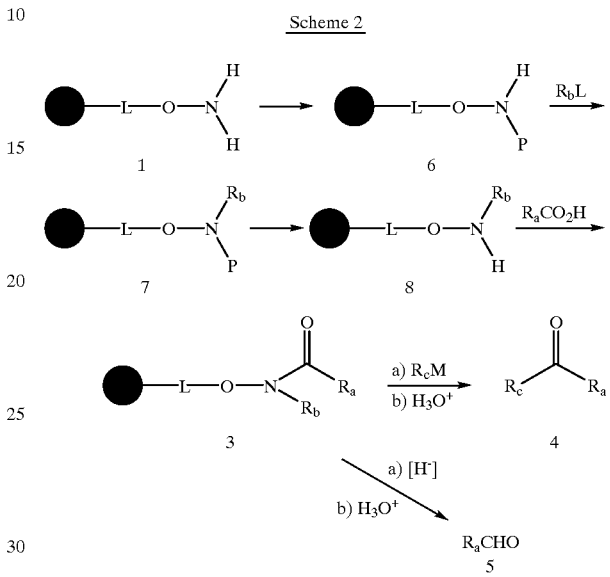

As shown in Scheme 2 above, the polymeric hydroxylamine resin compound is protected with an amine protecting group to form the N-protected polymeric hydroxylamine resin compound 6. The N-protected polymeric hydroxylamine resin compound 6 is then alkylated as described in Scheme 1 above to form the N-alkylated N-protected polymeric hydroxylamine resin compound 7. Removal of the amine protecting group provides the mono N-alkylated polymeric hydroxylamine resin compound 8. Coupling of 8 with a carboxylic acid compound of formula $R_aCO_2H$ as described above provides the polymeric N-alkylated hydroxamic acid resin compound 3, which is converted to ketone 4 or aldehyde 5 as described in Scheme 1 above.

Preferred amine protecting groups "P" include allyloxycarbonyl (Aloc), benzyloxycarbonyl (Cbz), p-methoxybenzyloxycarbonyl (Moz), p-nitrobenzyloxycarbonyl (4—$NO_2$—Z), trimethylsilylethoxycarbonyl (Teoc), 2,4-dimethoxybenzyloxycarbonyl, o-nitrobenzyloxycarbonyl, o-nitrobenzylsulfonyl (o-Nbs), p-nitrobenzylsulfonyl (p-Nbs), and 2-nitro-4-trifluoromethylbenzenesulfonyl.

The most preferred amine protecting group is allyloxycarbonyl.

In a preferred aspect of the processes described in Schemes 1 and 2 above, $R_a$ represents the residual, noncarboxyl portion of a natural or unnatural amino acid or peptide. Accordingly, the foregoing processes present a facile route to the heretofore difficult to obtain amino acid or peptide aldehyde compounds.

In a process for preparing amino acid aldehyde or peptide amino acids according to this invention, the N-terminal nitrogen atom of the amino acid or peptide starting material is preferably protected with a suitable amine protecting group, designated herein as P'''. Furthermore, any functional groups contained in the amino acid or peptide side chain(s) may be suitably protected to prevent interference with the reactions described herein.

In a preferred aspect of the preparation of amino acid or peptide aldehydes described above, $R_b$ is benzyl or substituted benzyl.

In a more preferred aspect of the preparation of amino acid or peptide aldehydes described above, $R_b$ is benzyl or benzyl substituted with halogen, haloalkyl or alkoxy and P''' is t-butyloxycarbonyl (BOC).

In addition, the N-alkylated hydroxamic acid resin compound 3 in which $R_a$ is the residual noncarboxyl portion of a natural amino acid or peptide are amino acid or peptide aldehyde equivalents which may be stored and used to generate the corresponding amino acid or peptide aldehyde as needed by treatment with a hydride reducing agent and acid hydrolysis as described above.

Preferred polymeric N-protected hydroxylamine resin compounds include

N-allyloxycarbonyl-4-(O-methylhydroxylamine)phenoxymethyl-copoly(styrene-1% divinylbenzene) resin, N-allyloxycarbonyl-4-[4-(O-methylhydroxylamine)-3-methoxyphenoxy]-(N-4-methylbenzhydryl)-butyramide-copoly(styrene-1%-divinylbenzene)-resin, N-allyloxycarbonyl-4-(2',4'-dimethoxyphenyl-O-methylhydroxylamine)-phenoxymethyl-copoly(styrene-1% divinylbenzene)resin, N-allyloxycarbonyl-4-[4-(1-aminoxyethyl)-2-methoxy-5-nitrophenoxy]-(N-4-methylbenzhydryl)-butyramide-copoly(styrene-1% divinylbenzene)resin, N-allyloxycarbonyl-O-hydroxylamine-2'-chlorotrityl-copolystyrene-1%-divinylbenzene-resin, N-allyloxycarbonyl-O-hydroxylamine-trityl-copolystyrene-1%-divinylbenzene-resin, N-allyloxycarbonyl-5-(4-O-methylhydroxylamine-3,5-dimethoxyphenoxy)-valeric acid-copolystyrene-1%-divinyl benzene resin, N-allyloxycarbonyl-4-O-methylhydroxylamine-3-methoxyphenoxy-copolystyrene-1%-divinyl benzene resin, N-allyloxycarbonyl-4-(O-methylhydroxylamine)-2,3,5,6-tetrafluorophenoxymethyl-copoly(styrene-1% divinylbenzene)resin, N-allyloxycarbonyl-4-(2',4'-dimethoxyphenyl-O-methylhydroxylamine)-2,3,5,6-tetrafluorophenoxymethyl-copoly(styrene-1% divinylbenzene)resin and N-allyloxycarbonyl-3-hydroxy-xanthydrolamine-copolystryene-1%-divinylbenzene resin.

The most preferred polymeric N-protected hydroxylamine resin compound is N-allyloxycarbonyl-4-(O-methylhydroxylamine)phenoxymethyl-copoly(styrene-1% divinylbenzene)resin.

A process for the preparation of amines according to this invention is outlined in Scheme 3. In Scheme 3, $R_d$ and $R_e$ independently represent H or any aliphatic or aromatic group amenable to the solvents and reagents utilized in the processes described herein, provided that $R_d$ and $R_e$ are not both H. The groups $R_a$, $R_b$ and $R_c$ may be further substituted and may contain functional groups suitable for further chemical transformations while attached to the hydroxylamine resin. It is understood that when these functional groups possess reactivity such that they could potentially interfere with the reactions described below, such functional groups should be suitably protected. For a comprehensive treatise on the protection and deprotection of common functional groups see T. H. Greene and P. G. M. Wuts, Protective Groups in Organic Synthesis, 2nd edition, John Wiley & Sons, New York (1991), incorporated herein by reference. $R_f$ represents any aliphatic or aromatic group which is amenable for use as an organometallic reagent.

Scheme 3

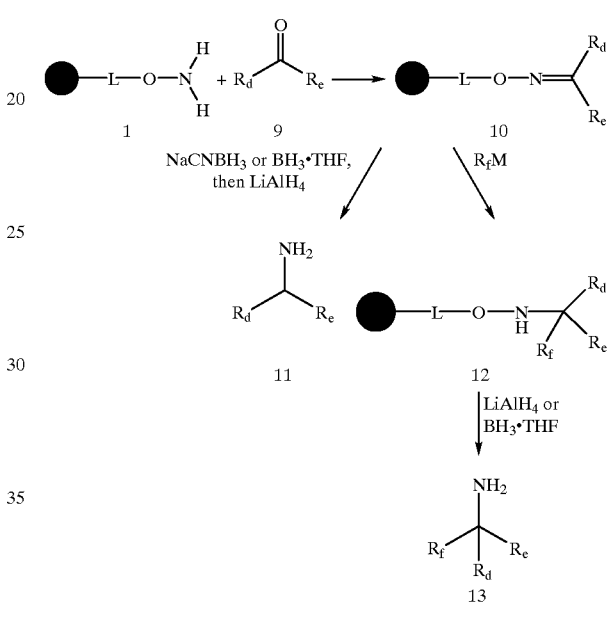

According to the foregoing Scheme 3, reaction of the polymeric hydroxylamine resin compound 1 with an aldehyde or ketone 9 provides the polymeric oxime ether resin compound 10. Oxime formation is preferably accomplished at about ambient temperature by swelling the polymeric hydroxylamine resin compound 1 in a suitable inert organic solvent such as dichloromethane, followed by addition of an excess of aldehyde or ketone. Reductive cleavage of the resin, for example by reaction with $NaCNBH_3$, or $BH_3THF$, followed by $LiAlH_4$ provides the amine 11. Reaction of the polymeric oxime ether resin compound 10 with an organometallic reagent of formula $R_fM$, wherein $R_f$ is an aliphatic or aromatic anion and M is a metal cation as defined herein, provides the polymeric α-substituted hydroxylamine resin compound 12. Cleavage of the α-amine 13 from the resin, is accomplished, for example, using $BH_3THF$ or $LiAlH_4$. See Y. Ukaji et al., Chem. Lett., 173, (1991) and R. P. Dieter et al., Can. J. Chem. 71, 814 (1993). Preferred metal cations are Li and MgX wherein X is halogen. With the aid of a chiral auxiliary such as a chiral benzyl hydroxyl amine linker, chiral α-substituted amines will result.

A process for the preparation of lactones via radical cyclization is shown in Scheme 4. In Scheme 4, $R_g$, $R_h$ and $R_i$ are aliphatic or aryl as defined herein.

Scheme 4

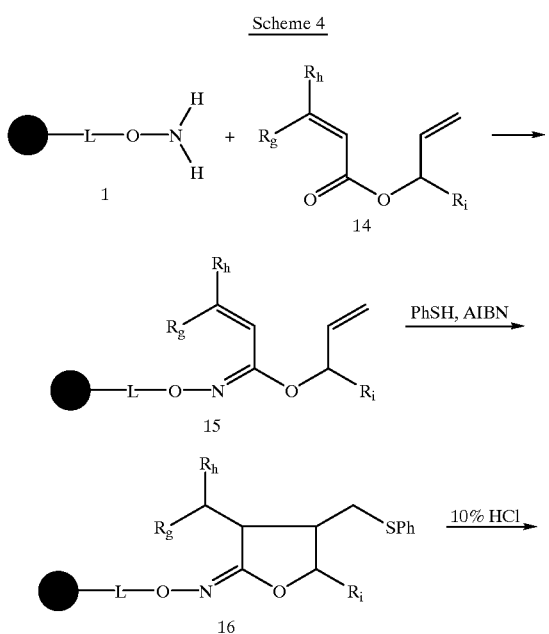

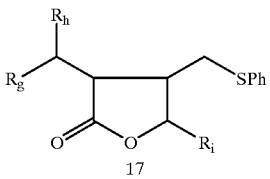

As shown in the foregoing Scheme 4, the polymeric hydroxylamine resin compound 1 is reacted with the $\alpha,\beta$ unsaturated carboxylic acid ester compound 14 to form the polymeric oximyl resin compound 15. Radical cyclization of 15, for example by heating in the presence of 2,2'-azobisisobutyronitrile (AIBN) and thiophenol in an inert organic solvent such as benzene results in formation of the polymeric g-lactone resin compound 16. Acid hydrolysis of 16, using, for example 10% aqueous HCl, provides the lactone 17. See O. Miyata et al., *Tet. Lett.*, 37, 229–232, (1996).

A process for the preparation of carbocyclic or heterocylic compounds by radical cyclization is shown in Scheme 5. In Scheme 5, $R_j$, $R_k$ and $R_l$ are aliphatic or aryl as defined herein. The methodology described in Scheme 1 is applicable to the preparation of 5-, 6- or 7-membered rings. Carbocycles result when the phenolic oxygen atom is replaced with a carbon atom.

Scheme 5

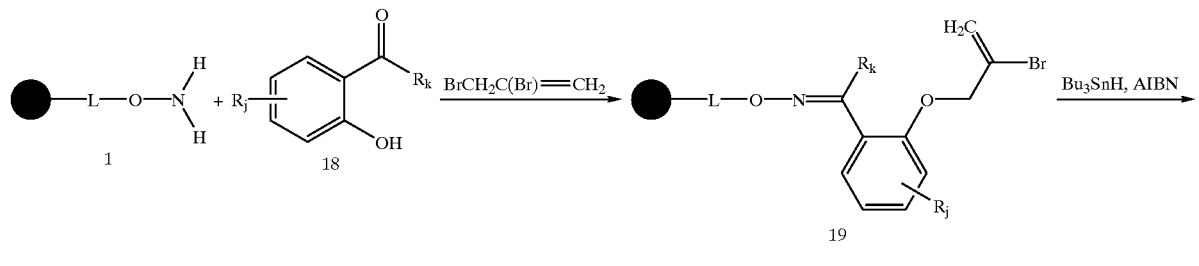

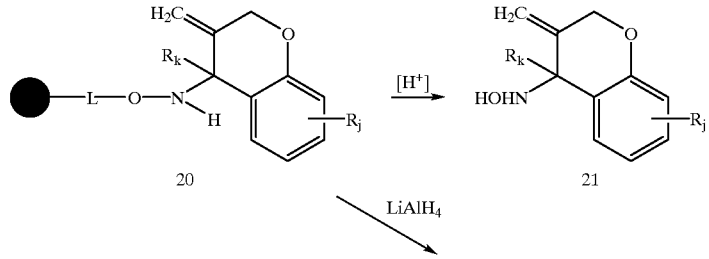

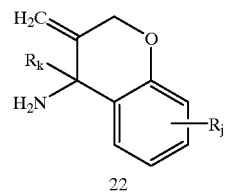

-continued

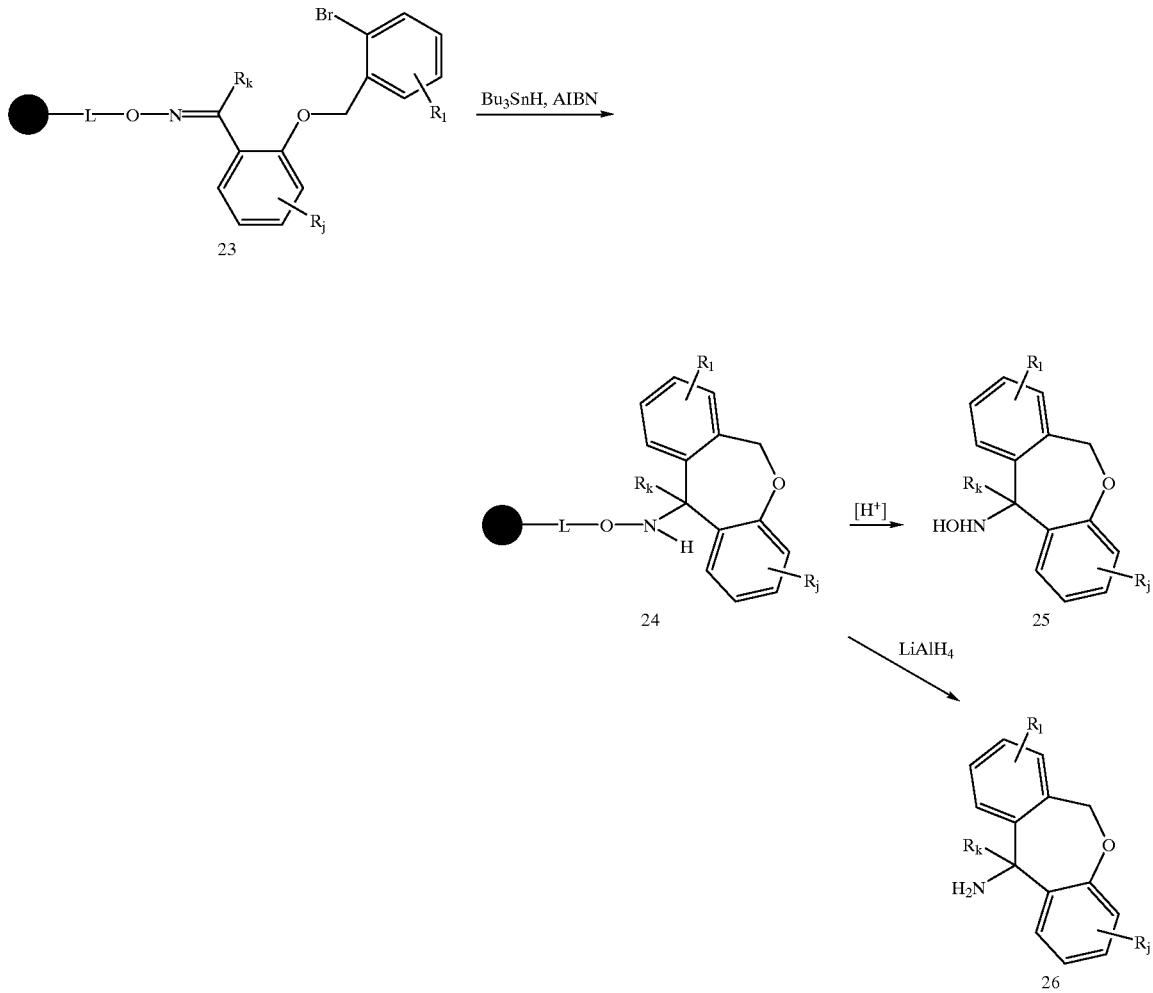

According to the foregoing Scheme 5, the polymeric hydroxylamine resin compound 1 is reacted with the acetophenone compound 18 and a bromoalkene compound or o-bromobenzyl compound to form the polymeric acetophenone oxime compounds 19 or 23. Radical cyclization of 19 or 23, for example by heating in the presence of AIBN and tri-n-butyltin hydride in an inert organic solvent such as benzene results in formation of the polymeric N-cyclyl hydroxylamine resin compounds 20 or 24. Treatment of 20 or 24 with acid, preferably trifluoroacetic acid, results in formation of the cyclic hydroxamic acid compounds 21 or 25. Reductive cleavage of 20 or 24, for example using $LiAlH_4$ as described in Scheme 3 above, results in formation of the cyclic amine compounds 22 or 26. See S. E. Booth et al., *J. Chem. Soc. Commun.*, 1248–1249, (1991).

Hydroxamic acid compounds of formula 29

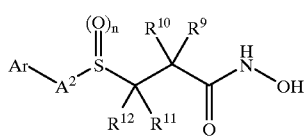

wherein Ar, $A^2$, $R^9$, $R^{10}$, $R^{11}$, $R^{12}$ and n are defined herein, are disclosed in WO 97/24117, incorporated herein by reference. Compounds of formula 29 inhibit the production or physiological effects of tumor necrosis factor (TNF) and are useful in treating a patient suffering from a pathological condition such as inflammation or autoimmune disease characterized by a physiologically detrimental excess of TNF.

A process for the preparation of a hydroxamic acid compound of formula 29, wherein Ar, $A^2$, $R^9$, $R^{10}$, $R^{11}$, $R^{12}$ and n are as defined above, according to this invention is shown in Scheme 6.

Scheme 6

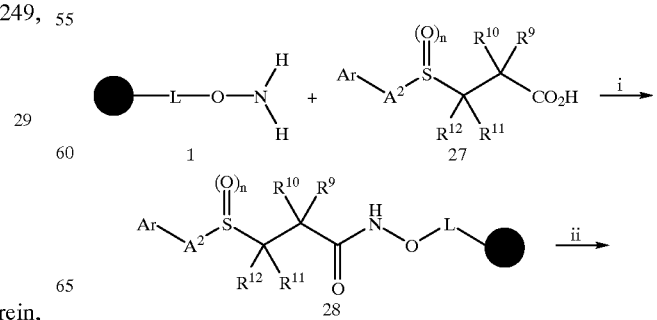

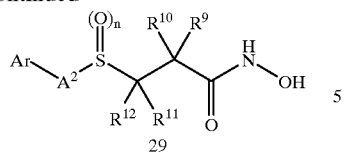

29

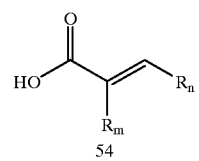

54 i) 3-(4-methyoxyphenylsulfonyl)propionic acid (5 equiv.); 1-(3-dimethylaminopropyl)-3-ethyl carbodiimide hydrochloride (EDCl 5 equiv.); DMF; 25° C.; 12-hours.

ii) 50% TFA in $CH_2Cl_2$ (100 equiv.); 30 minutes.

According to the foregoing Scheme 6, the carboxylic acid compound 27 is coupled to the polymeric hydroxylamine resin compound 1 as described in Scheme I above to form the polymeric hydroxamic acid resin compound 28. The polymeric hydroxamic acid resin compound 28 is then treated with an acid such as trifluoroacetic acid (TFA) in an inert solvent such as dichloromethane to liberate the hydroxamic acid compound 29. A higher percentage of TFA (trifluoroacetic acid) and longer reaction times are needed to cleave the hydroxamic acid from the Wang version compared to the Rink version of the resin. During the evaporation of the TFA in the work-up to isolate the hydroxamic acid, it is found that heating the sample during concentration would generate a significant amount of the N,O-diacylated dimer of the parent hydroxamic acid as a side-product. To minimize this side reaction the reaction mixture is concentrated at or below room temperature with toluene used as an azeotrope.

A process for the preparation of a polymeric α,β-unsaturated alkenoate resin compound 54 according to this invention is outlined in Scheme 7. In Scheme 7, $R_m$ is H or aliphatic, $R_n$ is aliphatic or aromatic, and $R_{20}$ and $R_{21}$ are alkyl. $R_m$ and $R_n$ may contain additional functional groups. It is understood that these functional groups may be suitably protected to prevent interference with the reactions described below.

Scheme 7

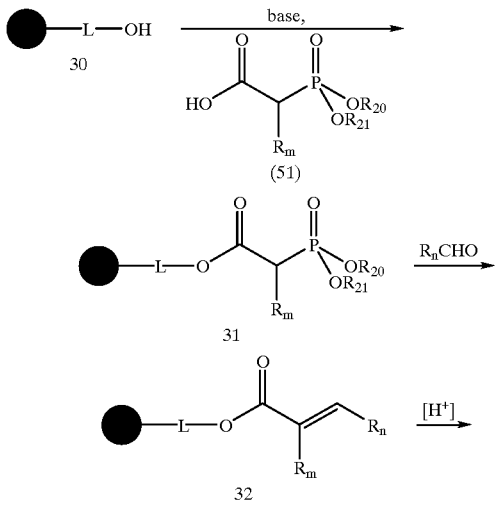

According to the foregoing Scheme 7, coupling of the polymeric hydroxy resin 30 with the phosphono acetic acid compound 51 provides the polymeric phosphonoacetoxy resin compound 31. The coupling is preferably accomplished using a preformed symmetric anhydride (method i below), or using the 2,6-dichlorobenzoic acid anhydride described by Sieber, P., *Tetrahedron Lett.*, 1987, 28, 6147–6150 (method ii below).

i) 51 (6 equiv.); diisopropylcarbodiimide (3 equiv.); dichloromethane; 0° C. 30 minutes, then 8, 4-dimethylaminopyridine (0.2 equiv.); 12 hours.

ii) 51 (3 equiv.); 2,6-dichlorobenzoyl chloride (3 equiv.); pyridine (6 equiv.); DMF; 12 hours.

The Horner-Emmons condensation of the polymeric phosphonoacetoxy resin compound 31 with the aldehyde $R_nCHO$ is then accomplished by treating 31 with an excess of a base such as potassium tert-butoxide, potassium bis(trimethylsilyl)amide or lithium bis(trimethylsilyl)amide in an organic solvent such as THF or toluene at about 0° C. to about 25° C. The mixture is stirred or shaken for a sufficient amount of time to quantitatively generate the resin-bound anion, generally from about 15 minutes to about 2 hours. The aldehyde $R_nCHO$ is then added and the mixture is stirred for up to three days to generate the polymeric alkenoate resin compound 32.

In an especially preferred preparation of the polymeric alkenoate resin compound 32, the polymeric phosphonoacetoxy resin compound 31 is treated with an excess of a base such as potassium tert-butoxide or lithium bis(trimethylsilyl)amide in an organic solvent such as THF at about 0° C. to about 25° C. The mixture is stirred or shaken for a sufficient amount of time to quantitatively generate the resin-bound anion, generally from about 15 minutes to about 2 hours. The solvent and excess base are then removed from the reaction vessel and a solution of the aldehyde in a less polar solvent mixture, comprising the solvent used in the generation of the resin-bound anion and a second, less polar solvent, is added at ambient temperature and the mixture is stirred for up to three days to generate the polymeric alkeneoate resin compound 32.

Preferred less polar solvents are alkanes such as pentane, hexane or heptane, or cycloalkanes such as cyclohexane, cyclopentane or cycloheptane. An especially preferred less polar solvent mixture is 60% cyclohexane-THF.

Use of the less polar solvent mixture in the Horner-Emmons condensation as described above presents a number of advantages over generation of the anion and condensation with the aldehyde using strong base in a polar solvent. A strong base is required to quantitatively generate the resin-bound anion. However, under the reaction conditions of strong base and a relatively polar solvent, the resin linkage was hydrolyzed resulting in a low yield of the polymeric alkeneoate resin compound 32. However, draining the solvent and excess base following essentially quantitative generation of the resin-bound anion and adding a solution of the aldehyde $R_nCHO$ in a less polar solvent mixture appears to stabilize the resin linkage toward hydrolysis and thereby results in unexpectedly high yields of the polymeric alkeneoate resin compound 32.

The polymeric alkeneoate resin compound 32 may be used for further transformations as described in Scheme 8, or the α,β-unsaturated acid compound 54 may be cleaved from the resin using methods commonly known in the art, for example by treating a mixture of the polymeric alkeneoate resin compound 53 in a suitable organic solvent such as dichloromethane, dichloroethane or dioxane, with acid. Cleavage is preferably accomplished at about ambient temperature using a trifluoroacetic acid (TFA)-dichloromethane solvent mixture over about 1 hour.

A process for the solid phase synthesis of the carboxylic acid compound 27, an intermediate useful for preparing the hydroxamic acid compound 29 in which Ar, $A^2$, n and $R^{11}$ are as defined herein and $R^9$, $R^{10}$ and $R^{12}$ are H, is shown in Scheme 8.

Scheme 8

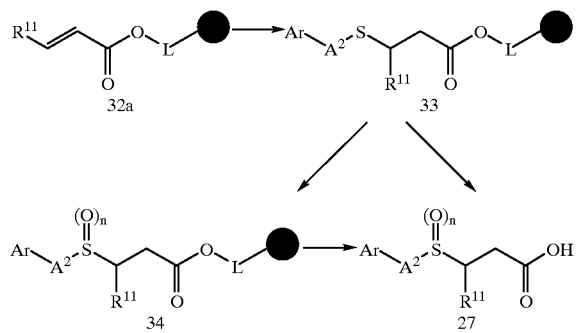

The polymeric diethylphosphonoacetoxy-resin compound 31 is treated with a base such as potassium bis(trimethylsilyl) amide in an inert solvent such as toluene, at a temperature of about 0° C., followed by an aldehyde of formula $R^{11}CHO$ wherein $R^{11}$ is as defined above, at about ambient temperature to give the polymeric alkenoate resin compound 32.

According to the foregoing Scheme 8, reaction of the polymeric alkenoate resin compound 32a, prepared as described in Scheme 7, with a thiol of formula Ar—$A^2$—SH, wherein Ar and $A^2$ are as defined above, provides the polymeric alkanoate resin compound 33. The addition may be conveniently carried out under mild basic conditions, for example in the presence of lithium hydroxide at about ambient temperature.

The polymeric alkanoate resin compound 33 may then be hydrolytically cleaved by treatment with acid as described in Scheme 7, above, to prepare the carboxylic acid compound 27 wherein n is 0.

Alternatively, the polymeric alkanoate resin compound 33 may be treated with an oxidizing agent such as m-chloroperbenzoic acid in an inert solvent such as dioxane at about ambient temperature to give the polymeric sulfoxide (n=1) or sulfone (n=2) resin compound 34. Acid hydrolysis of 34 as described in Scheme 7, above, provides the carboxylic acid compound 35.

The preparation of the polymeric hydroxylamine resin compound 1 is outlined in Scheme 9a.

Scheme 9a

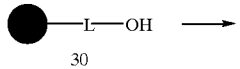

-continued

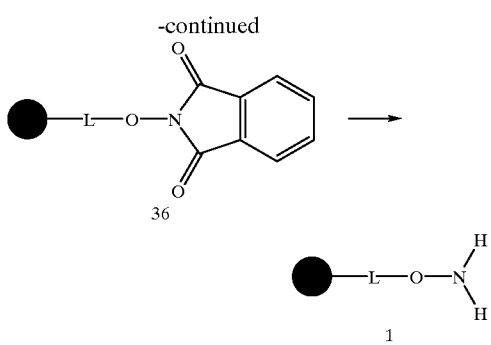

According to the foregoing Scheme 9a, a polymeric hydroxy resin compound 30 is converted to the polymeric N-hydroxylphthalimido resin compound 36 by coupling with N-hydroxyphthalimide under Mitsunobu conditions (Mitsunobu, O., *Synthesis* 1981, 1), by conversion of the hydroxy group to a leaving group such as the mesylate followed by nucleophilic displacement, or by reaction of the polymeric hydroxy resin compound with N-hydroxyphthalimide in the presence of an acid such as benzenesulfonic acid. Removal of the phthalimido group provides the polymeric hydroxylamine resin compound 1.

For example, when 30 is 4-(hydroxymethyl)phenoxymethyl-copoly(styrene-1%-divinylbenzene)-resin (Wang resin), N-hydroxyphthalimide is coupled to the resin in the presence of diisopropylazodicarboxylate and triphenylphosphine in DMF. The phthalimido protection is removed by methylaminolysis in THF at 40° C. The reaction is complete in about 2 hours. The use of the methylamine to cleave the phthalimide protection offers a significant advantage over the commonly used hydrazinolysis procedure (Wolf et al., *Can. J. Chem.*, 1970, 48, 3572.

When 4-(2',4'-dimethoxyphenyl-O-methylhydroxylamine)-phenoxymethyl-copoly(styrene-1%-divinylbenzene)-resin (Rink resin) is utilized, 1 is preferably prepared by reaction of the polymeric hydroxy resin compound with N-Hydroxy phthalimide in DMF in the presence of catalytic benzene sulfonic acid to form the polymeric N-hydroxyphthalimido resin compound 36. The phthalimido protecting group is then removed by reaction with hydrazine hydrate in tert-butanol at about 60° C. to give the corresponding polymeric hydroxylamine resin compound.

An alternative route to the polymeric N-protected hydroxylamine resin 6 is outlined in Scheme 9b.

Scheme 9b

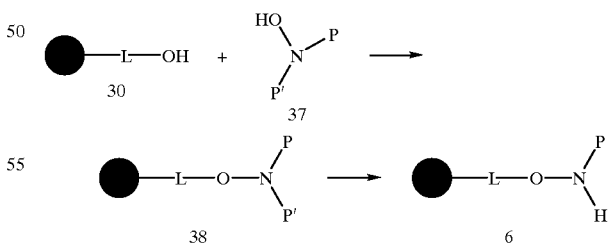

According to the foregoing Scheme 9, a polymeric hydroxy resin compound 30 is coupled with a N,N-diprotected hydroxylamine compound 37, wherein P and P' are amine protecting groups, as described in Scheme 8 above to form the polymeric N,N-diprotected hydroxylamine resin compound 38. The amine protecting group P' is then selectively removed to form the polymeric N-protected hydroxylamine resin compound 6.

In a preferred embodiment of the synthesis described in Scheme 9, P is benzyl and P' is allyloxycarbonyl. Selective removal of the allyloxycarbonyl protecting group is effected by treatment with tetrakis(triphenylphosphine)Palladium(0).

The N,N-diprotected hydroxylamine compound 37 is prepared by sequential introduction of the protecting groups P and P' to an O-protected hydroxylamine compound of formula $H_2NOP^2$ wherein $P^2$ is a hydroxy protecting group. A preferred hydroxy protecting group is alkyl. The amine protecting groups P and P' are then introduced using reagents and reaction conditions well known in the art of organic synthesis. For Example, reaction of O-tert-butylhydroxylamine with allyloxychloroformate results in formation of N-allyloxycarbonyl-O-tert-butylhydroxylamine, which is then reacted with benzyl bromide to form N-benzyl-N-allyloxycarbonyl-O-tert-butylhydroxylamine. Treatment of N-benzyl-N-allyloxycarbonyl-O-tert-butylhydroxylamine with trifluoroacetic acid gives N-benzyl-N-allyloxycarbonylhydroxylamine.

The preparation of a polymeric 4-(methyl-O-methylhydroxylamine)-2-fluorophenoxymethyl resin compound is shown in Scheme 10.

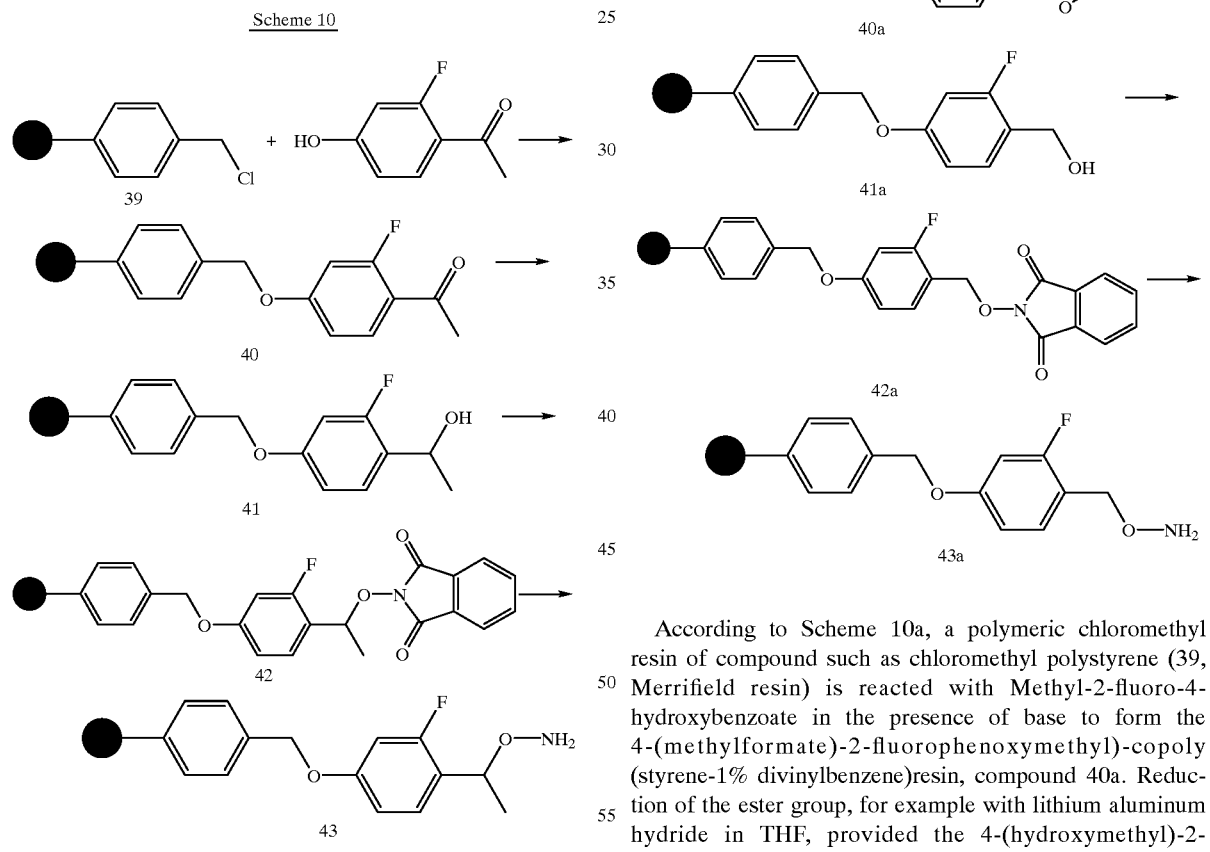

According to the foregoing Scheme 10, a polymeric chloromethyl resin compound such as chloromethyl polystyrene (39, Merrifield resin) is reacted with 4-hydroxy-2-fluoroacetophenone in the presence of base to form the 4-(1-hydroxyethyl)-2-fluorophenoxymethyl resin compound 40. Reduction of the ketone group, for example using lithium borohydride in THF, provides the 4-(1-hydroxyethyl-2-fluorophenoxymethyl resin compound 41. Conversion of 41 to the hydroxyphthalimido resin compound 42, followed by removal of the phthalimido group as described in Scheme 8 above, provides the 4-(methyl-O-methylhydroxylamine)-2-fluorophenoxymethyl-copoly (styrene-1% divinylbenzene)resin compound 43.

Similarly, the preparation of a polymeric 4-(O-methylhydroxylamine)-2-fluorophenoxymethyl resin compound is shown in Scheme 10a.

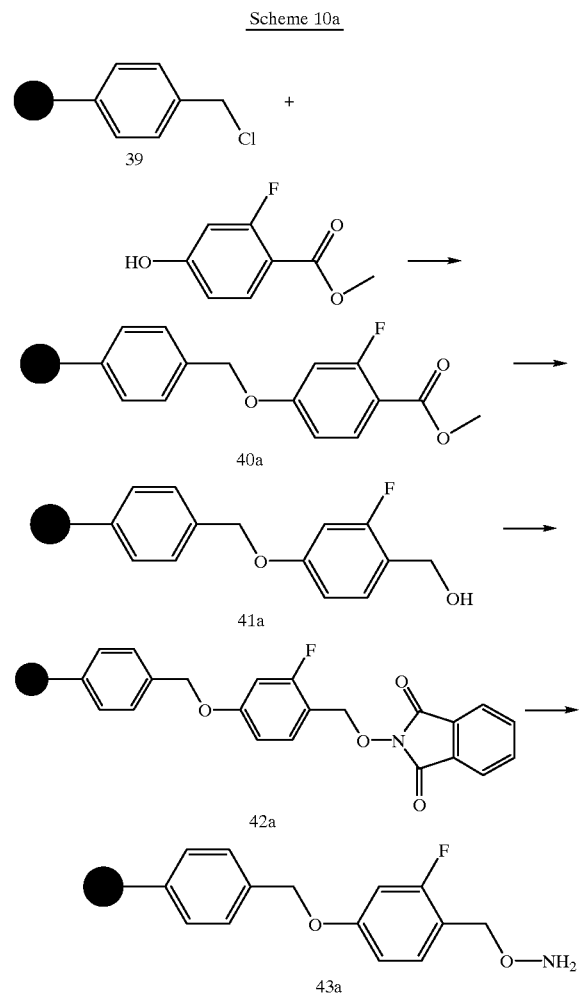

According to Scheme 10a, a polymeric chloromethyl resin of compound such as chloromethyl polystyrene (39, Merrifield resin) is reacted with Methyl-2-fluoro-4-hydroxybenzoate in the presence of base to form the 4-(methylformate)-2-fluorophenoxymethyl)-copoly (styrene-1% divinylbenzene)resin, compound 40a. Reduction of the ester group, for example with lithium aluminum hydride in THF, provided the 4-(hydroxymethyl)-2-fluorophenoxymethyl)-copoly(styrene-1% divinylbenzene) resin, compound 41a. Conversion of this to the hydroxylphthalimido resin compound 42a, followed by removal of the phthalimido group as described in Scheme 8 above, provides the 4-(O-methylhydroxylamine))-2-fluorophenoxymethyl)-copoly(styrene-1% divinylbenzene) resin, compound 43a.

The preparation of a polymeric 4-(O-methylhydroxylamine)-fluorophenoxymethyl resin compound is shown in Scheme 11.

Scheme 11

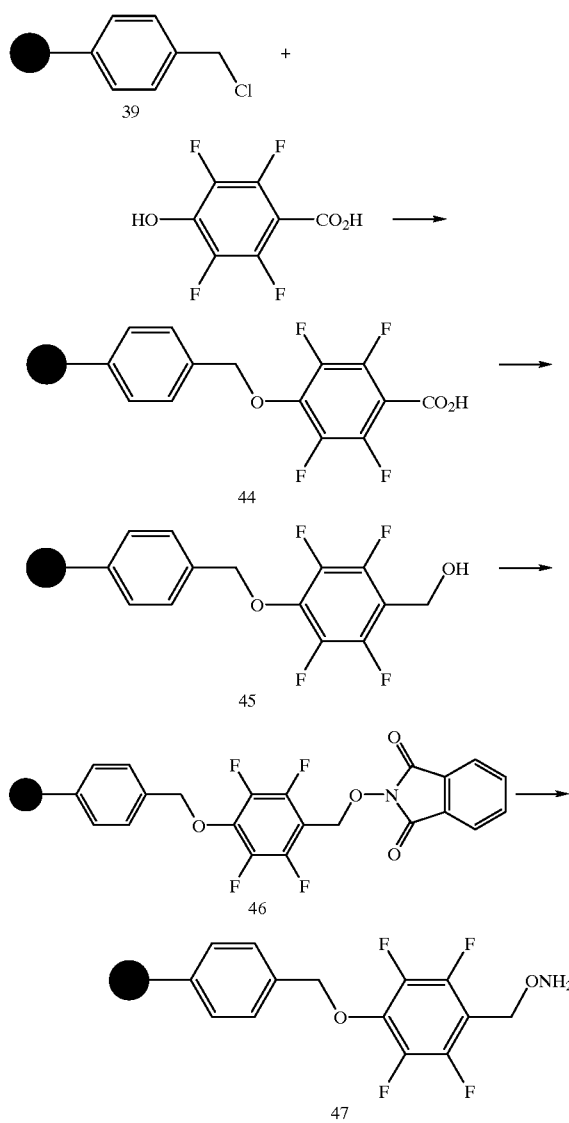

Scheme 12

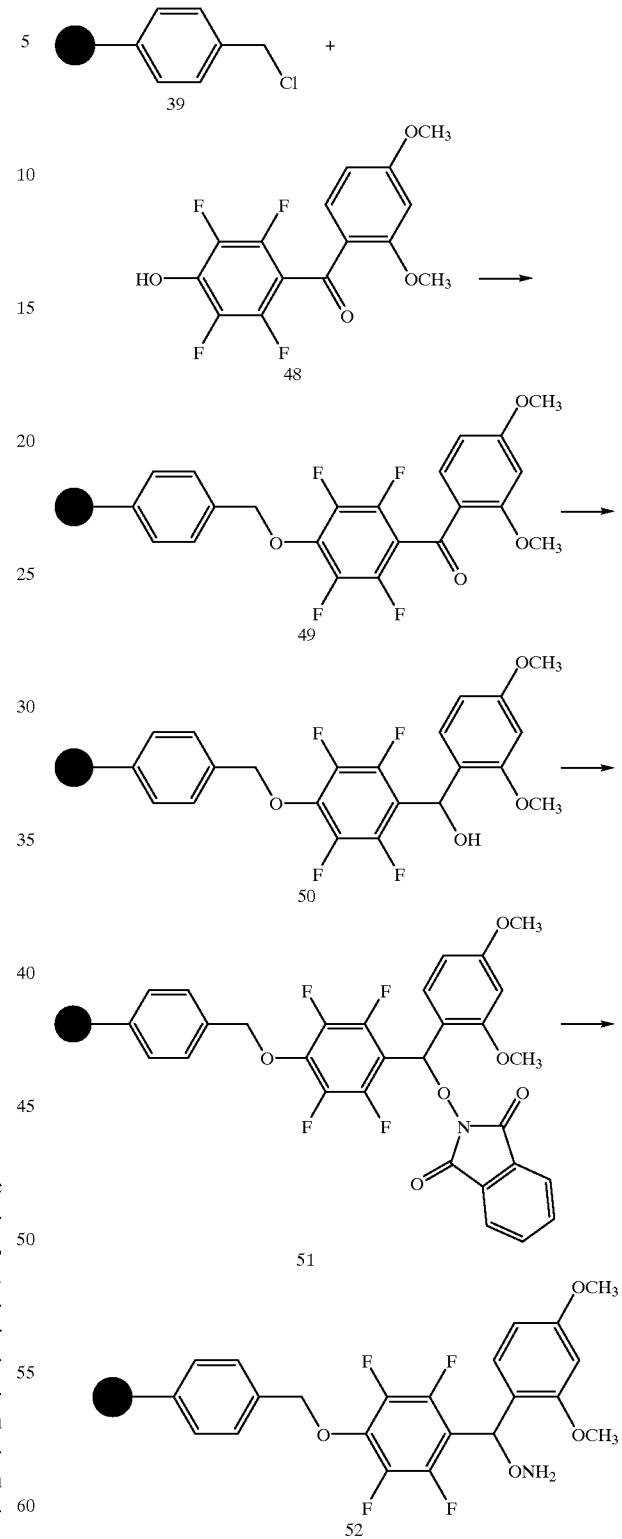

According to the foregoing Scheme 11, a polymeric chloromethyl resin compound such as chloromethyl polystyrene (39, Merrifield resin) is reacted with 4-hydroxy-2,3,5,6-tetrafluorobenzoic acid in the presence of base to form the 4-carboxy-2,3,5,6-tetrafluorophenoxymethyl resin compound 44. Reduction of the carboxylic acid group, for example using LiAlH$_4$, diisobutylaluminum hydride, or BH$_3$-THF provides the 4-hydroxymethyl-2,3,5,6-tetrafluorophenoxymethyl resin compound 45. Conversion of 45 to the hydroxyphthalimido resin compound 46, followed by removal of the phthalimido group as described in Scheme 8 above provides the 4-(O-methylhydroxylamine)-2,3,5,6-tetrafluorophenoxymethyl-copoly(styrene-1%-divinylbenzene)resin compound 47.

The preparation of a polymeric 4-(2',4'-dimethoxyphenyl-O-methylhydroxylamine)-2,3,5,6-tetrafluorophenoxymethyl resin compound is shown in Scheme 12.

According to the foregoing Scheme 12, a polymeric chloromethyl resin compound is reacted with 4-phenoxy-2,3-5,6-tetrafluorophenyl 2,4-dimethoxyphenyl ketone 48 in the presence of base as described in Scheme 11 above to form the 4-(2',4'-dimethoxyphenylcarbonyl)-2,3,5,6- tetrafluorophenoxymethyl-resin compound 49. Reduction of the carbonyl, for example using LiBH$_4$, provides the 4-(hydroxymethyl-2',4'-dimethoxyphenyl)-2,3,5,6-tetrafluorophenoxymethyl resin compound 50. Conversion of 50 to the hydroxyphthalimido resin compound 51, followed by removal of the phthalimido group as described in Scheme 8 above provides the 4-(2',4'-dimethoxyphenyl-O-methylhydroxylamine)-2,3,4,5,6-tetrafluorophenoxymethyl-resin compound 52.

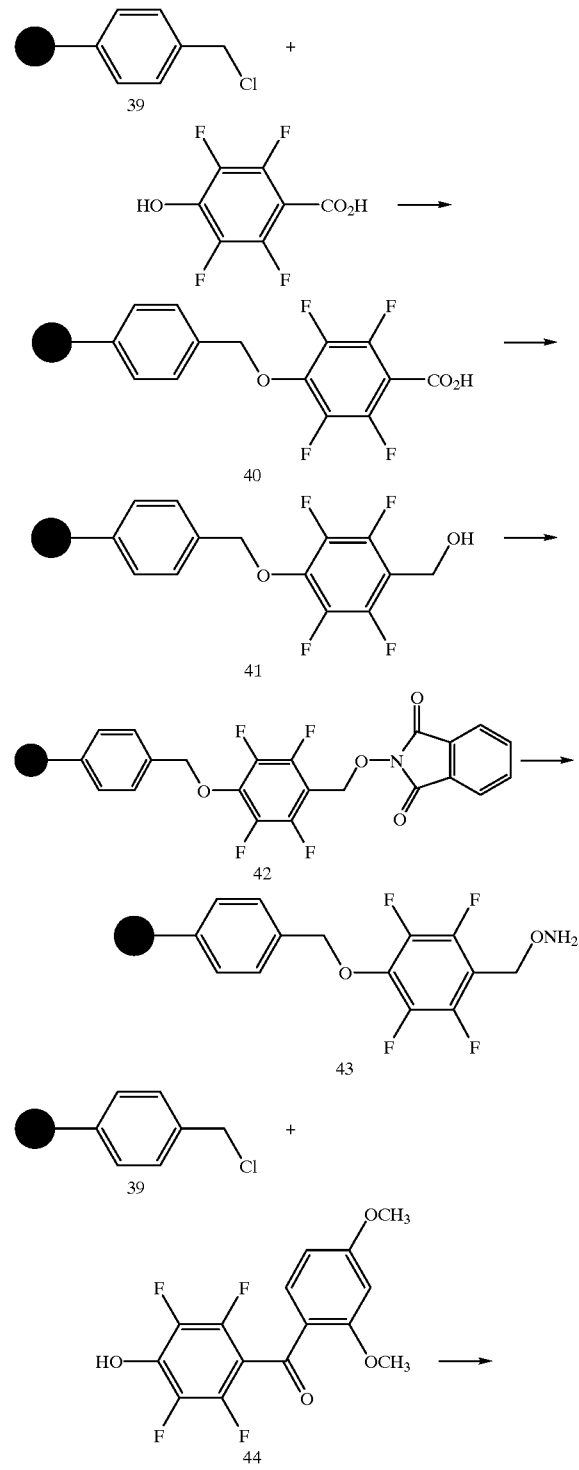

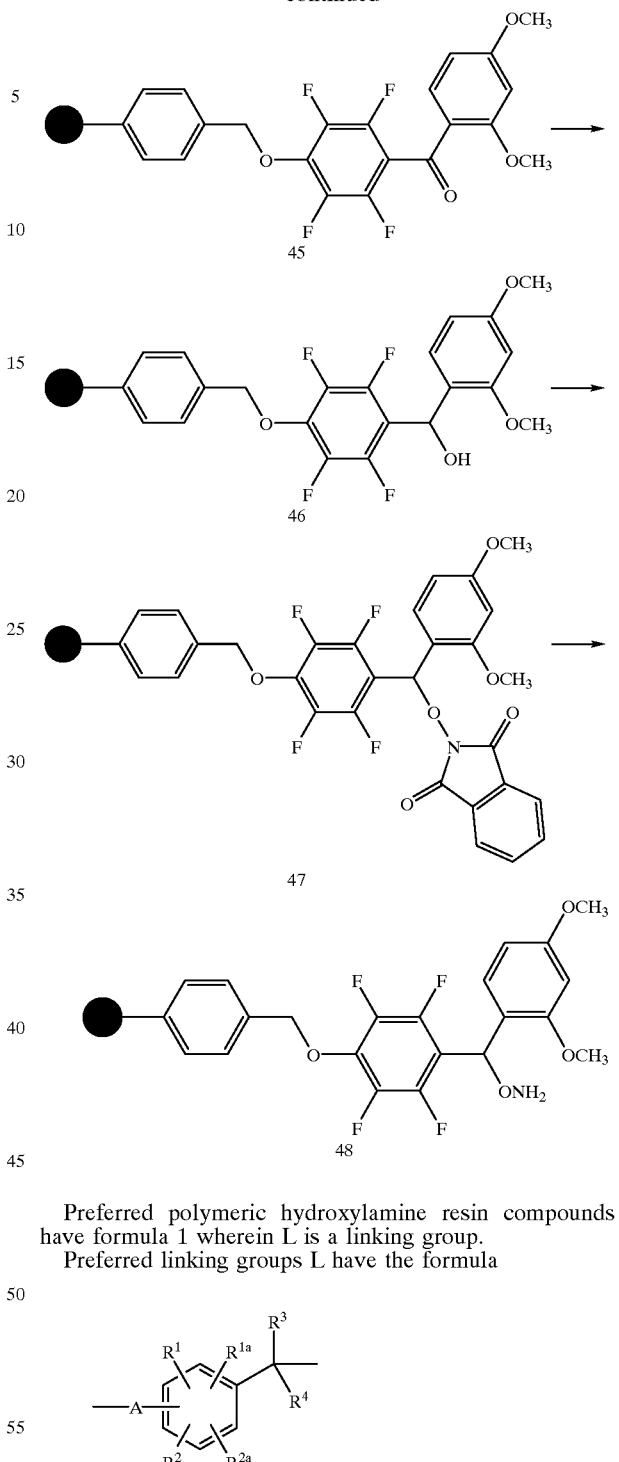

Preferred polymeric hydroxylamine resin compounds have formula 1 wherein L is a linking group.
Preferred linking groups L have the formula

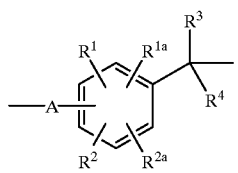

wherein
A is absent or a group of formula —X$^1$—Z— wherein
X$^1$ is —CHR— or —CHR—Y—CO—(CH$_2$)$_n$—
wherein R is H, alkyl, phenyl, or phenyl substituted with —H, alkyl, alkoxy, halogen, nitrile or —NO$_2$,
Y is —O— or —NH—,
n is an integer from 1 to 6, and
Z is —O— or —NH—;
R$^1$, R$^{1a}$, R$^2$, and R$^{2a}$ are independently ring system substituents; and R³ and R⁴ are independently —H, alkyl, phenyl, or phenyl substituted with one or more substituents selected from alkyl, alkoxy, halogen nitrile and —NO₂;

or one of R¹ and R² taken together with one of R³ and R⁴ and the carbon atoms to which they are attached define a linking group of formula

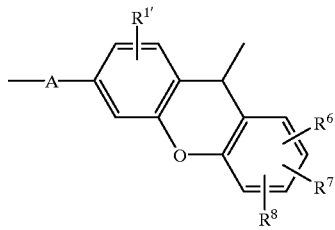

wherein
R¹' is —H, alkyl, alkoxy, halogen, nitrile or —NO₂; and
R⁶, R⁷ and R⁸ are independently selected from —H, alkyl, alkoxy, halogen, nitrile and —NO₂.

More preferred linking groups have formula

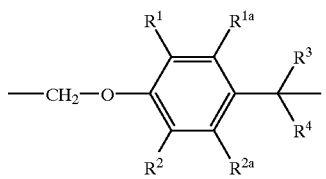

wherein
R¹ and R² are independently H or F;
R¹ᵃ and R²ᵃ are independently ring system substituents; and
one of R³ and R⁴ is H and the other is H or 2,4-dimethoxyphenyl.

Representative preferred polymeric hydroxylamine resin compounds include 4-(O-methylhydroxylamine) phenoxymethyl-copoly(styrene-1% divinylbenzene)resin, designated herein as

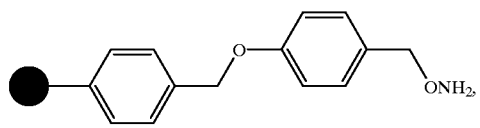

4-[4-(O-methylhydroxylamine)-3-methoxyphenoxy]-(N-4-methylbenzhydryl)-butyramide-copoly(styrene-1%-divinylbenzene)-resin, designated herein as

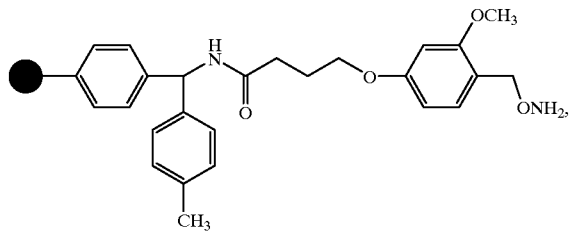

4-(2',4'-dimethoxyphenyl-O-methylhydroxylamine)-phenoxymethyl-copoly(styrene-1% divinylbenzene) resin, designated herein as

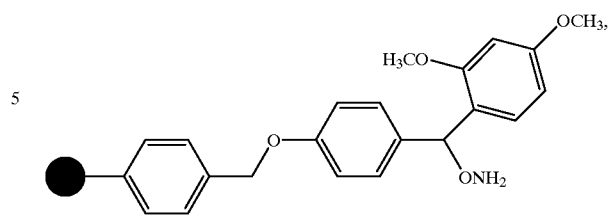

4-[4-(1-aminoxyethyl)-2-methoxy-5-nitrophenoxy]-(N-4-methylbenzhydryl)-butyramide-copoly(styrene-1% divinylbenzene)resin, designated herein as

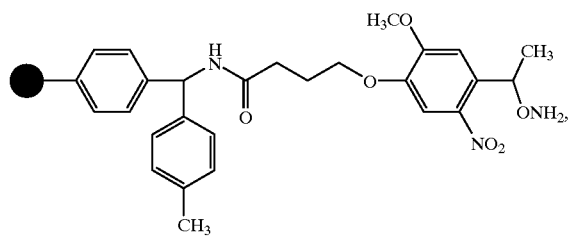

O-hydroxylamine-2'-chlorotrityl-copolystyrene-1%-divinylbenzene-resin, designated herein as

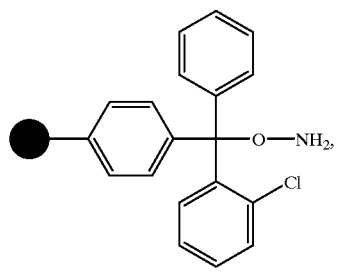

O-hydroxylamine-trityl-copolystyrene-1%-divinylbenzene-resin, designated herein as

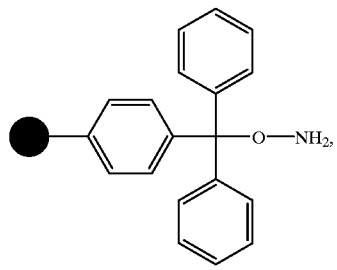

5-(4-O-methylhydroxylamine-3,5-dimethoxyphenoxy)-valeric acid-copolystyrene-1%-divinyl benzene resin, designated herein as

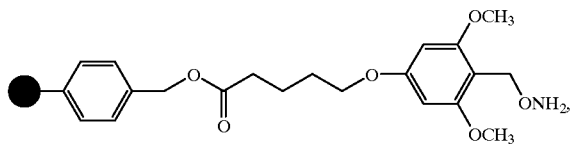

4-O-methylhydroxylamine-3-methoxyphenoxy-copolystyrene-1%-divinyl benzene resin, designated herein as

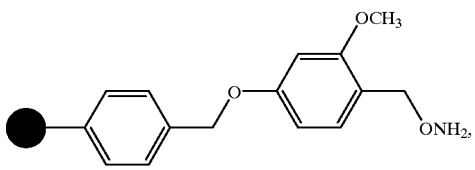

3-hydroxy-xanthydroxylamine-copolystryene-1%-divinylbenzene resin, designated herein as

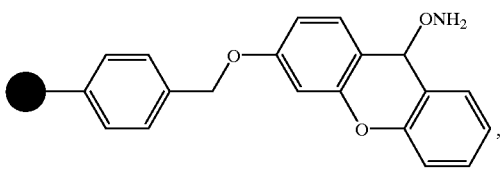

4-(O-methylhydroxylamine)-2,3,5,6-tetrafluorophenoxymethyl-copoly(styrene-1% divinylbenzene) resin, designated herein as

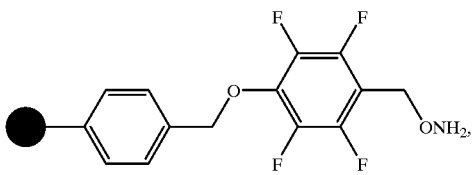

4-(1-methyl-1-one)-3-fluorophenoxymethyl-copoly(styrene-1% divinylbenzene)resin, designated herein as

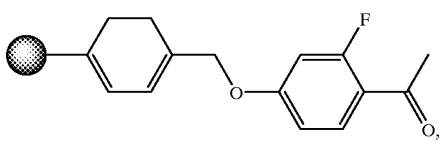

4-(1-methyl-1-hydroxylamine)-3-fluorophenoxymethyl-copoly(styrene-1% divinylbenzene)resin, designated herein as,

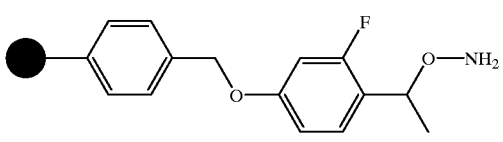

4-(1-methyl-1-hydroxy-)-3-fluorophenoxymethyl-copoly(styrene-1% divinylbenzene)resin, designated herein as

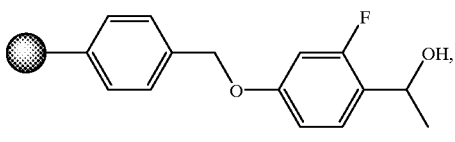

4-(carboxy)-3-fluorophenoxymethyl-copoly(styrene-1% divinylbenzene)resin, designated herein as

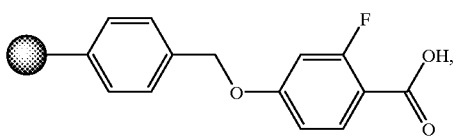

4-(carboxyaldehyde)-3-fluorophenoxymethyl-copoly(styrene-1% divinylbenzene)resin, designated herein as

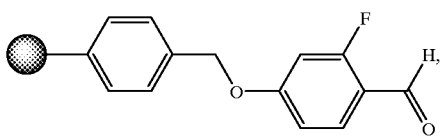

4-(methylalcohol)-3-fluorophenoxymethyl-copoly(styrene-1% divinylbenzene)resin, designated herein as

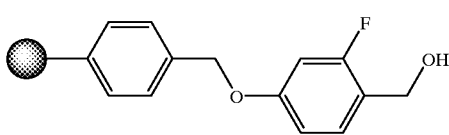

and
4-(2',4'-dimethoxyphenyl-O-methylhydroxylamine)-2,3,5,6-tetrafluorophenoxymethyl-copoly(styrene-1% divinylbenzene)resin, designated herein as

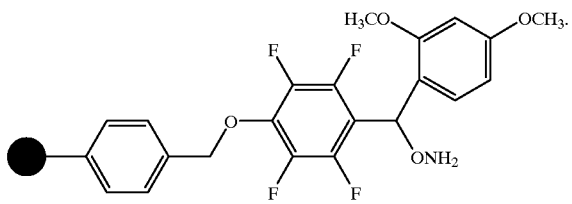

The most preferred polymeric hydroxylamine resin compounds are 4-(O-methylhydroxylamine)-2,3,5,6-tetrafluorophenoxymethyl-copoly(styrene-1% divinylbenzene)resin, 4-(2',4'-dimethoxyphenyl-O-methylhydroxylamine)-2,3,5,6-tetrafluorophenoxymethyl-copoly(styrene-1% divinylbenzene)resin, 4-(O-methylhydroxylamine)phenoxymethyl-copoly(styrene-1% divinylbenzene)resin, 4-(1-methyl-1-one-)-3-fluorophenoxymethyl-copoly(styrene-1% divinylbenzene) resin, 4-(1-methyl-1-hydroxylamine)-2-fluorophenoxymethyl-copoly(styrene-1% divinylbenzene) resin, 4-(1-methyl-1-hydroxy-)-3-fluorophenoxymethyl-copoly(styrene-1% divinylbenzene)resin, 4-(carboxy)-3-fluorophenoxymethyl-copoly(styrene-1% divinylbenzene) resin, 4-(O-methylhydroxylamine)phenoxymethyl-copoly(styrene-1% divinylbenzene)resin, 4-(carboxyaldehyde)-3-fluorophenoxymethyl-copoly(styrene-1% divinylbenzene) resin, and 4-(2',4'-dimethoxyphenyl-O-methylhydroxylamine)-phenoxymethyl-copoly(styrene-1% divinylbenzene)resin.

The Rink handle (H. Rink, *Tet. Lett.*, 28, 3787–3790, 1987) has the advantage of being cleaved under mild acidolysis for short periods of time (i.e. 10% TFA in DCM for 10–15 minutes.). However, due to the cost of the resin it is desirable to synthesize the corresponding functional resin on the Wang solid support ((a) S. S. Wang, *J. Am. Chem. Soc.*, 1973, 95, 1328. b) Lu et al., *J. Org Chem.*, 1981, 46, 3433).

The polymeric hydroxylamine resin compounds in which $R_{1a}$ and $R_{1b}$ are F are especially useful as it lends itself to ready quantification of resin loading and monitoring of reactions conducted on the resin using fluorine NMR.

The methods described herein are also useful for the preparation of peptide aldehydes, ketones and hydroxamic acids. In general, this method involves coupling the carboxyl group of a suitably N-protected first amino acid to the resin to form the polymeric N-protected amino acid hydroxamic acid resin compound. The amino acid N-protecting group is then removed and the unprotected polymeric amino acid hydroxamic acid resin compound is coupled with a second suitably N-protected amino acid. This process is then repeated until the desired amino acid residues have been incorporated in the peptide.

Alternatively, peptides comprising multiple amino acids are prepared by coupling a suitably N-protected peptide subunit comprising two or more amino acids to form the polymeric N-protected peptide hydroxamic acid resin compound. The amino acid N-protecting group is then removed and the unprotected polymeric peptide hydroxamic acid resin compound is coupled with a second suitably N-protected amino acid or peptide. Thus, in addition to the sequential addition of individual amino acid subunits described above, a polypeptide may be prepared by coupling of peptide subunits.

Once the desired amino acids have been incorporated into the peptide, the polymeric peptide hydroxamic acid compound is reacted with an organometallic reagent followed by acid hydrolysis to form the peptide ketone compound; reductively cleaved to form the peptide aldehyde compound; or cleaved with acid to form the peptide hydroxamic acid compound. Any remaining protecting groups ay be removed prior to or subsequently to cleavage of the peptide from the resin.

stable to the conditions of coupling to the polymeric hydroxylamine resin compound while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, (a,a)dimethyl-3,5-dimethoxybenzyloxycarbonyl, o-nitrophenylsulfenyl, 2-cyano-t-butyloxycarbonyl, and the like.

Additionally, the resins of this invention are useful for constructing arrays of aldehyde, ketone or amine combinatorial libraries or arrays of aldehydes and ketones as reagents in combinatorial library synthesis, for example, reagents for the Ugi 4-component condensation (Ivar Ugi, in Isonitrile Chemistry, 1971, p. 145, Academic Press). The hydroxylamine bound resins may be used not only for single functional group transformations, but also multiple step solid phase synthesis to generate combinatorial libraries.

The functionalized resins of this invention also are useful for the parallel synthesis of a multiplicity of different aldehyde, ketone or amine end products as outlined for ketone compounds in Schemes 12a and 12b. In Schemes 12a and 12b, $R_b$ and $R_c$ are as defined above; n is an integer which represents the total number of different aldehyde, ketone or amine products which are to be prepared; and $R_{a1}$–$R_{an}$ represent, independently, an aliphatic or aromatic group as defined herein.

Scheme 13a

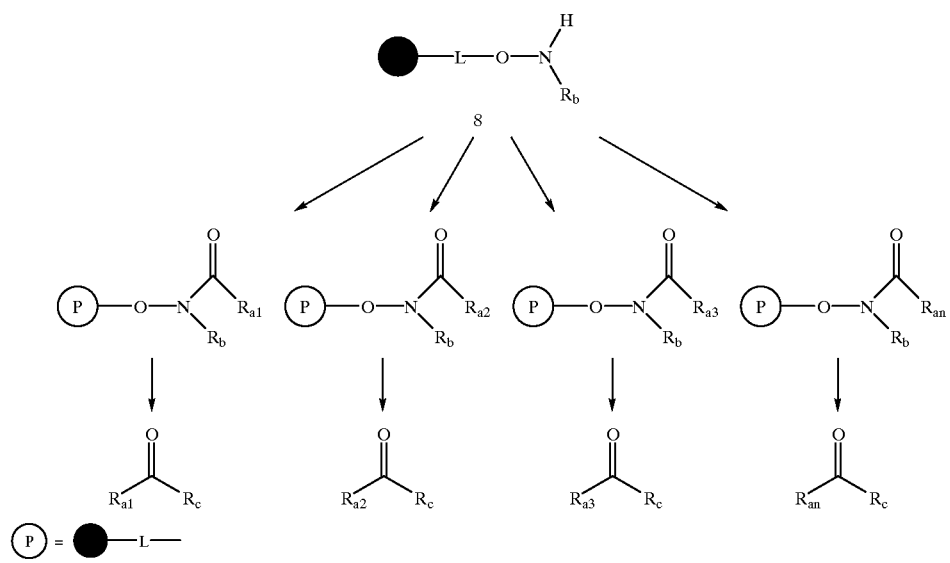

Hydroxamic acid derivatives produced in accordance with the process of this invention are useful, inter alia, as 5-LO (lipoxygenase) inhibitors. See, e.g., A. O. Stewart et al., Structure-Activity Relationships of N-Hydroxyurea 5-Lipoxygenase Inhibitors, J. Med. Chem. 1997, 40. 1955–1968.

N-protecting groups suitable for use in peptide synthesis as described herein should have the properties of being The parallel synthesis of a multiplicity of ketone compounds using a multiplicity of carboxylic acid compound $R_{a1}CO_2H$—$F_{an}CO_2H$ and a single organometallic compounds $R_cMgX$ is shown in Scheme 13a. According to Scheme 13a, the N-alkylated hydroxylamine resin compound 8, prepared as described in Scheme 2, is divided into n portions. Each portion of resin is then coupled with a different carboxylic acid compound to give n portions of polymeric N-alkylated hydroxamic acid resin compound. Each portion of polymeric N-alkylated hydroxamic acid resin compound is then reacted with a Grignard reagent of formula $R_cX$ and subjected to acid hydrolysis to give n portions of ketone derived from a single organometallic reagent.

Scheme 13b

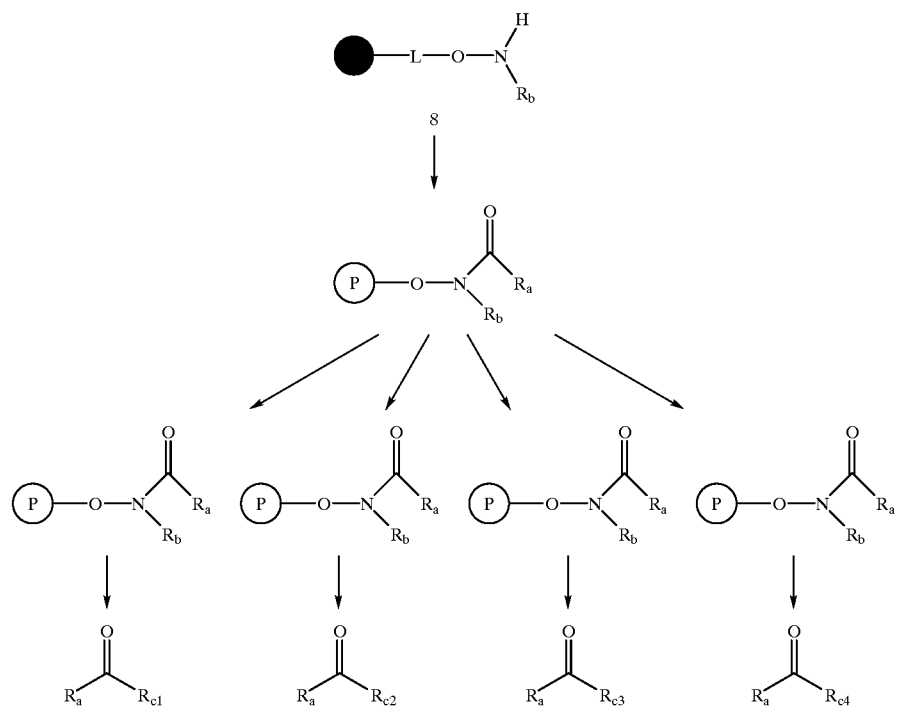

The parallel synthesis of n different ketone compounds derived from a single carboxylic acid compound $R_aCO_2H$ and n different organometallic compounds $R_{c1}MgBr$ to $R_{cn}MgBr$ is outlined in Scheme 13b above. According to Scheme 13b, the polymeric N-alkylated hydroxylamine resin compound is coupled with a carboxylic acid of formula $R_aCO_2H$. The resulting polymeric N-alkylated hydroxamic acid resin compound is then divided into n portions, and each portion of polymeric N-alkylated hydroxamic acid resin compound is then reacted with a different Grignard reagent $R_{c1}$–$R_{cn}MgBr$ and subjected to acid hydrolysis to give n different ketone compounds derived from a single carboxylic acid compound.

The functionalized resins of this invention are also useful for constructing a combinatorial library of ketones or amines as illustrated for the ketone library derived from 4 carboxylic acid compounds and 4 Grignard reagents as outlined in Scheme 14.

Scheme 14

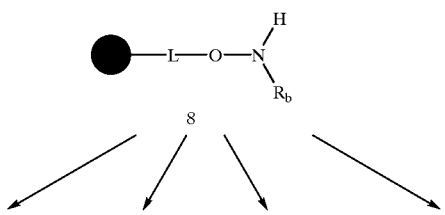

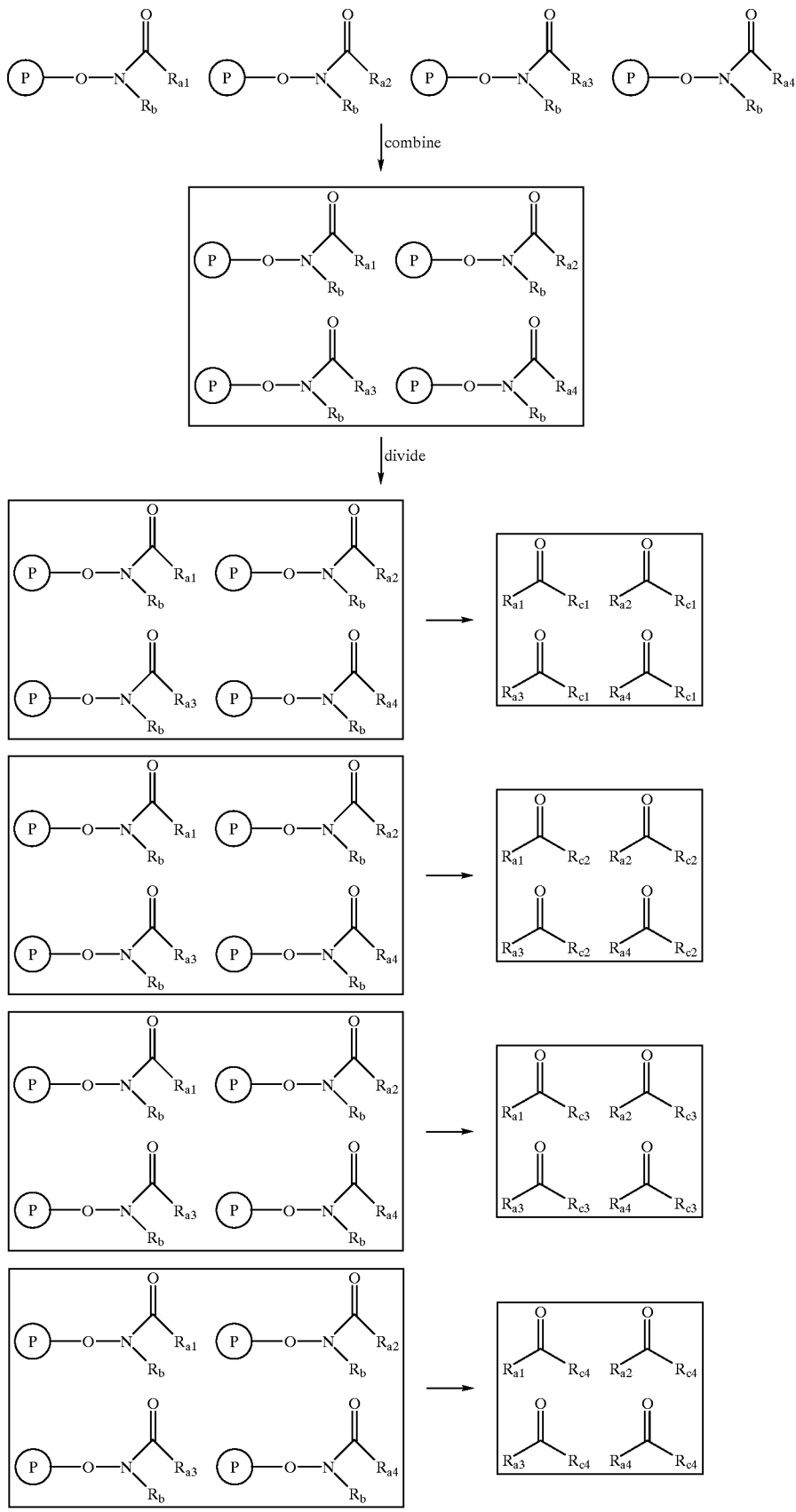

According to the foregoing Scheme 14, the polymeric N-alkylated hydroxylamine resin compound 8 is divided in 4-portions, and each portion is coupled with a different carboxylic acid compound to prepare 4 different polymeric N-alkylated hydroxamic acid resin compounds. The 4 portions of polymeric N-alkylated hydroxamic acid resin compounds are then mixed together to form a single portion which is then divided into 4 portions of polymeric N-alkylated hydroxamic acid resin compounds, in which each portion contains approximately equal amounts of each individual polymeric N-alkylated hydroxamic acid resin compound. Each of the 4 portions is then reacted with a different Grignard reagent $R_{c1}$–$R_{c4}$MgBr and subjected to acid hydrolysis to give 4 portions of ketone compound, each of which contains 4 compounds representing the products of reaction of each of the 4 different polymeric N-alkylated hydroxamic acid resin compounds with a single Grignard reagent. In this manner a combinatorial library containing a multiplicity of ketone compounds may be quickly constructed.

In a similar manner, a combinatorial library of peptides may be assembled by repeating the dividing-recombining sequence for each amino acid or peptide building block.

(10×25 mL). The resin is then dried overnight under high vacuum at 40° C. The IR spectrum shows a carbonyl absorbance at 1733 cm$^{-1}$ corresponding to the phthalimido carbonyl stretch. Elemental analysis: calcd.:0.28% N. Found: 0.26% N. Loading=0.18 mmol/g.

The resin is swelled in 20 mL of tert-butanol for ten minutes. Hydrazine hydrate (10 mL) is added to the mixture and the reaction is warmed to 60° C. with mechanical stirring for 12 hours, after which the reaction is cooled to ambient temperature. The resin is filtered and washed extensively with DMF (10×25 mL), THF (10×25 mL), and diethyl ether (10×25 mL), then dried under high vacuum at 40° C. overnight. The IR spectrum of the resulting resin shows the loss of the carbonyl stretch at 1733 cm$^{-1}$ which is present in the starting material. Elemental Analysis: % N found=0.43; 0.42 (corresponding to a loading level of 0.3 mmol/g).

EXAMPLE 2

N-[3-((4-methoxyphenyl)sulfonyl)prop-1-ylcarbonyl]4-(2',4'-dimethoxyphenyl-O-methylhydroxylamine)-phenoxymethyl-copoly(styrene-1% divinylbenzene)resin

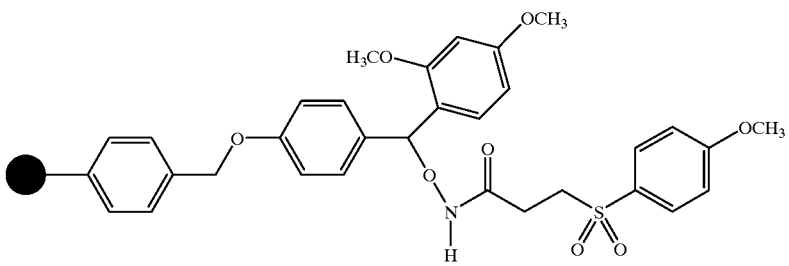

The foregoing may be better understood by reference to the following Examples, which are presented for illustration and not intended to limit the scope of the invention.

EXAMPLE 1

4-(2',4'-Dimethoxyphenyl-O-methylhydroxylamine)-phenoxymethyl-copoly(styrene-1% divinylbenzene) resin

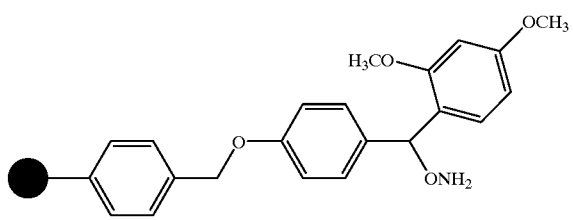

Rink acid resin (1 g; 0.63 mmol) is swelled in DMF (10 mL) for 15 minutes at ambient temperature. N-Hydroxyphthalimide (514 mg; 3.15 mmol) is added to the resin suspension followed by benzene sulfonic acid (19 mg; 0.13 mmol). The mixture is stirred by means of a mechanical stirrer and heated to 50° C. for five hours. The mixture is then cooled to ambient temperature and stirred for an additional 12 hours, after which the resin is filtered and washed extensively with DMF (5×25 mL); DMF:H$_2$O (70:30; 5×25 mL); THF (10×25 mL); and diethyl ether 4-(2',4'-dimethoxyphenyl-O-methylhydroxylamine)-phenoxymethyl-copoly(styrene-1% divinylbenzene)resin (200 mg) is swelled in DMF (3 mL). To this suspension is added 3-(4-methoxyphenylsulfonyl)propionic acid (610 mg; 2.5 mmol) and 1-(3-dimethylaminopropyl)-3-ethyl carbodilmide hydrochloride (EDCI; 477 mg; 2.5 mmol) at ambient temperature. The reaction mixture is shaken at ambient temperature using a vortex shaker for 12 h, after which the resin is filtered and washed extensively with DMF:H$_2$O (80:20; 5×5 mL), DMF (5×5 mL), THF (5×5 mL), and diethyl ether (5×5 mL). The resin is dried under high vacuum at 40° C. for 12 hours. The IR spectrum shows a carbonyl absorbance at 1675 cm$^{-1}$ corresponding to the bound hydroxamate.

EXAMPLE 3

N-hydroxy-3-(4-methoxyphenylsulfonyl) propionamide

Dry N-[3-((4-methoxyphenyl)sulfonyl)prop-1-ylcarbonyl]4-(2',4'-dimethoxyphenyl-O-methylhydroxylamine)-phenoxymethyl-copoly(styrene-1% divinylbenzene)resin (200 mg), prepared as in Example 2, is swelled in 3 mL of methylene chloride for 10 minutes. Trifluoroacetic acid (TFA; 0.3 mL) is added to the mixture dropwise at ambient temperature and the resulting mixture is vortexed for 30 minutes. The resin turned a dark blue upon addition of the TIFA. The mixture is then filtered and washed with two 5 mL portions of methylene chloride. The filtrate is evaporated by rotary evaporation to yield 20 mg of crude product. An LC/MS trace of the crude reaction mixture showed it to contain better than 75 area % of the desired product, 3-(4-methoxyphenylsulfonyl)propionic acid is present in 6 area %). $^1$H NMR (MeOH-$d_4$) δ 62.45 (t, 2H); 3.45 (t, 2H); 3.90 (s, 3H); 7.15 (d, 2H); 7.85 (d, 2H).

EXAMPLE 4

4-O-Methylhydroxylamine)phenoxymethyl-copoly(styrene-1%-divinylbenzene)-resin (100–200 mesh)

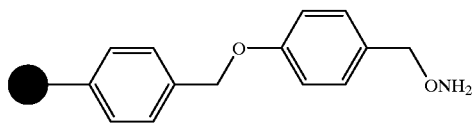

A 1-L jacketed reactor with a bottom valve and overhead stirrer (Ace catalog #8090) is charged with Wang resin (18.35 g, 20 meq) and anhydrous tetrahydrofuran (THF, 450 mL). This mixture is stirred gently for about 15 minutes, then as much solvent as possible is removed through a tube fitted with a porous glass frit via vacuum aspiration. Fresh THF is added, followed by triphenylphosphine (15.74 g, 60 mmol) and N-Hydroxyphthalimide (16.31 g, 100 mmol). The resulting mixture is stirred and cooled to −5–0° C. Diisopropyl azodicarboxylate (11.8 mL, 60 mmol) is added slowly so as to maintain the temperature at <5° C. When the addition is complete, the stirred mixture is allowed to warm slowly to room temperature and stirred overnight. As much of the reaction liquors as possible is removed by aspiration through the dip tube as above. The resin is washed by charging N,N-dimethylformamide (DMF, 200 mL), stirring the mixture for 3–5 minutes, and then removing by aspiration as much of the wash solution as possible. Similarly, the resin is washed sequentially with an additional portion of DMF and portions of methanol (twice), THF (twice), and methanol (once). A portion of the resin may be removed for analysis: IR 1734 cm-1 (C=O).

To the resin remaining in the reactor is added THF (400 mL) and 200 mL of a 40% aqueous solution of methylamine (2.31 mol). This reaction mixture is stirred gently at 40° C. for 2 hours, then cooled to room temperature (the mixture may be held overnight at this temperature). As much of the reaction liquor as possible is removed by aspiration, and the resin is washed with the solvent array as above. Following the final methanol wash, additional methanol is used to flush the resin out of the bottom of the reactor and isolate it by filtration. The filtered resin is dried at 40° C. under vacuum. Yield 18–18.5 g resin: amine load 1.02 meq/g (based on potentiometric titration of a THF suspension with p-toluenesulfonic acid); IR (microscopy) 3316 cm$^{-1}$ (w, —NH$_2$). Analysis found C, 87.07%; H, 7.77%; N, 1.58%, which corresponds to 1.13 nitrogen atoms/g resin.

Assay: Preparation of 4-nitrophenylethanehydroxamic Acid.

A 200 mg sample of the dried resin (ca. 0.2 mmol) is charged to a 5- or 10-mL resin reactor (a polypropylene syringe barrel fitted with a polypropylene frit). The resin is swelled for about 15 minutes in dry DMF, and then 115 mg 1-(3-dimethylaminopropyl)-3-ethylcarbodiimide hydrochloride (EDCI, 0.6 mmol) is added. To this mixture is then added 4-nitrophenylacetic acid (115 mg, 0.6 mmol). The reactor is capped and the mixture is agitated slowly overnight (a rocker bed apparatus is used). The reaction liquors are removed by vacuum filtration (the resin reactor is inserted through a small rubber vacuum flask adapter), and the resin is washed with several small (2–3 mL) portions of the following solvents: DMF (4–5 portions), MeOH or 50% aq. DMF (3–4 portions), THF (3–4 portions), and MeOH (2–3 portions). The resin (still in the syringe reactor) is dried for at least 4 hours under vacuum at 40° C.

To this dried resin is added 2 mL dichloromethane followed by 2 mL trifluoroacetic acid (TFA). Additionally, 20 mL water is added (believed to reduce "anhydride" formation from hydroxamic acid product). The mixture is allowed to react for about 1 hr, and the reaction liquors are drained into a tared collector. The resin is washed with 1–2 1-mL portions of dichloromethane followed by 1–2 1-mL portions of toluene. The combined filtrates are concentrated to about 2 mL at 30° C., 2 mL additional toluene is added, and the resulting solution is concentrated to dryness under vacuum (rotary evaporator followed by vacuum oven at 30° C.; note that heating in the presence of TFA promotes formation of the "anhydride" impurity). The residue is weighed and analyzed for weight % purity (HPLC, using the carboxylic acid as a response factor standard). Typical results for 4-nitrophenylethanehydroxamic acid: 29–30 mg solids at 60–70 wt % purity, 90–97 A % purity (261 nm); $^1$H NMR (CD$_3$OD) δ 8.13 (d, 7.25 (d, 2H), 4.85 (bs, OH, NH), 3.55 (s, 2H); $^{13}$C NMR δ 169.4, 144.3, 131.3, 124.6, 40.2. This reflects a load/clip chemical yield of 50–55% from resin at 1 meq/g.

EXAMPLE 5

N-4-phenylbut-1-oyl-4-O-methylhydroxylamine)phenoxymethyl-copoly(styrene-1%-divinyl Benzene)resin

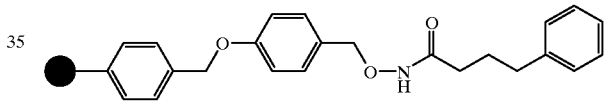

Dry 4-O-Methylhydroxylamine)phenoxymethyl-copoly(styrene-1%-divinylbenzene)-resin (2 g, 1.5 mmol), prepared as in Example 4, is allowed to swell in DMF (8 mL) for 10 minutes and then is treated with 4-phenyl butyric acid and EDC (0.86 g, 4.5 mmol). The mixture is shaken for 24 hours and filtered. The resin is washed with DMF, DMF/H$_2$O, DMF, THF and Et$_2$O and dried under vacuum at 40° C. to give N-4-phenylbut-1-oyl-4-O-methylhydroxylamine)phenoxymethyl-copoly(styrene-1%-divinylbenzene)-resin (2.2 g). IR: C=O 1670 cm$^{-1}$. Elemental analysis: calcd; N, 1.05%. Found: N, 1.07%.

EXAMPLE 6

N-(4-bromo-3-methylbenzoyl)-4-O-methylhydroxylamine)phenoxymethyl-copoly(styrene-1%-divinylbenzene)-resin

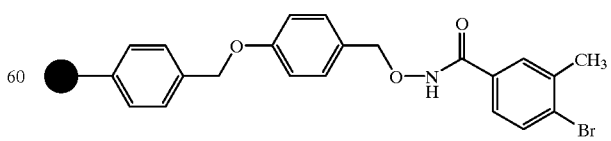

Dry 4-O-Methylhydroxylamine)phenoxymethyl-copoly(styrene-1%-divinylbenzene)-resin (4 g, 3 mmol), prepared as in Example 4, is allowed to swell in DMF (32 mL) for 10 minutes, then is treated with 4-bromo-3-methylbenzoic acid and EDC (1.725 g, 9 mmol). The mixture is shaken for 24 hours and filtered. The resin is washed with DMF, DMF/H$_2$O, DMF, THF and Et$_2$O and dried under vacuum at 40° C. to give N-(4-bromo-3-methylbenzoyl)-4-O-methylhydroxylamine)phenoxymethyl-copoly(styrene-1%-divinylbenzene)-resin (4.5 g). IR: C=O 1677.5 cm$^{-1}$. Elemental analysis: calcd: Br, 5.2%; N, 1.05%. Found: Br, 5.3%; N, 0.91%.

EXAMPLE 7

N-Hydroxy-4-bromo-3-methyl Benzamide

N-(4-bromo-3-methylbenzoyl)-4-O-methylhydroxylamine)phenoxymethyl-copoly(styrene-1%-divinylbenzene)-resin, prepared as in Example 6, is suspended in 50% TFA/CH$_2$Cl$_2$ for 2 hours. The resin is filtered and washed three times with CH$_2$Cl$_2$ to give N-Hydroxy-4-bromo-3-methyl benzamide. LC MS: m/z 230/232 (Br) [M+H]$^+$ Area=78%; $^1$H NMR (300 MHz, CDCl$_3$) δ: 2.42 (s, 3H), 7.4 (bd, J=7.89, 1H) 7.58 (bd J=7.89 1H), 7.62 (bs, 1H).

EXAMPLE 8

N-4-bromobenzyl-N-4-phenylbut-1-ylcarbonyl-4-O-methylhydroxylamine)phenoxymethyl-copoly(styrene-1%-divinylbenzene)-resin

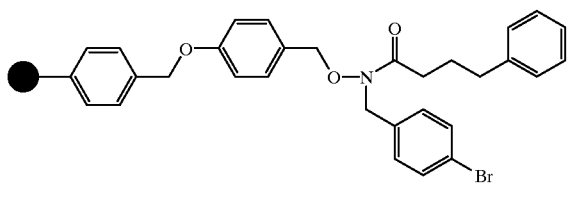

N-4-phenylbut-1-oyl-4-O-methylhydroxylamine)phenoxymethyl-copoly(styrene-1%-divinylbenzene)-resin (1.46 g, 1.095 mmol), prepared as in Example 5, is suspended in toluene (26 mL) for 10 minutes. DBU (0.83 mL; 5.5 mmol) is added and the mixture is agitated for 2 hours on a wrist shaker. Bromobenzyl bromide (4.1 g, 16.425 mmol) is added and the reaction mixture is vigorously agitated for 4 days. The resin is filtered and washed with DMF, DMF/H$_2$O, DMF, THF and Et$_2$O and dried under vacuum at 40° C. to give N-4-bromobenzyl-N-4-phenylbut-1-ylcarbonyl-4-O-methylhydroxylamine)phenoxymethyl-copoly(styrene-1%-divinylbenzene)-resin (1.4 g). IR C=O 1668 cm$^{-1}$. Elemental Analysis: calcd: Br, 5.3%; N, 0.94%. Found: Br, 5.4%; N, 0.85%.

EXAMPLE 9

4-Phenyl Butyraldehyde

N-4-bromobenzyl-N-4-phenylbut-1-oyl-4-O-methylhydroxylamine)phenoxymethyl-copoly(styrene-1%-divinylbenzene)-resin (0.2 g, 0.6 mmol/g 0.12 mmol) is suspended in diethyl ether for 10 minutes and then cooled to 5° C. in an orbital shaker. The suspension is treated with LiAlH$_3$OMe (0.46 M in diethyl ether, 0.22 mL, 0.1 mmol) and agitated for 30 minutes at this temperature. The reaction mixture is quenched by the addition of 2 M HCl (aq) and vortexed for 30 minutes. Sodium potassium tartrate is added and the mixture vortexed for a further 10 minutes. Sodium sulfate is added and the mixture is filtered through a plug of silica gel, washing thoroughly with dichloromethane. The filtrate is concentrated to give 4-phenyl butyraldehyde. GC: Area=91%; $^1$H NMR (CDCl$_3$) δ 9.75 (1H, s), 7.05–7.30 (5H, m), 2.58–2.68 (2H, m), 2.41–2.50 (2H, t), 1.91–2.02 (2H, m); MS (EI): m/z=149 [M+H$^+$].

EXAMPLE 10

6-Phenylhexan-3-one

N-4-bromobenzyl-N-4-phenylbut-1-oyl-4-O-methylhydroxylamine)phenoxymethyl-copoly(styrene-1%-divinylbenzene)-resin (0.15 g, approx. 0.75 mmol/g 0.11 mmol) is suspended in diethyl ether (1 mL) and treated with 1 M solution of ethyl magnesium bromide in tetrahydrofuran (0.34 mL, 0.34 mmol). The reaction mixture is agitated for 18 hours, and then quenched by the addition of 2 M HCl (aq) (approx. pH 3 is obtained). The mixture is agitated for 30 minutes. Sodium sulfate is added and the mixture is filtered through a plug of silica gel, washed thoroughly with dichloromethane and concentrated to give of 6-phenylhexan-3-one. GC MS (EI) Area=97.1%, m/z 176.2 (M)$^+$; MS (EI-LRP) m/z 176 (M)$^+$; NMR (300 MHz, CDCl$_3$) δ 1.02 (t, 3H), 1.9 (m, 2H), 2.4 (m, 4H) 2.6 (m, 2H), 7.2–7.3 (m, 5H).

EXAMPLE 11

N-4-chlorobenzyl-N-(4-bromo-3-methylbenzoyl)-4-O-methylhydroxylamine)phenoxymethyl-copoly(styrene-1%-divinylbenzene)-resin

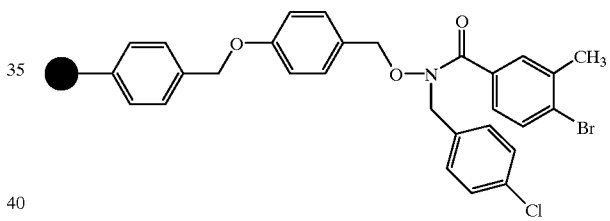

N-(4-bromo-3-methylbenzoyl)-4-O-methyl hydroxylamine)phenoxymethyl-copoly(styrene-1%-divinylbenzene)-resin (2.8 g, 2.1 mmol), prepared as in Example 6, is suspended in toluene (27 mL) and the mixture is stirred for 10 minutes. DBU (1.6 g, 10.5 mmol) is added and the mixture is agitated for 2 hours on a wrist shaker. Chlorobenzyl bromide (6.47 g, 31.5 mmol) is added and the reaction mixture is vigorously agitated for 3 days. The resin is filtered and washed with DMF, DMF/H$_2$O, DMF, THF and Et$_2$O, and dried under vacuum at 40° C. to give N-4-chlorobenzyl-N-(4-bromo-3-methylbenzoyl)-4-O-methylhydroxylamine)phenoxymethyl-copoly(styrene-1%-divinylbenzene)-resin (3 g). IR C=O 1644 cm$^{31\ 1}$; Elemental Analysis: calcd: Br, 4.2%; Cl, 1.9%; N, 0.8%. Found: Br, 3.8%; Cl, 2.0%; N, 0.9%.

EXAMPLE 12

N-(4-Chlorobenzyl)-N-hydroxy-3-methyl-4-bromobenzamide

N-4-chlorobenzyl-N-(4-bromo-3-methylbenzoyl)-4-O-methylhydroxylamine)phenoxymethyl-copoly(styrene-1%- divinylbenzene)-resin, prepared as in Example 11, is suspended in 50% TFA/CH$_2$Cl$_2$ for 2 hours. The resin is filtered and washed three times with CH$_2$Cl$_2$ to give N-(4-Chlorobenzyl)-N-hydroxy-3-methyl-4-bromobenzamide. LC MS (H-ISP) m/z 354/356 (Cl/Br) [M+H]$^+$ Area 64%; $^1$H NMR (300 MHz, CDCl$_3$) δ 2.3 (bs, 3H), 4.65 (bs, 2H), 7.2–7.6 (m, 7H).

EXAMPLE 13

4-Bromo-3-methyl Benzaldehyde

N-4-chlorobenzyl-N-(4-bromo-3-methylbenzoyl)-4-O-methylhydroxylamine)phenoxymethyl-copoly(styrene-1%-divinylbenzene)-resin (0.2 g, 0.5 mmol/g 0.1 mmol), prepared as in Example 11, is suspended in diethyl ether for 10 minutes and then cooled to 5° C. in an orbital shaker. The suspension is treated with LiAlH$_3$OMe (0.46 M in diethyl ether, 0.2 mL, 0.092 mmol) and agitated for 30 minutes at this temperature. The reaction mixture is quenched by the addition of aqueous 2 M HCl and vortexed for 30 minutes. Sodium potassium tartrate is added and the mixture is vortexed for a further 10 minutes. Sodium sulfate is added and the mixture is filtered through a plug of silica gel, washing thoroughly with dichloromethane. The filtrate is concentrated to give 4-bromo-3-methyl benzaldehyde. GC MS: EI Area=99.5%, m/z 179/199 (Br)[M]$^+$; $^1$H NMR (CDCl$_3$) δ 9.94 (1H, s), 7.70 (2H, d), 7.52 (1H, d), 2.45 (3H, s); MS (EI): m/z=199 [M+H$^+$].

EXAMPLE 14

1-(4-Bromo-3-methyl Phenyl)propan-1-one

N-4-chlorobenzyl-N-(4-bromo-3-methylbenzoyl)-4-O-methylhydroxylamine)phenoxymethyl-copoly(styrene-1%-divinylbenzene)-resin (0.23 g, 0.5 mmol/g 0.115 mmol), prepared as in Example 11, is suspended in diethyl ether (1 mL) and treated with ethyl magnesium bromide (1.0 M in THF, 0.23 mL, 0.23 mmol). The reaction mixture is agitated for 18 hours, and then quenched by the addition of aqueous 2 M HCl (approx. pH 3 is obtained). The mixture is agitated for 30 minutes. Sodium sulfate is added and the mixture is filtered through a plug of silica gel, washing thoroughly with dichloromethane. The residue is concentrated to give 1-(4-Bromo-3-methyl phenyl)propan-1-one. GC Area=78.7%; MS (EI) m/z 226 Br [M$^+$–H]; NMR (300 MHz, CDCl$_3$) δ 1.22 (t J=7.89, 3H), 2.96 (q J=7.89, 2H), 7.6 (bs, 2H), 7.8 (s, 1H).

EXAMPLE 15

N-3-bromobenzaldehyde oxime-4-O-Methylhydroxylamine)phenoxymethyl-copoly(styrene-1%-divinylbenzene)-resin

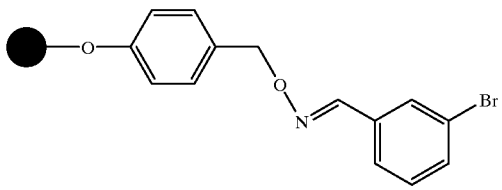

4-O-Methylhydroxylamine)phenoxymethyl-copoly(styrene-1%-divinylbenzene)-resin (105 mg; 0.08 mmol) is swelled in dichloromethane (DCM)(@ mL) for 10 minutes. Trimethylorthoformate (1 mL) and 3-bromo-benzaldehyde (500 mg; 2.7 mmol; 34 equiv.) are added to the resin and the mixture is shaken overnight. The slurry is then filtered, rinsed with dichloromethane (5 mL), DMF (5 mL×3), H$_2$O (5 mL×4), THF (5 mL×10, and Et$_2$O (5 mL×10). The resin is dried in vacuo at 40° C. for 12 hours. IR oxime stretch 1602 cm$^{-1}$. Elemental Analysis: calcd: Br, 5.52%; N, 1.04%. Found: Br, 5.76%; N, 1.08%.

EXAMPLE 16

N-3-(4-Methoxphenyl)propan-1-oyl-4-O-methylhydroxylamine)phenoxymethyl-copoly(styrene-1%-divinylbenzene)-resin

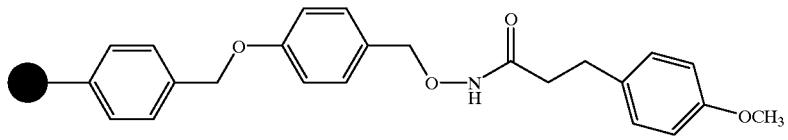

4-O-methylhydroxylamine)phenoxymethyl-copoly(styrene-1%-divinylbenzene)-resin (1 g, 0.73 mmol) is allowed to swell in DMF for 10 minutes and then is treated with 3-(4-methoxyphenyl)propionic acid (0.658 g, 3.65 mmol) and DIC (0.46 g, 3.65 mmol). The mixture is shaken for 24 hours, then filtered. The residue is washed with DMF, DMF/H$_2$O, DMF, THF and ET$_2$O, and dried under vacuum at 40° C. to give N-3-(4-methoxphenyl)propan-1-oyl-4-O-methylhydroxylamine)phenoxymethyl-copoly(styrene-1%-divinylbenzene)-resin. IR: C=O 1698 cm$^{-1}$. Elemental Analysis: calcd: N, 1.02%. Found: N, 1.21%.

EXAMPLE 17

N-hydroxy-3-(4-methoxyphenyl)propionamide

N-hydroxy-3-(4-methoxyphenyl)propionamide is prepared by reaction of N-3-(4-methoxphenyl)propan-1-oyl-4-O-methylhydroxylamine)phenoxymethyl-copoly(styrene-1%-divinylbenzene)-resin with TFA using the procedure of Example 7. $^1$H NMR 300 MHz (CDCl$_3$, CD$_3$OD) δ 2.25 (t, 2H), 2.78 (t, 2H), 3.68 (s, 3H), 6.72 (d, 2H), 7.04 (d, 2H).

EXAMPLE 18

N-2-(4-bromophenyl)ethan-1-oyl-4-O-methylhydroxylamine)phenoxymethyl-copoly(styrene-1%-divinylbenzene)-resin

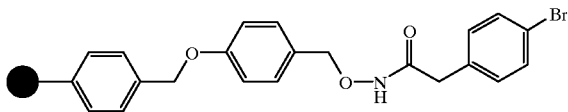

The title resin is prepared using the method of Example 16, except substituting 4-bromophenylacetic acid for 3-(4-methoxyphenyl)propionic acid. IR C=O 1713.9 cm$^{-1}$. Elemental analysis: calcd: Br, 5.8%; N, 1.02%. Found: Br, 8.29%, 8.18%; N, 0.97%, 0.96%.

| EDS: Net X-ray Counts | | | |
|---|---|---|---|
| | K line | L line | M line |
| O: | 969 | 1024 | |
| C: | 2662 | 3003 | |
| Br: | | | 12855  10436 |

EXAMPLE 19

N-4-bromocinnamoyl-4-O-methylhydroxylamine)phenoxymethyl-copoly(styrene-1%-divinylbenzene)resin

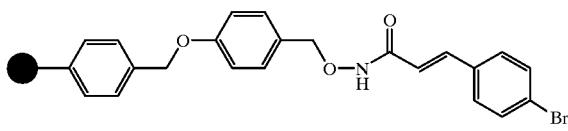

The title resin is prepared using the method of Example 16, except substituting 4-bromocinnamic acid for 3-(4-methoxyphenyl)propionic acid. IR:C=O 1671.7 cm$^{-1}$ (broad). Elemental analysis: Calcd: Br, 5.8%; N, 1.02%. Found: Br, 4.45%, 4.54%.

| EDS: Net X-ray Count | | | |
|---|---|---|---|
| | K line | L line | M line |
| O: | 818 | 1365 | |
| C | 4549 | 5059 | |
| Br: | | | 6384  5271 |

EXAMPLE 20

N-hydroxy-4-bromocinnamamide

N-hydroxy-4-bromocinnamamide is prepared by treating N-4-bromocinnamoyl-4-O-methylhydroxylamine)phenoxymethyl-copoly(styrene-1%-divinylbenzene)-resin with TFA using the procedure of Example 7. LC MS (H-ISP) m/z 241/243 Br [M$^+$], Area=84%; $^1$H NMR (300 MHz, CDCl$_3$, CD$_3$OD) δ: 3.23 (s, 1H), 6.35 (d, J=15.8), 7.3 (d, J=7.9), 7.4 (d, J=7.9), 7.6 (d, J=15.8).

EXAMPLE 21

N-(4-chlorobenzoyl)-4-O-methylhydroxylamine)phenoxymethyl-copoly(styrene-1%-divinylbenzene) resin

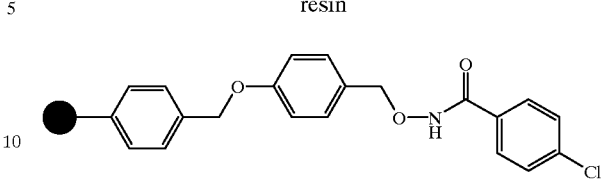

The title resin is prepared using the method of Example 16, except substituting 4-chlorobenzoic acid for 3-(4-methoxyphenyl)propionic acid. IR: C=O 1678 cm-1. Elemental Analysis: calcd: Cl, 2.66%; N, 1.05%. Found: Cl, 2.39%; N, 1.02%.

EXAMPLE 22

N-Hydroxy-4-chlorobenzamide

N-Hydroxy-4-chlorobenzamide is prepared by treating N-(4-chlorobenzoyl)-4-O-methylhydroxylamine)phenoxymethyl-copoly(styrene-1%-divinylbenzene)-resin with TFA using the procedure of Example 7. LC MS (H-ISP) m/z 172, 174 (Cl) [M+H]$^+$, Area=96%; $^1$H NMR (300 MHz, DMSO-d$_6$) δ 7.48 (d J=9.42, 2H), 7.69 (d J=9.42, 2H), 8.9–9.2 (broad, 1H), 11.28 (s, 1H).

EXAMPLE 23

N-methyl-N-(4-chlorobenzoyl)-4-O-methylhydroxylamine)phenoxymethyl-copoly(styrene-1%-divinylbenzene)-resin

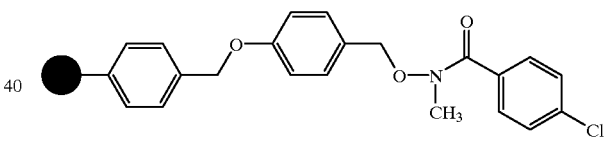

N-(4-chlorobenzoyl)-4-O-methylhydroxylamine)phenoxymethyl-copoly(styrene-1%-divinylbenzene)-resin (0.1 g, 0.075 mmol, 0.75 mmol/g) is suspended in toluene (2 mL) and cooled to 5° C. The mixture is treated with methyl iodide (1.5 mmol, 0.21 g, 93 µl) followed by DBU (0.22 mL, 0.228 g, 1.5 mmol). The reaction mixture is placed in a vortexer and allowed to warm to ambient temperature. Within a few minutes, a copious white precipitate forms and the mixture is diluted further with toluene (2 mL). Agitation of the reaction mixture is continued for 18 hours. The N-methyl-N-(4-chlorobenzoyl)-4-O-methylhydroxylamine)phenoxymethyl-copoly(styrene-1%-divinylbenzene)-resin is filtered and washed with DMF, DMF/H$_2$O, DMF, THF, Et$_2$O and dried in vacuo at 40° C.

EXAMPLE 24

1-(4-Chlorophenyl)propan-1-one

N-methyl-N-(4-chlorobenzoyl)-4-O-methylhydroxylamine)phenoxymethyl-copoly(styrene-1%-divinylbenzene)-resin is suspended in diethyl ether (0.7 mL) and treated with ethyl magnesium bromide (1.0 M in THF, 0.225 mL, 0.225 mmol). The reaction mixture is agitated for 18 hours on a wrist shaker and then quenched by the addition of 5% HCl in ethanol. Agitation is maintained for a further 30 minutes and the mixture is then filtered through a small plug of silica to remove the inorganic material. The filtrate is concentrated to afford 1-(4-chlorophenyl)propan-1-one. MS (EI-LRP) m/z 168/170 Cl [M$^+$], 169/171 Cl [M+H]$^+$; $^1$H NMR (300 Mhz, CDCl$_3$) δ 1.22 (t, 3H), 2.98 (q, 2H), 7.42 (d, 2H), 7.9 (d, 2H).

EXAMPLE 25

N-[3-((4-methoxyphenyl)sulfonyl)propan-1-oylcarbonyl]-4-O-methylhydroxylamine) phenoxymethyl-copoly(styrene-1%-divinylbenzene)-resin

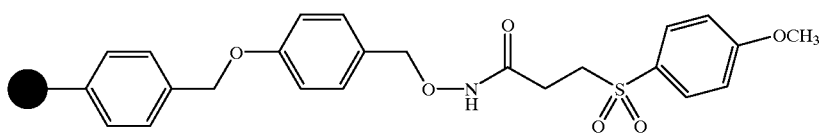

N-[3-((4-methoxyphenyl)sulfonyl)propan-1-oylcarbonyl]-4-O-methylhydroxylamine)phenoxymethyl-copoly(styrene-1%-divinylbenzene)-resin is prepared using the method of Example 16, except substituting 3-(4-methoxyphenylsulfonyl)propionic acid for 3-(4-methoxyphenyl)propionic acid. IR C=O 1691.6 cm$^{-1}$ (broad). Elemental Analysis: calcd: N, 1.02%; S, 2.34%. Found: N, 1.03%; S, 2.5%.

EXAMPLE 26

N-hydroxy-3-(4-methoxyphenylsulfonyl) propionamide

N-hydroxy-3-(4-methoxyphenylsulfonyl)propionamide is prepared by treating N-[3-((4-methoxyphenyl)sulfonyl) propan-1-oylcarbonyl]-4-O-methylhydroxylamine) phenoxymethyl-copoly(styrene-1%-divinylbenzene)-resin with TFA using the procedure of Example 7. $^1$H NMR (300 Mhz, DMSO-d$_6$) δ 2.25 (t, 2H), 3.42 (t, 2H) 3.85 (s, 3H), 7.13 (d, 2H), Spray) m/z 259 [M$^+$], Area=44%.

EXAMPLE 27

N-allyoxycarbonyl-4-(O-methylhydroxylamine) phenoxymethyl-copoly(styrene-1% divinylbenzene) resin

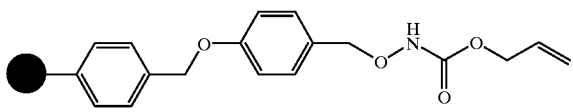

4-(O-methylhydroxylamine)phenoxymethyl-copoly (styrene-1% divinylbenzene)resin (2 g, 2 mmol) is suspended in 15 ml of dichloromethane and shaken on a wrist shaker for 10 minutes and 284 mg (383 μL, 2.2 mmol) of diisopropylethyl amine is added. The mixture is shaken for 30 minutes. Allyl chloroformate (265 mg, 233 ul, 2.2 mmol) is added and the mixture is shaken overnight. The N-allyoxycarbonyl-4-(O-methylhydroxylamine) phenoxymethyl-copoly(styrene-1% divinylbenzene)resin is washed with 15 ml of dichloromethane, THF (3×) and dichloromethane (3×) and dried in vacuo

EXAMPLE 28

N-4-bromobenzyl-N-allyoxycarbonyl-4-(O-methylhydroxylamine)phenoxymethyl-copoly (styrene-1% divinylbenzene)resin

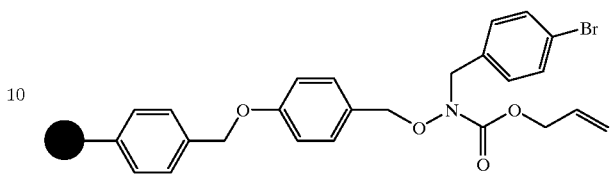

The N-allyoxycarbonyl-4-(O-methylhydroxylamine) phenoxymethyl-copoly(styrene-1% divinylbenzene)resin prepared in Example 27 is suspended in 15 mL of toluene. DBU (1,522 g, 1.5 ml, 10 mmol) and 4-bromobenzyl bromide (2.5 g, 10 mmol) are added and the mixture is shaken for 70 hours. The N-4-bromobenzyl-N-allyoxycarbonyl-4-(O-methylhydroxylamine) phenoxymethyl-copoly(styrene-1% divinylbenzene)resin is washed with 15 mL of DMF (3×), THF (3×) and dichloromethane (3×) and dried in vacuo.

EXAMPLE 29

N-4-bromobenzyl-4-(O-methylhydroxylamine) phenoxymethyl-copoly(styrene-1% divinylbenzene) resin

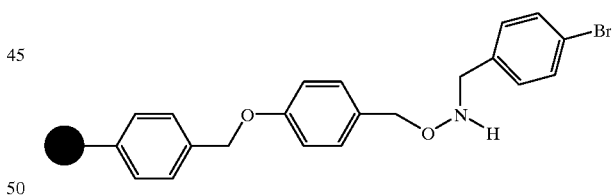

N-4-bromobenzyl, N-allyoxycarbonyl-4-(O-methylhydroxylamine)phenoxymethyl-copoly(styrene-1% divinylbenzene)resin, prepared as in Example 28, is swelled in 6 mL of THF, 6 mL of DMSO, 3 mL of 0.5 n HCl. Pd(Ph$_3$P)$_4$ (347 mg, 15 weight %) is added and the mixture is shaken for 5 minutes. Morpholine (4.3 mL) is added and the mixture is shaken overnight. The reagents are drained off and the N-4-bromobenzyl-4-(O-methylhydroxylamine) phenoxymethyl-copoly(styrene-1% divinylbenzene)resin is washed with DMF (2×), THF (2×), dichloromethane (2×), 0.5% diisopropylethyl amine in dichloromethane (3×), 0.5% sodium diethyldithiocarbamate in DMF (3×), DMF (3×), THF (3×) and dichloromethane (3×) and dried in vacuo overnight.

EXAMPLE 30

N-(indol-2-ylcarbonyl)-N-4-bromobenzyl-4-(O-methylhydroxylamine)phenoxymethyl-copoly(styrene-1% divinylbenzene)resin

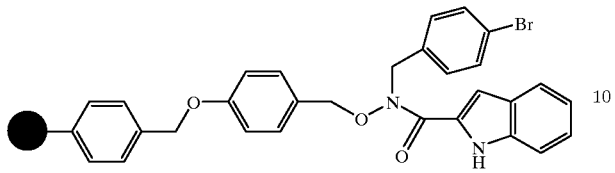

N-4-bromobenzyl-4-(O-methylhydroxylamine) phenoxymethyl-copoly(styrene-1% divinylbenzene)resin (1.17 g, 1 mmole), prepared as in Example 29, is suspended in 15 ml of DMF. Indole-2-carboxylic acid (483 mg, 3 mmol) and 575.1 mg (3 mmol) of 1(3-dimethylaminopropyl)-3-diethylcarbidiimide hydrochloride are added and the mixture is shaken for 16 hours. The N-(indol-2-ylcarbonyl)-N-4-bromobenzyl-4-(O-methylhydroxylamine)phenoxymethyl-copoly(styrene-1% divinylbenzene)resin is drained and washed with 15 ml of DMF (3×), THF/20% $H_2O$ (3×), THF (3×), and dichloromethane (3×) and dried in vacuo.

EXAMPLE 31

Indole-2-carboxaldehyde

Dry N-(indol-2-ylcarbonyl)-N-4-bromobenzyl-4-(O-methylhydroxylamine)phenoxymethyl-copoly(styrene-1% divinylbenzene)resin is swelled in 12 mL of THF, shaken and cooled at 0° C. for 30 minutes. $LiAlH_4$ (0.62 ml, 3 eq) is added and the mixture is shaken at 0° C. for 30 minutes. Saturated $KHSO_4$ solution (0.5 mL) and 0.3 mL of potassium, sodium tartrate solution are added and the mixture is shaken for 30 minutes while warming to room temperature. Excess $H_2O$ is dried by adding dry $Na_2SO_4$ and shaking for 15 minutes more. The mixture is filtered under low nitrogen pressure and washed 3 more times with 8 mL of dichloromethane followed by filtration. The filtrate is dried with $Na_2SO_4$ and filtered twice through a short bed (1 inch) of silica gel 60 for column chromatography (particle size 0.040–0.063 mm) and the solvent is removed in vacuo to give indole-2-carboxaldehyde. $^1$H NMR ($CDCl_3$) δ 9.84 (1H, s), 9.22 (1H, brs), 7.75 (1H, d), 7.14–7.48 (4H, m); MS (EI): m/z=146 [M+H$^+$].

EXAMPLE 32

N-(3,4-dimethoxycinnamoyl)-4-O-methylhydroxylamine)phenoxymethyl-copoly(styrene-1%-divinylbenzene)-resin

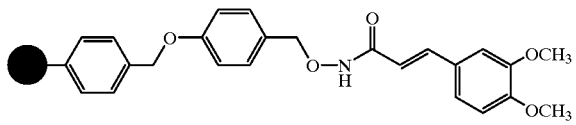

4-O-Methylhydroxylamine)phenoxymethyl-copoly(styrene-1%-divinylbenzene)-resin resin (1 g, 1 mmole) is washed with DMF (15 mL), then suspended in 15 mL of DMF and 624.6 mg (3 mmole, 3×excess) of 3,4-dimethoxy cinnamic acid and 575.1 mg (3 mmol, 3×excess) of 1-(3-dimethylaminopropyl)-3-dimethylaminopropyl)-3-ethylcarbodiimide hydrochloride are added and the mixture is shaken for 16 hours. The resin is drained and washed with 15 mL of DMF (1×), THF/20% $H_2O$ (3×), THF (3×), dichloromethane (3×) and dried under vacuum overnight.

EXAMPLE 33

N-4-bromobenzyl-N-(3,4-dimethoxycinnamoyl)-4-O-methylhydroxylamine)phenoxymethyl-copoly(styrene-1%-divinylbenzene)-resin

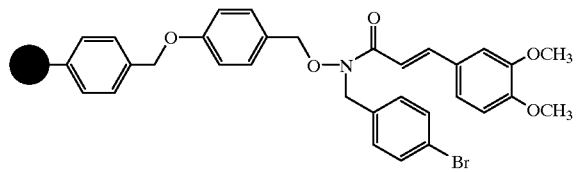

Dry N-(3,4-dimethoxycinnamoyl)-4-O-methylhydroxylamine)phenoxymethyl-copoly(styrene-1%-divinylbenzene)-resin is shaken in 15 mL of toluene for 10 minutes, then 0.9 mL (6 mmol, 6×excess) of DBU is added and the mixture is shaken for 2 hours. p-Bromo benzyl bromide (1.5 g, 6 mmol, 6×excess) is added and the mixture is shaken for 3 days. The resin is dried overnight in vacuo.

EXAMPLE 34

3-4-Dimethoxycinnamaldehyde

Dry N-4-bromobenzyl-N-(3,4-dimethoxycinnamoyl)-4-O-methylhydroxylamine)phenoxymethyl-copoly(styrene-1%-divinylbenzene)-resin is swelled in 12 mL of dry THF, shaken and cooled to 0° C. for 30 minutes. $LiAlH_4$ in THF (0.5 mL, 2 equivalents) is added and the mixture is shaken at 0° C. for 30 minutes. Saturated aqueous $KHSO_4$ solution (0.5 mL) and potassium, sodium tartrate solution (0.3 mL) are added and the mixture is shaken for 30 minutes while warming to ambient temperature. Excess $H_2O$ is dried by adding dry $Na_2SO_4$ and shaking for 15 minutes. The mixture is filtered under low nitrogen pressure, washed 3 times with 8 mL of dichloromethane and filtered. The filtrate is further dried with $Na_2SO_4$ and filtered through a short (1 inch) bed of silica gel 60 for column chromatography (particle size 0.040–0.063 mm) and the solvent is removed in vacuo to give 3,4-dimethoxycinnamaldehyde. $^1$H NMR ($CDCl_3$) δ 9.65 (1H, d), 7.40 (1H, d), 7.12 (1H, d), 7.06 (1H, s), 6.87 (1H, d), 6.60 (1H, dd), 3.90 (6H, s); MS (EI): m/z=193 [M+H$^+$].

EXAMPLES 35–42

The compounds of Examples 35–42 are prepared from the desired carboxylic acid starting material using the procedures of Examples 32–34.

EXAMPLE 35

Anthranilic Aldehyde $^1$H NMR ($CDCl_3$) δ 9.88 (1H, s), 7.52–7.58 (1H, d), 7.11–7.38 (7H, m), 6.81 (1H, t); MS (EI): m/z=198 [M+H$^+$].

EXAMPLE 36

2-Bibenzylic Aldehyde $^1$H NMR ($CDCl_3$) δ 10.18 (1H, s), 7.83 (1H, d), 7.14–7.52 (8H, m), 3.30 (2H, t), 2.87 (2H, t); MS (EI): m/z=211 [M+H$^+$].

EXAMPLE 37

4-Methoxy-2-quinoline Aldehyde $^1$H NMR (CDCl$_3$) δ 10.17 (1H, s), 8.27 (1H, d), 8.18 (1H, d), 7.78 (1H, t), 7.62 (1H, t), 7.38 (1H, s), 4.12 (3H, s); MS (EI): m/z=188 [M+H$^+$].

EXAMPLE 38

3-Acetamido Benzaldehyde $^1$H NMR (CDCl$_3$) δ 9.98 (1H, s), 7.97 (1H, s), 7.86 (1H, d), 7.62 (1H, d), 7.48 (1H, t), 2.21 (3H, s). MS (EI): m/z=164 [M+H$^+$].

EXAMPLE 39

4-(4-N-Propylphenyl)benzaldehyde $^1$H NMR (CDCl$_3$) δ 10.02 (1H, s), 7.92 (2H, d), 7.72 (2H, d), 7.53 (2H, d), 7.26 (2H, d), 2.65 (2H, t), 1.68 (2H, dt), 0.95 (3H, t); MS (EI): m/z=225 [M+H$^+$].

EXAMPLE 40

3-Quinoline Aldehyde $^1$H NMR (CDCl$_3$) δ 10.26 (1H, s), 9.38 (1H, s), 8.64 (1H, s), 8.20 (1H, d), 7.98 (1H, t), 7.65 (1H, t); MS (EI): m/z=158 [M+H$^+$].

EXAMPLE 41

3-(3,4-Methylenedioxy)propionaldehyde $^1$HNMR (CDCl$_3$) δ 9.80 (1H, s), 7.60–7.74 (3H, m), 5.92 (2H, s), 2.88 (2H, t), 2.74 (2H, t); MS (EI): m/z=179 [M+H$^+$].

EXAMPLE 42

2-Phenyl-4-quinoline Aldehyde $^1$H NMR (CDCl$_3$) δ 10.58 (1H, s), 9.00 (1H, d) 8.19–8.30 (4H, m), 7.82 (1H, t), 7.70 (1H, t), 7.47–7.59 (3H, m); MS (EI): m/z=234 [M+H$^+$].

EXAMPLE 43

4-Carboxy-2,3,5,6-tetrafluorophenoxymethyl-copoly(styrene-1% divinylbenzene)resin

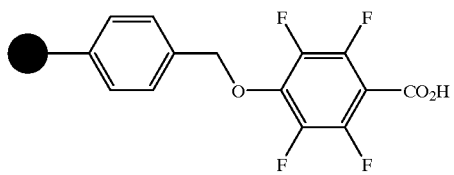

Merrifield resin (2 mmol/g, 600 mg, 1.2 mmol) is swelled in anhydrous DMF (20 mL). 2,3,5,6-tetrafluoro-4-hydroxy benzoic acid hydrate (2.28 g, 10 mmol) and cesium carbonate (3.26 g, 10 mmol) are added and the reaction mixture is heated at 85° C. for 12 hours with gentle agitation. The reaction mixture is filtered and the 4-carboxy-2,3,5,6-tetrafluorophenoxymethyl-copoly(styrene-1% divinylbenzene)resin is washed with DMF (5×), 20% aqueous DMF (5×), THF (5×) and dichloromethane and dried overnight in vacuo. IR (microscope, cm–1): 1640 (C=O); $^{19}$F NMR (nanoprobe) –144.4 ppm, –160.2 ppm.

EXAMPLE 44

N-4-benzyl-4-(O-methylhydroxylamine)phenoxymethyl-copoly(styrene-1% divinylbenzene) resin

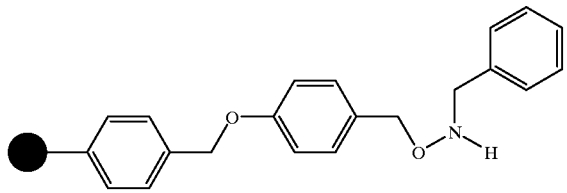

4-(O-Methylhydroxylamine)phenoxymethyl-copoly(styrene-1%-divinylbenzene)-resin (2 g; 2 mmol), prepared as in Example 4, is swelled in DCM (15 ml), DIEA (0.383 ml; 2.2 mmol) is added and the mixture is shaken for 1 hour. Allyl chloroformate (0.234 ml; 2.2 mmol) is added and the mixture is shaken overnight. The resin is drained and washed three times each with DCM, THF and DCM and dried in vacuum. The dry resin is swelled in anhydrous toluene (18 ml), DBU (1.5 ml; 10 mmol) added and the mixture is shaken for 1 hour. Benzyl bromide (1.19 ml; 10 mmol) is added and the mixture is shaken for 3 days. The resin is drained and washed three times each with DCM, DMF, THF and DCM and dried overnight in vacuum. To the resin is added THF (6 ml), DMSO (6 ml), 0.5 N HCl (2.5 ml), tetrakis(triphenylphosphine)palladium(0) (347 mg; 15 mol %) and morpholine (4.3 ml) and the mixture is shaken overnight. The resin is then drained and washed in three times each with DMF, THF, DCM, 0.5% in DCM, 0.5% sodium diethyidithiocarbamate in DMF, DMF, THF and DCM and then dried in vacuum. A resin sample is cleaved with excess 1:1 TFA/DCM for 1 hour at ambient temperature, then washed three times with 1 ml of the cleavage mixture, evaporated and dried in vacuo. $^1$H NMR (CD$_3$OD): δ 7.44 (m, 5H), 4.36 (s, 2H); MS (EI): m/z=124 [M+H]$^+$.

EXAMPLE 45

Preparation of 4-(1-Ethanone)-2-(fluorophenoxymethyl)-copoly(styrene-1% divinylbenzene)resin

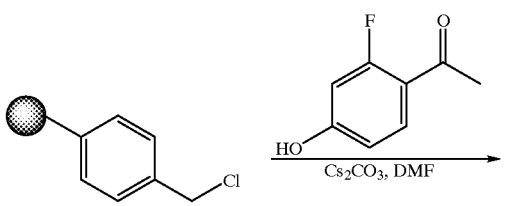

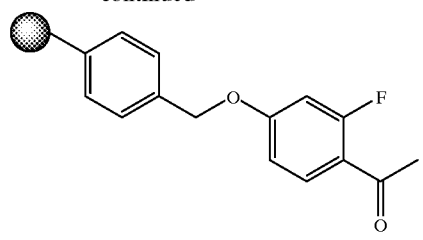

To a suspension of chloromethyl polystyrene (Merrifield resin) (5.0 g, 8.9 mmol, resin loading 1.78 mmol/g) and cesium carbonate (29.0 g, 90 mmol, 10 eq.) in dry DMF (100 ml) was added 4-hydroxy-2-fluoroacetophenone (6.9 g, 45 mmol, 5 eq.) in dry DMF (20 ml). The mixture was mechanically stirred at 80° C. for 24 hours. The solution was cooled, washed with THF:1N HCl soln. (3:1, ×3), THF:H$_2$O (3:1, ×3), THF (×3) and DCM (×3). The 4-(1-ethanone)-2-fluorophenoxymethyl)-copoly(styrene-1% divinylbenzene) resin was dried in vacuo at 40° C. overnight. IR (C=O) 1682 cm$^{-1}$. d$^{19}$F (CDCl$_3$) −108 ppm. Theoretical loading 1.47 mmol/g. Analysis found C, 80.04; H, 6.47; F, 2.92, which corresponds to 1.53 fluorine atoms/g; 1.47 calculated for 100% loading.

EXAMPLE 46

Preparation of 4-(Hydroxylethyl)-2-(fluorophenoxymethyl)-copoly(styrene-1% divinylbenzene)resin

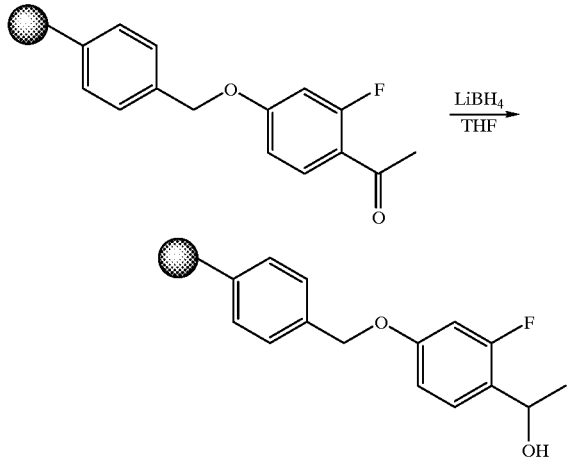

To a suspension of 4-(1-ethanone)-2-fluorophenoxymethyl)-copoly(styrene-1% divinylbenzene) resin (0.25 g, 0.37 mmol) in dry THF was added lithium borohydride (0.93 ml of a 2.0 M soln. in THF, 1.85 mmol, 5 eq.). The mixture was shaken at room temperature for 4 hours. The resin was filtered, washed with THF (×3), THF:H$_2$O (3:1, ×3), THF (×3) and DCM (×3). The 4-(hydroxylethyl)-2-fluorophenoxymethyl)-copoly(styrene-1% divinylbenzene)resin was dried in vacuo at 40° C. overnight. IR (C=O) disappears. d$^{19}$F (CDCl$_3$) −121 ppm. Theoretical loading 1.47 mmol/g. Analysis found C, 78.02; H, 6.79; F, 2.76, which corresponds to 1.45 fluorine atoms/g; 1.47 calculated for 100% loading.

EXAMPLE 47

Preparation of 4-(Methyl-O-methylhydroxylamine)-2-fluorophenoxymethyl-copoly(styrene-1% divinylbenzene)resin

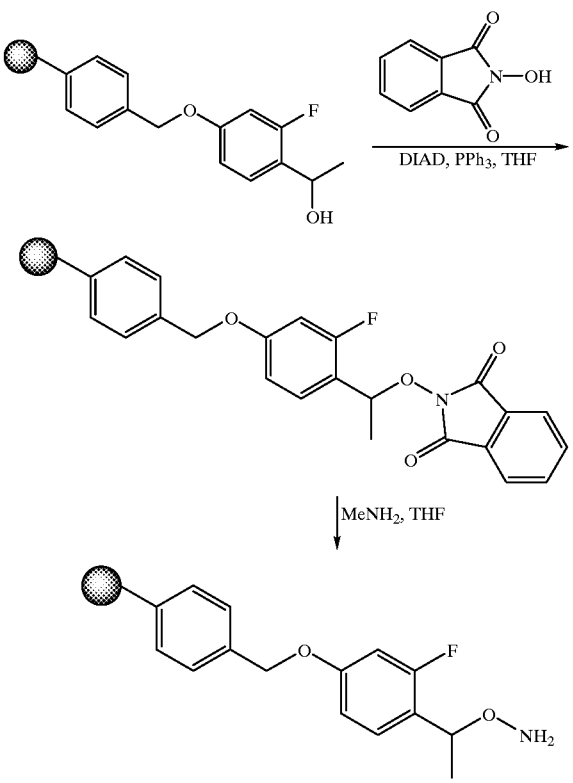

To a suspension of 4-(hydroxylethyl)-2-fluorophenoxymethyl)-copoly(styrene-1% divinylbenzene) resin (2.0 g, 2.9 mmol), triphenylphosphine (2.3 g, 8.7 mmol, 3 eq.) and N-hydroxyphthalimide (2.4 g, 14.5 mmol, 5 eq.) in THF (30 ml) at 0° C. was added diisopropylazodicarboxylate (1.7 ml, 8.7 mmol, 3 eq.). The solution was allowed to warm to room temperature over ca. 30 minutes. The mixture was shaken for 24 hours. The resin was filtered, washed with DMF (×3), MeOH (×3), THF (×3), DCM (×3). The hydroxyphthalimido resin was dried in vacuo at 40° C. overnight. IR (C=O) 1737 cm$^{-1}$. $^{19}$F (CDCl$_3$) −119 ppm. Theoretical loading 1.19 mmol/g.

The hydroxyphthalimido resin was re-suspended in THF (40 ml) and methylamine (20 ml of a 40% wt. soln. in water) was added. The reaction mixture was heated at 40° C. for 2 hours. The resin was filtered, washed with DMF (×3), MeOH (×3), THF (×3), DCM (×3). The resin was dried in vacuo at 40° C. overnight to give the 4-(methyl-O-methylhydroxylamine)-2-fluorophenoxymethyl-copoly (styrene-1% divinylbenzene) resin. IR (C=O) disappears, (N—H) 3380 cm$^{-1}$ broad. Analysis found C, 82.62; H, 7.21; N, 0.60; F, 3.13. d$^{19}$F (CDCl$_3$) −120 ppm. Theoretical loading 1.41 mmol/g.

EXAMPLE 48

Preparation of N-benzyl-4-(methyl-O-methylhydroxylamine)-2-fluorophenoxymethyl-copoly(styrene-1%-divinylbenzene)resin

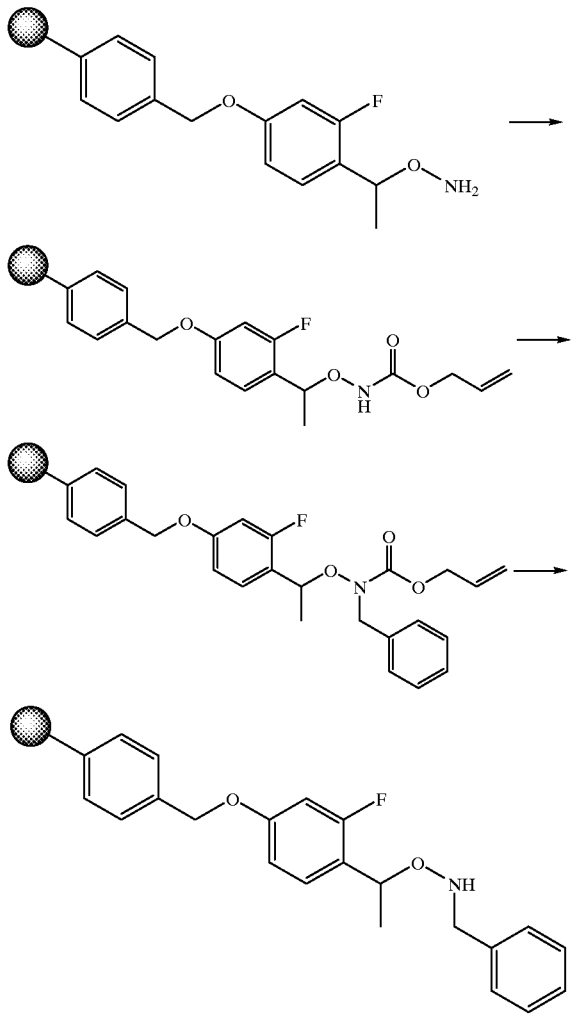

To a suspension of the 4-(methyl-O-methylhydroxylamine)-2-fluorophenoxymethyl-copoly(styrene-1% divinylbenzene)resin (2.78 g, 3.92 mmol) in CH$_2$Cl$_2$ (30 ml) was added allyl chloroformate (1.25 ml, 11.8 mmol, 3 eq.) and diisopropylethylamine (2.05 ml, 11.8 ml, 3 eq.). The mixture was shaken for 24 hours. The resin was filtered, washed with CH$_2$Cl$_2$ (×3), THF (×3), THF:H$_2$O (3:1, ×3), THF (×3), DCM (×3). The N-(1-propylenecarbonyl)-4-(methyl-O-methylhydroxylamine)-2-fluorophenoxymethyl-copoly(styrene-1%-divinylbenzene) resin was dried in vacuo at 40° C. overnight. IR (C=O) 1757 cm$^{-1}$. $^{19}$F (CDCl$_3$) −120 ppm. Theoretical loading 1.26 mmol/g. The N-(1-propylenecarbonyl)-4-(methyl-O-methylhydroxylamine)-2-fluorophenoxymethyl-copoly(styrene-1%-divinylbenzene)resin was re-suspended in dry toluene (30 ml) and DBU (2.93 ml, 19.6 mmol, 5 eq.) was added. The reaction mixture was shaken for 1 hour. Benzyl bromide (2.33 ml, 19.6 mmol, 5 eq.) was then added. The resin was shaken overnight. The resin was filtered, washed with THF (×3), THF;H$_2$O (3:1, ×3), THF (×3), DCM (×3). The N-benzyl-N-(1-propylenecarbonyl)-4-(methyl-O-methylhydroxylamine)- 2-fluorophenoxymethyl-copoly(styrene-1%-divinylbenzene)resin was dried in vacuo at 40° C. overnight. IR (C=O) 1761 cm$^{-1}$. d$^{19}$F (CDCl$_3$) −120 ppm. Theoretical loading 1.13 mmol/g.

The resin was suspended in DMSO (10 ml) and THF (10 ml). 0.5 N HCl soln (2.5 ml) was added followed by tetrakis(triphenylphosphine)palladium (0.23 g, 0.196 mmol, 5 mol %) and morpholine (5 ml). The mixture was shaken overnight. The resin was filtered, washed with DMF (×5), THF (×3), MeOH (×3), DCM (×3), 0.5% conc. HCl in DMF (×3), 5 wt % diethyidithiocarbamate in DMF (×3), DMF (×5), THF (×3), MeOH (×3), DCM (×3) and dried in vacuo at 40° C. overnight to afford the N-benzyl-4-(methyl-O-methylhyroxylamine)-2-fluorophenoxymethyl-copoly(styrene-1%-divinylbenzene)resin. IR (C=O) disappears. d$^{19}$F (CDCl$_3$) −120 ppm. Theoretical loading 1.25 mmol/g.

EXAMPLE 49

Preparation of O-(N-9-Fluorenylmethoxycarbonyl Glycine)-4-(hydroxyethyl)-2-fluorophenoxymethyl)-copoly(styrene-1% divinylbenzene)resin

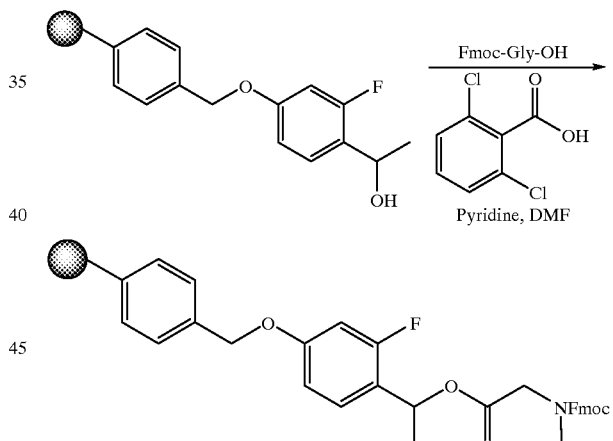

To a suspension of the 4-(hydroxyethyl)-2-fluorophenoxymethyl)-copoly(styrene-1% divinylbenzene) resin (1.0 g, 1.47 mmol) in dry DMF (20 ml) was added Fmoc-Gly-OH (1.31 g, 4.41 mmol, 3 eq.), pyridine (0.71 ml, 8.82 mmol, 6 eq.) and 2,6-dichlorobenzoyl chloride (0.63 ml, 4.41 mmol, 3 eq.). The mixture was shaken overnight. The mixture was filtered and washed with THF (×3), THF:H$_2$O (3:1, ×3), THF (×3), MeOH (×3) and CH$_2$Cl$_2$ (×3). The O-(N-9-fluorenylmethoxycarbonyl glycine)-4-(hydroxyethyl)-2-fluorophenoxymethyl)-copoly(styrene-1% divinylbenzene)resin was dried in vacuo at 40° C. overnight. IR (C=O) 1726 cm$^{-1}$. $^{19}$F −118 ppm. Theoretical loading 1.04 mmol/g.

EXAMPLE 50

Preparation of O-(N-diphenylmethylene Glycine)-4-(hydroxyethyl)-2-fluorophenoxymethyl)-copoly(styrene-1% divinylbenzene)resin

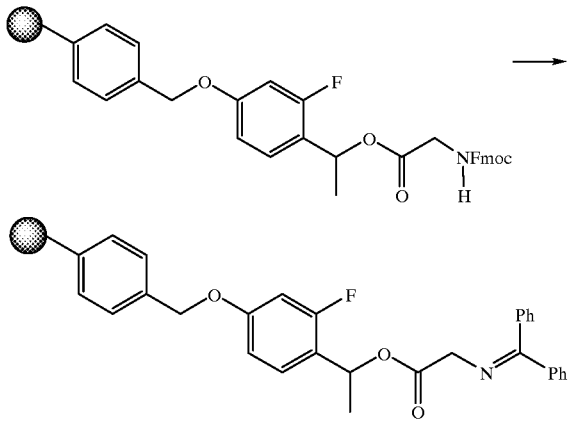

The resin (0.75 g, 0.78 mmol) was suspended in 20% piperidine solution in DMF (10 ml). The mixture was shaken for 2 hours. The solution was filtered and washed with DMF (5) and NMP (×5). The resin was re-suspended in NMP (8 ml) and benzophenone imine (1.3 ml, 7.8 mmol, 10 eq.) and acetic acid (0.40 ml, 7.0 mmol, 9 eq.) was added. The mixture was shaken overnight. The solution was filtered and washed with NMP (×5), CH2 Cl2 (×3), THF (×3), THF:H$_2$O (3:1, ×3), THF (×3), (×3). The O-(N-diphenylmethylene glycine)-4-(hydroxyethyl)-2-fluorophenoxymethyl)-copoly(styrene-1% divinylbenzene)resin was dried in vacuo at 40° C. overnight. IR (CO) 1742 cm$^{-1}$, (C=N) 1627 cm$^{-1}$. Theoretical loading 1.11 mmol/g.

EXAMPLE 51

Preparation of N-[1-(4-methylphenyl)-ethanoic Acid]-2-naphthalenecarboxamide

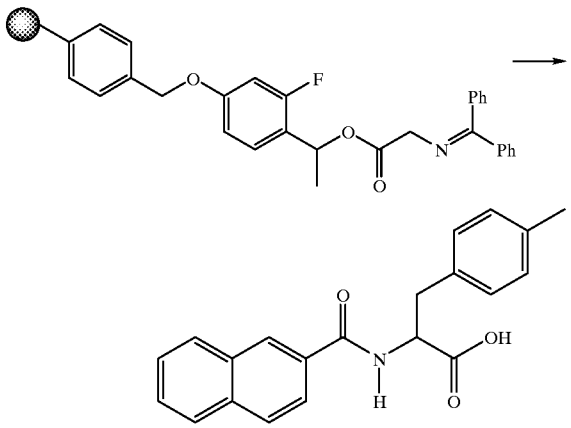

The O-(N-diphenylmethylene glycine)-4-(hydroxyethyl)-2-fluorophenoxymethyl)-copoly(styrene-1% divinylbenzene)resin (0.045 g, 50 mmol) was suspended in dry NMP (1 ml) and 4-methylbenzyl bromide (0.019 g, 100 mmol, 2 eq.) was added followed by 2-tert-butylimino-2-diethylamino-1,3-dimethyl-perhydro-1,3,2-diazaphosphorine (0.03 ml, 100 mmol, 2 eq.). The mixture was shaken overnight. The resin was filtered and washed with NMP (×3), DCM (×3), THF (×3), THF:H$_2$O (3:1, ×3), THF (×3).

A mixture of THF:1N HCl soln. (2:1, 1.5 ml) was added to the resin and the mixture shaken for 4 hours. The resin was filtered and washed with NMP (×3), DIEA:NMP (1:10, ×3), NMP (×3), DCM (×3), NMP (×3).

The resin was re-suspended in NMP (1 ml) and 2-naphthoic acid (0.086 g, 500 mmol, 10 eq.), HOBt (0.068 g, 500 mmol, 10 eq.) and DIC (0.078 ml, 500 mmol, 10 eq.) were added. The mixture was shaken overnight. The resin was filtered and washed with NMP (×3), DCM (×3), DCM:MeOH (1:1, ×3), MeOH (×3) and DCM (×3).

Trifluoroacetic acid (1 ml) and DCM (1 ml) were added and the mixture was shaken for 1 hour. The solution was filtered into a tared vial, and the resin was washed with DCM (×3). The solvent was removed in vacuo to yield N-[1-(4-methylphenyl)-ethanoic acid]-2-naphthalenecarboxamide (0.0167 g, 100%). LCMS gives 333 [(M)$^+$, 100%].

EXAMPLE 52

Preparation of O-(diethylphosphonoaceto)-4-(hydroxyethyl)-2-fluorophenoxymethyl)-copoly(styrene-1% divinylbenzene)resin To a suspension of the 4-(hydroxyethyl)-2-fluorophenoxymethyl)-copoly(styrene-1% divinylbenzene) resin (1.0 g, 1.47 mmol) in dry DMF (8 ml) was added diethylphosphonoacetic acid (0.71 ml, 4.41 mmol, 3 eq.), pyridine ((0.71 ml, 8.82 mmol, 6 eq.) and 2,6-dichlorobenzoyl chloride (0.63 ml, 4.41 mmol, 3 eq.). The reaction mixture was shaken overnight. The resin was filtered, washed with DMF (×3), THF (×3), DCM (×3), MeOH (×3) and THF (×3). The O-(diethylphosphonoaceto)-4-(hydroxyethyl)-2-fluorophenoxymethyl)-copoly(styrene-1% divinylbenzene)resin was dried in vacuo at 40° C. overnight. IR (C=O) 1737 cm$^{-1}$, (P=O) 1260 cm$^{-1}$. d$^{19}$F (CDCl$_3$) −119 ppm. Theoretical loading 1.17 mmol/g.

EXAMPLE 53

Preparation of 4-Methylcinnamic Acid

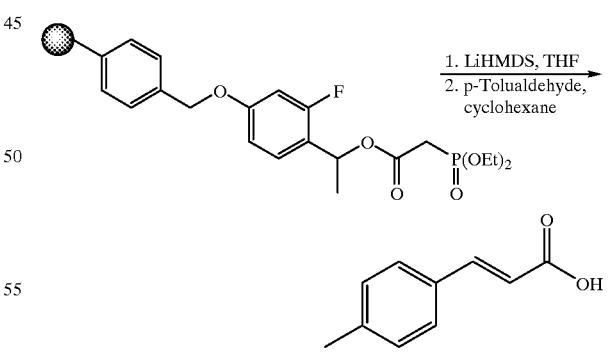

To a suspension of the O-(diethylphosphonoaceto)-4-(hydroxyethyl)-2-fluorophenoxymethyl)-copoly(styrene-1% divinylbenzene)resin (0.1 g, 0.117 mmol) in dry THF (3 ml) at 0° C. was added LiHMDS soln (0.29 ml of a 1.0 M soln. in THF, 0.29 mmol, 2.5 eq.). The solution was allowed to warm to room temperature over 30 minutes. The solution was filtered under an inert atmosphere, and p-tolualdehyde (0.033 ml, 0.28 mmol, 2.4 eq.) in dry cyclohexane (1.5 ml) was added. The reaction mixture was shaken overnight. The resin was filtered, washed with DMF (×3), THF:H₂O (3:1, ×3), DCM (×3), THF (×3) and DCM (×3). The resin was dried in vacuo at 40° C. overnight. IR (C=O) disappears, (P=O) disappears.

Trifluoroacetic acid (1 ml) and DCM (1 ml) were added and the mixture was shaken for 1 hour. The solution was filtered into a tared vial, the resin was washed with DCM (×3). The solvent was removed in vacuo to yield 4-methylcinnamic acid (0.0201 g, quant). LCMS gives 144 [(M−H₂O)⁺, >90%].

EXAMPLE 54

Preparation of N-hydroxy-phenyl-acetamide

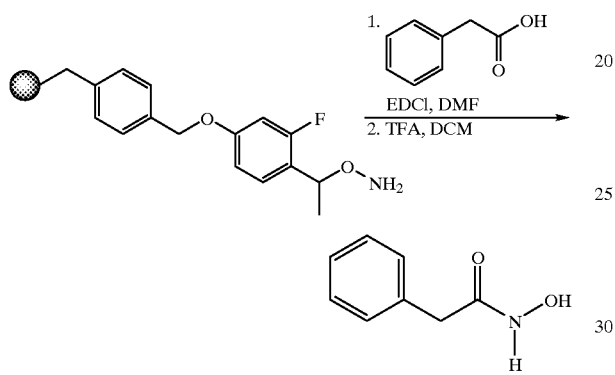

To a suspension of the 4-(methyl-O-methylhydroxylamine)-2-fluorophenoxymethyl-copoly(styrene-1% divinylbenzene)resin (0.10 g, 0.14 mmol) in dry DMF (2 ml) is added 1-[3-(dimethylamino)propyl]-3-ethylcarbodiimide hydrochloride (0.08 g, 0.42 mmol, 3 eq.). To the mixture is then added phenylacetic acid (0.06 g, 0.42 mmol, 3 eq.). The mixture is shaken overnight. The resin is filtered and washed with DMF (×5), THF: H₂O (3:1, ×5), THF (×3), MeOH (×3) and DCM (×3). To the resin is added TFA (1 ml) and DCM (1 ml) and the mixture shaken for 1 hour. The mixture is filtered into a tared vial and the resin washed with DCM (×2) and toluene (×2). The combined filtrates are evaporated in vacuo to yield N-hydroxy-phenyl-acetamide (0.0084 g, 39%). LCMS gives 151 [M⁺].

EXAMPLE 55

The 4-(1-ethanone)-2-(fluorophenoxymethyl)-copoly(styrene-1% divinylbenzene)resin depicted below could easily be oxidized by known methods, such as sodium hydroxide in the presence of iodine, to afford the carboxylic acid resin derivative (as in Hing et al. J. Am. Soc., 66, 894, 1944).

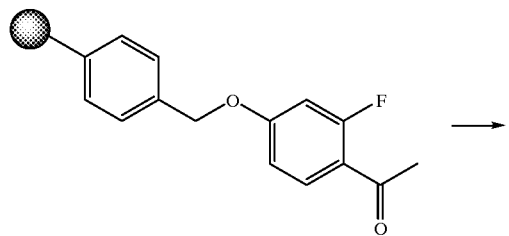

-continued

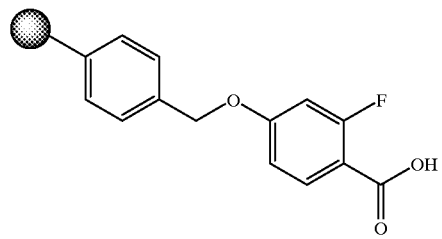

EXAMPLE 56

The carboxylic acid resin derivative depicted below could easily be reduced using diborane, or other reducing agents to give the benzylic alcohol resin derivative.

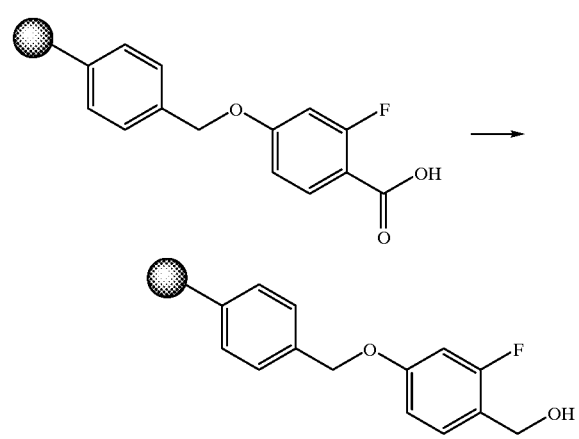

Alternatively, the benzylic alcohol resin derivate of Example 56 is made as illustrated in Examples 56a–56e.

EXAMPLE 56a

2-Fluoro-4-methoxymethoxyacetophenone

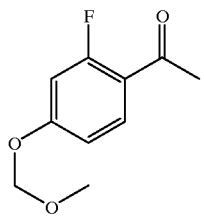

To a suspension of sodium hydride (6.05 g, 151.2 mmol, 60% wt. in oil) in dry THF (150 ml) under an inert atmosphere (nitrogen) is slowly added 2-fluoro-4-hydroxyacetophenone (23.3 g, 151.2 mmol) in dry THF (150 ml). The solution is heated to reflux for 1 hour. The solution is then cooled to room temperature and chloromethyl methyl ether (12.0 ml, 144 mmol) in dry THF (50 ml) is added dropwise over 15 minutes. The solution is refluxed for 1 hour. The solution is poured into water (500 ml) and extracted with ether (3×150 ml). The combined extracts are dried over MgSO₄ and evaporated in vacuo to give a brown liquid. The product is obtained as a colorless liquid (27.8 g, 93%) after column chromatography (silica; hexane;ethyl acetate; 5:1, v/v). $\delta_H$ (300 MHz, CDCl₃) 2.54 (3H, s), 3.44 (3H, s), 5.17 (2H, s), 6.72–6.82 (2H, m), 7.82 (1H, t, J=8.7 Hz); $\delta_C$ (75 MHz, CDCl₃) 31.39, 31.49, 56.62, 94.56, 103.91, 104.28, 112.66, 119.57, 119.74, 131.86, 162.18, 162.56, 162.72, 165.56, 194.66, 194.71; m/z 198 [(M⁺), 100%].

EXAMPLE 56b

2-Fluoro-4-methoxymethoxybenzoic Acid

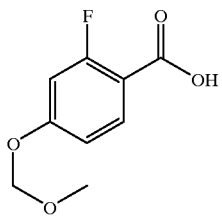

To a solution of 2-fluoro-4-methoxymethoxyacetophenone (20.0 g, 101 mmol) in dioxane (100 ml) is added sodium hypochlorite solution (200 ml, 10–13%). The solution is heated at 70° C. for 5 hours, after which time a further amount of sodium hypochlorite solution (100 ml, 10–13%) is added and heating continued overnight. The solution is cooled and extracted with ether (2×200 ml). The aqueous layer is acidified (conc. HCl) and extracted with ether (3×200 ml). The combined extracts are dried over MgSO₄ and evaporated in vacuo to give an off-white solid (19.9 g, 99%). $\delta_H$ (300 MHz, CDCl₃) 3.38 (3H, s), 5.12 (2H, s), 6.70–6.79 (2H, m), 7.85 (1H, t, J=8.8 Hz); $\delta_C$ (75 MHz, CDCl₃) 56.66, 95.50, 105.16, 105.51, 113.02, 113.08, 134.66, 134.69, 163.09, 163.68, 163.84, 166.52, 167.14, 167.19, 205.33; m/z 200 [(M⁺), 60%].

EXAMPLE 56c

Methyl-2-fluoro-4-hydroxybenzoate

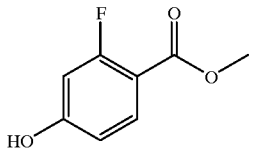

To a solution of 2-fluoro-4-methoxymethoxybenzoic acid (19.9 g, 100 mmol) in methanol (200 ml) is added conc. hydrochloric acid solution (0.5 ml, catalytic). The solution is heated at reflux overnight. The solution is evaporated in vacuo to give an off-white solid (16.9 g, 100%). $\delta_H$ (300 MHz, CD₃OD) 3.83 (3H, s), 6.52 (1H, dd, J=2.3, 12.9 Hz), 6.63 (1H, dd, J=2.1, 8.5 Hz), 7.78 (1H, t, J=8.7 Hz); $\delta_C$ (75 MHz, CD₃OD); m/z 170 [(M⁺), 10%], 139 [(M-OMe)⁺, 10%]52.34, 104.30, 104.34, 110.78, 112.48, 134.61, 134.96, 163.36, 163.61, 164,93, 165.03, 165.09, 165.19, 166.38, 166.46, 166.79, 167.03, 167.60, 167.65, 205.58.

EXAMPLE 56d 4-(Methylformate)-2-fluorophenoxymethyl)-copoly (styrene-1% divinylbenzene)resin

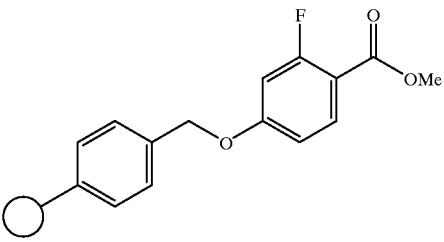

To a suspension of Merrifield resin (5.0 g, 8.9 mmol, loading 1.78 mmol/g) and cesium carbonate (30.0 g, 89 mmol) in dry DMF (80 ml) is added methyl-2-fluoro-4-hydroxybenzoate (7.57 g, 44.5 mmol) in dry DMF (40 ml). The suspension is mechanically stirred at 80° C. overnight. The mixture is cooled, filtered and washed with DMF (×3), THF;1N HCl (3:1, ×3), THF:H₂O (3:1, ×3), THF (×3) and MeOH (×3). The resin is dried in vacuo overnight. $\delta_F$ (75 MHz, CDCl₃) –108 ppm. IR (C=O) 1717 cm⁻¹. Theoretical loading 1.44 mmol/g. Analysis found C,?; H,?; F,?, which corresponds to ??? fluorine atoms/g; ???calculated for 100% loading.

EXAMPLE 56e 4-(Hydroxymethyl)-2-fluorophenoxymethyl)-copoly (styrene-1% divinylbenzene)resin

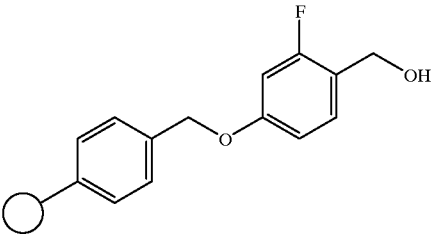

The resin (6.2 g, 8.9 mmol, loading 1.44 mmol/g) was swelled in dry THF (30 ml) with gentle agitation for 15 minutes. To the suspension was added lithium aluminum hydride solution (44.5 ml, 44.5 mmol, 1.0 M solution in THF). The resin was agitated for 2 hrs. The mixture was filtered and washed with THF (×3), TFH:H₂O (3:1, ×3), MeOH (×3), THF (×3) and CH₂Cl₂ (×3). The resin was dried in vacuo overnight. $\delta_F$ (75 MHz, CDCl₃)ppm. IR (C=O) 1717 cm⁻¹ disappears. Theoretical loading 1.44 mmol/g. Analysis found C,?; H,?; F,?, which corresponds to ???fluorine atoms/g; ???calculated for 100% loading.

EXAMPLE 57

The mono-fluoro-benzyl alcohol resin derivative depicted below could easily be converted to the hydroxyl amine resin under analogous conditions for the synthesis of 4-(methyl-O-methylhydroxylamine)-2-fluorophenoxymethyl-copoly (styrene-1% divinylbenzene)resin in Example 47 above.

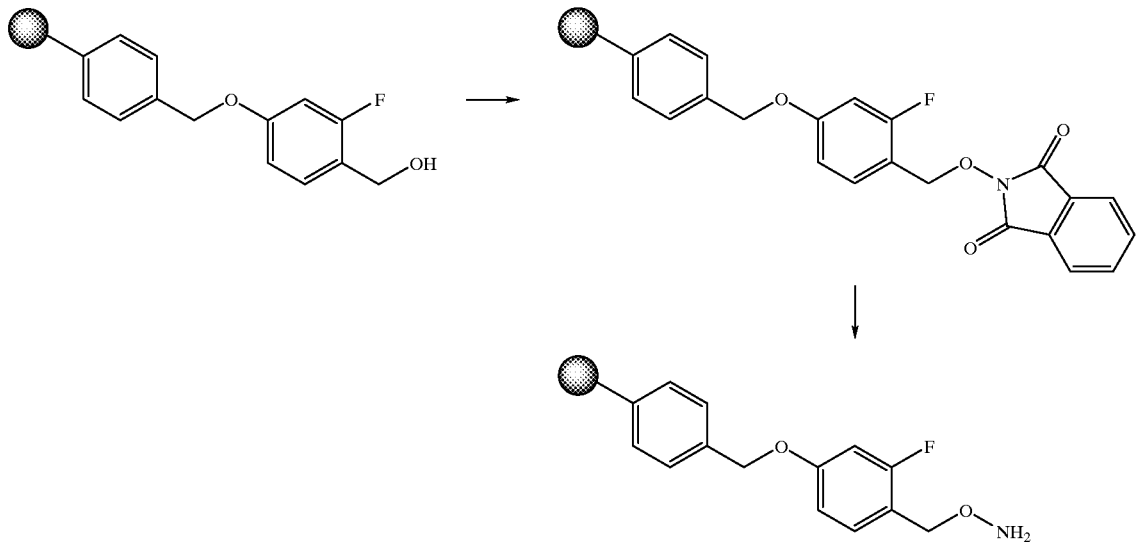

EXAMPLE 58

Preparation of 4-(1-Ethanone)-2-fluorophenoxymethyl)-copoly(styrene-1% divinylbenzene-5% 4-florostyrene)resin

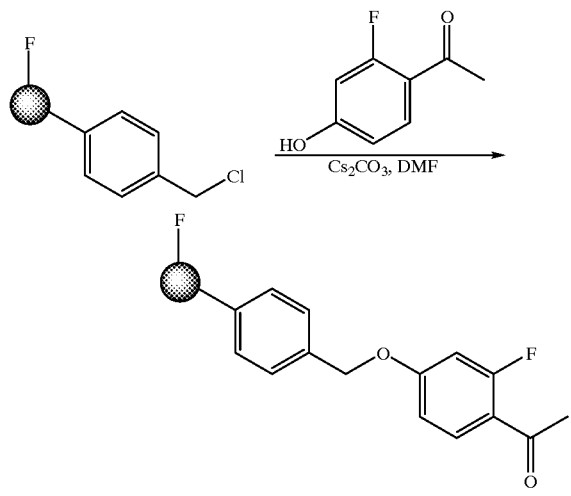

To a suspension of fluorinated chloromethyl polystyrene (fluoro-Merrifield resin) (5.0 g, 8.0 mmol, resin loading 1.60 mmol/g, 5 wt % Fluorostyrene) and cesium carbonate (26.1 g, 80 mmol, 10 eq.) in dry DMF (80 ml) is added 4-hydroxy-2-fluoroacetophenone (6.17 g, 40 mmol, 5 eq.) in dry DMF (20 ml). The mixture is mechanically stirred at 80° C. for 24 hours. The solution is cooled and washed with THF:1N HCl soln. (3:1, ×3), THF:H$_2$O (3:1, ×3), THF (×3) and DCM (×3). The 4-(1-ethanone)-2-fluorophenoxymethyl)-copoly (styrene-1% divinylbenzene-5% 4-fluorostyrene)resin is dried in vacuo at 40° C. overnight. IR (C=O) 1682 cm$^{-1}$. d$^{19}$F (DMF) –109, –122 ppm. Theoretical loading 1.35 mmol/g. Analysis found C, 84.25; H, 6.80; F, 3.86.

EXAMPLE 59

Preparation of 4-(1-hydroxylethyl)-2-fluorophenoxymethyl)-copoly(styrene-1% divinylbenzene-5% 4-fluorostyrene)resin

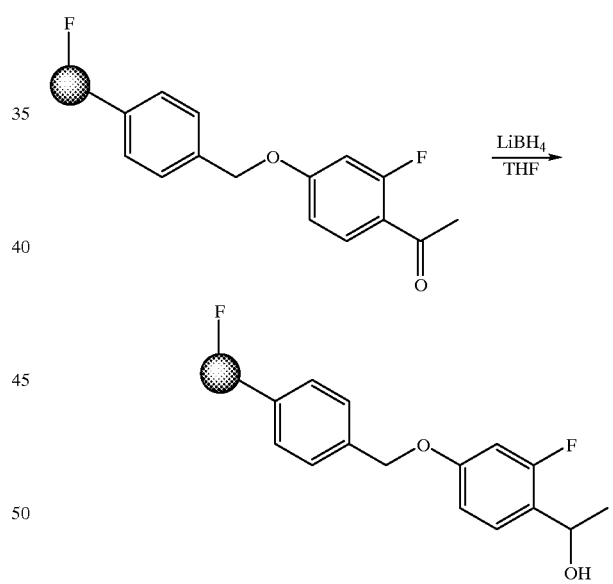

To a suspension of the 4-(1-ethanone)-2-fluorophenoxymethyl)-copoly(styrene-1% divinylbenzene-5% 4-fluorostyrene)resin (3.0 g, 4.05 mmol) in dry THF (50 ml) is added lithium borohydride (10.1 ml of a 2.0M soln. in THF, 20.2 mmol, 5 eq.). The mixture is shaken at room temperature for 2 hours. The resin is filtered and washed with THF (×3), THF:H$_2$O (3:1, ×3), THF (×3) and DCM (×3). The 4-(1-hydroxyethyl)-2-fluorophenoxymethyl)-copoly(styrene-1% divinylbenzene-5% 4-fluorostyrene) resin is dried in vacuo at 40° C. overnight. IR (C=O) disappears. d$^{19}$F (DMF) –121, –122 ppm. Theoretical loading 1.35 mmol/g. Analysis found C, 84.00; H, 7.10; F, 3.77.

EXAMPLE 60

Preparation of O-(diethylphosphonoacetate)-4-(hydroxyethyl)-2-fluorophenoxymethyl)-copoly(styrene-1% divinylbenzene-5% 4-fluorostyrene) resin

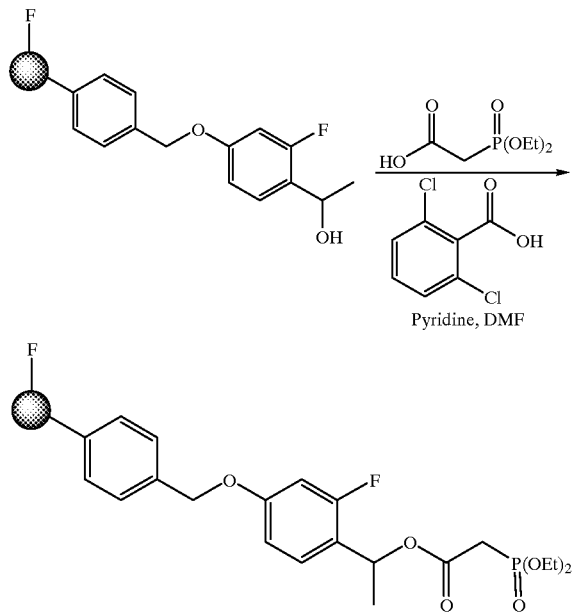

To a suspension of the 4-(1-hydroxylethyl)-2-fluorophenoxymethyl)-copoly(styrene-1% divinylbenzene-5% 4-fluorostyrene)resin (1.5 g, 2.03 mmol) in dry DMF (20 ml) are added diethylphosphonoacetic acid (0.98 ml, 6.1 mmol, 3 eq.), pyridine (0.99 ml, 12.2 mmol, 6 eq.) and 2,6-dichlorobenzoyl chloride (0.87 ml, 6.1 mmol, 3 eq.). The reaction mixture is shaken overnight. The resin is filtered and washed with DMF (×3), THF (×3), DCM (×3), MeOH (×3) and THF (×3). The O-(diethylphosphonoacetate)-4 (hydroxyethyl)-2-fluoroethylmethyl)-copoly(styrene-1% divinylbenzene-5% 4-fluorostyrene)resin is dried in vacuo at 40° C. overnight. IR (C=O) 1742 cm$^{-1}$, (P=O) 1265 cm$^{-1}$. $^{19}$F (DMF) −120, −121 ppm. Theoretical loading 1.17 mmol/g.

EXAMPLE 61

Preparation of 4-Methylcinnamic Acid

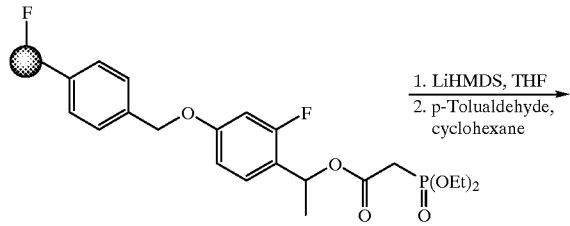

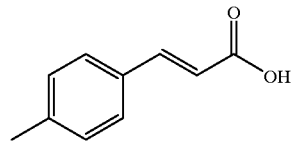

To a suspension of the O-(diethylphosphonoacetate)-4-(hydroxyethyl)-2-fluorophenoxymethyl)-copoly(styrene-1% divinylbenzene-5% 4-fluorostyrene)resin (0.1 g, 0.11 mmol) in dry THF (3 ml) at 0° C. is added LiHMDS soln (0.55 ml of a 1.0 M soln. in THF, 0.55 mmol, 5 eq.). The solution is allowed to warm to room temperature over 30 minutes. The solution is filtered under an inert atmosphere, and p-tolualdehyde (0.08 ml, 0.66 mmol, 6 eq.) in dry cyclohexane (1.5 ml) is added. The reaction mixture is shaken overnight. The resin is filtered and washed with DMF (×3), THF:H$_2$O (3:1, ×3), DCM (×3), THF (×3) and DCM (×3). The resin is dried in vacuo at 40° C. overnight. IR (C=O) disappears, (P=O) disappears. $^{19}$F (DMF) −119, −121 ppm.

Trifluoroacetic acid (1 ml) and DCM (1 ml) are added to the resin and the mixture is shaken for 1 hour. The solution is filtered into a tared vial and the resin is washed with DCM (×3). The solvent is removed in vacuo to yield 4-methylcinnamic acid (17.6 mg, 99%). $^1$H NMR (MeOH) 2.35 (3H, s), 6.40(1H, d, J=16 Hz), 7.21 (2H, d, J=8 Hz), 7.46 (2H, d, J=8 Hz), 7.63 (1H, d, J=16 Hz). LCMS gives [(M)$^+$, 100%].

EXAMPLE 62

Preparation of O-(N-9-fluorenylmethoxycarbonyl Phenylalanine)-4-(hydroxyethyl)-2-fluorophenoxymethyl)-copoly(styrene-1% divinylbenzene-5% 4-fluorostyrene)resin

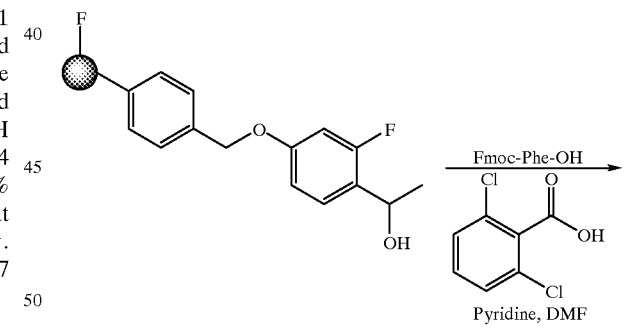

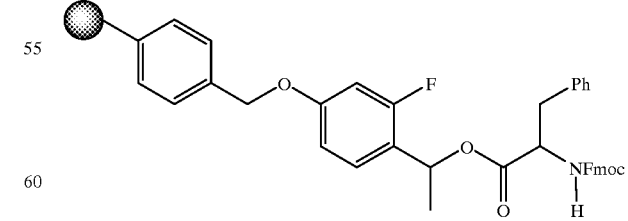

To a suspension of the starting resin (0.25 g, 0.34 mmol) in dry DMF (4 ml) are added Fmoc-Phe-OH (0.40 g, 1.02 mmol, 3 eq.), pyridine (0.16 ml, 2.04 mmol, 6 eq.) and 2,6-dichlorobenzoyl chloride (0.15 ml, 1.02 mmol, 3 eq.).

The mixture is shaken overnight. The mixture is filtered and washed with THF (×3), THF:H$_2$O (3:1, ×3), THF (×3), MeOH (×3) and CH$_2$Cl$_2$ (×3). The O-(N-9-fluorenylmethoxycarbonyl phenylalanine)-4-(hydroxyethyl)-2-fluorophenoxymethyl)-copoly(styrene-1% divinylbenzene-5% 4-fluorostyrene)resin is dried in vacuo at 40° C. overnight. IR (C=O) 1732 cm$^{-1}$. Theoretical loading 0.89 mmol/g.

EXAMPLE 63

Preparation of Fmoc-Gly-Phe-OH

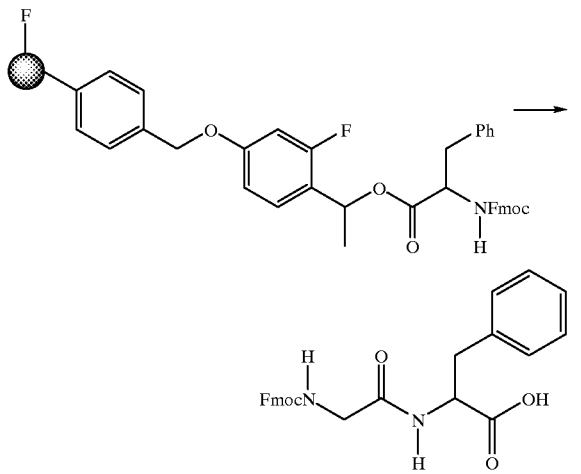

To a suspension of O-(N-9-fluorenylmethoxycarbonyl phenylalanine)-4-(hydroxyethyl)-2-fluorophenoxymethyl)-copoly(styrene-1% divinylbenzene-5% 4-fluorostyrene) resin (0.04 g, 0.036 mmol) is added piperidine in DMF (10% soln., 1 ml). The mixture is shaken for 1 hour. The mixture is filtered and washed with DMF (×5) and NMP (×5). IR (C=O) 1737 cm$^{-1}$.

The resin is re-suspended in NMP (1.5 ml) and Fmoc-Gly-OH (0.069 g, 225 mmol, 5 eq.), HOBt (0.034 g, 225 mmol, 5 eq.) and DIC (0.035 ml, 225 mmol, 5 eq.) are added. The mixture is shaken overnight. The mixture is filtered and washed with NMP (×3), DCM (×3), DCM:MeOH (1:1, ×3), MeOH (×3) and DCM (×3). IR (C=O) 1668, 1732 cm$^{-1}$. Trifluoroacetic acid (1 ml) and DCM (1 ml) are added to the resin and the mixture is shaken for 1 hour. The solution is filtered into a tared vial and the resin is washed with CH$_2$Cl$_2$ (×3). The solvent is removed in vacuo to yield Fmoc-Gly-Phe-OH (12.2 mg, 78%). LCMS gives 444 [(M)$^+$, 100%].

EXAMPLE 64

N-α-(tert-Butoxycarbonyl)-L-alaninal

N-4-benzyl-4-(O-methylhydroxylamine)phenoxymethyl-copoly(styrene-1% divinylbenzene) resin (1.08 g; 1 mmole), prepared as in Example 44, is washed with DMF (15 ml), suspended in 15 ml of DMF and Boc-Ala-OH (568 mg; 3 mmol) and EDCI (575.1 mg; 3 mmol) are added and the mixture is shaken for 16 hours. The resin is drained and washed with 15 ml of DMF (2×), THF/20% H$_2$O (3×), THF (3×), DCM (3×) and dried in vacuo overnight. The dry resin is swelled in 12 ml of anhydrous THF under nitrogen, shaken for 10 minutes and cooled to 0° C. for 30 min. LAH in THF (0.75 ml; 3 mmol) is added and the mixture is shaken at 0° C. for 30 minutes. Saturated KHSO$_4$ (0.5 ml) and K, Na tartrate (0.3 ml) solutions are added and the reaction mixture is shaken for 20 minutes while warming to ambient temperature. Excess water is dried by addition of dry Na$_2$SO$_4$ and shaking for 15 minutes. The mixture is filtered under low nitrogen pressure, washed three times with 8 ml of DCM and filtered. The filtrate is further dried with Na$_2$SO$_4$ and filtered with DCM through a short (1 inch) bed of silica gel 60 for column chromatography (particle size 0.040–0.063 mm). Solvent removal and drying in vacuo afford 44 mg of the title compound. $^1$H NMR: δ 9.56 (s, 1H), 5.10 (brs, 1H), 4.22 (q, 1H), 1.45 (m, 9H), 1.34 (d, 3H); MS (IS): m/z=173 [M$^+$]. Purity estimated 90% by $^1$H NMR.

EXAMPLES 65–69

The following compounds are prepared from the appropriate amino acid starting material using the method of Example 64.

EXAMPLE 65

N-α-(tert-Butoxycarbonyl)-L-valinal $^1$H NMR: δ 9.61 (s, 1H), 5.09 (brs, 1H), 4.27 (m, 1H), 1.80 (brm, 1H), 1.48 (m, 9H), 1.03 (d, 3H), 0.95 (d, 3H); MS (IS): m/z=201 [M$^+$]. Purity estimated 90% by $^1$H NMR.

EXAMPLE 66

N-α-(tert-Butoxycarbonyl)-L-phenylalaninal $^1$H NMR: δ 9.62 (s, 1H), 7.12–7.34 (m, 5H), 5.04 (brs, 1H), 4.42 (t, 1H), 3.09 (d, 2H), 1.39 (s, 9H); MS (IS): m/z=250 [M+H]$^+$ LC Area (UV$_{220}$)=91%.

EXAMPLE 67

N-α-(tert-Butoxycarbonyl)-β-(t-butyl)-L-aspartal $^1$H NMR: δ 9.63 (s, 1H), 5.60 (brs, 1H), 2.82 (m, 2H), 2.02 (m, 1H), 1.42 (m, 18H); MS (IS): 274 [M+H]$^+$ LC Area (UV$_{220}$)=80%.

EXAMPLE 68

N-α-(tert-Butoxycarbonyl)-N-ε-(tert-butoxycarbonyl)-L-lysinal-OH $^1$H NMR: δ 9.53 (s, 1H), 5.21 (brs, 1H), 3.12 (m, 2H), 1.88 (m, 2H), 1.18–1.66 (m, 22H); MS (IS): m/z=331 [M+H]$^+$ LC Area (UV$_{220}$)=67%.

EXAMPLE 69

Indole-2-carboxaldehyde $^1$H NMR: δ 9.82 (s, 1H), 7.14–7.75 (m, 6H); MS (EI): m/z=145 [M$^+$] LC Area (UV$_{254}$)=90%.

EXAMPLES 70–120

Parallel Synthesis of Arrays of Anthranilic Acid Compounds

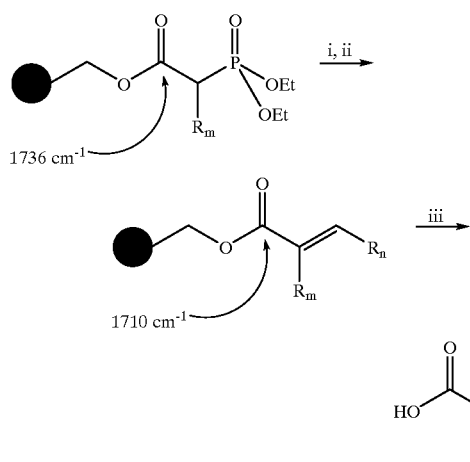

i) Lithium bis(trimethylsilyl)amide (4 equiv., 1.0 M in THF); THF, 1 hour, 25° C.
ii) Remove solvent; add $R_n$CHO (5 equiv., 0.5 M in 60% cyclohexane/THF); 2–3 days; 25° C.
iii) 30% trifluoroacetic acid/dichloromethane; 1 hour; 25° C.

The Parallel syntheses are accomplished using a Tecan Combitec organic synthesis robot. Forty eight reaction vessels are placed in the robot's reaction block and a slurry of ethyl phosphonate resin compound in THF is transferred by pipette into each of the reaction vessels. For this synthesis it is found to be more convenient to load the phosphonates to the resin on a large scale, then split the resin into the reaction block. The robot dispenses anhydrous THF to the reaction vessels, followed by the solution of base (1.0 molar in THF) as they sit on the deck of the robot in an ice bath. The sixteen aldehydes (see Table 1) are prepared as 0.5 molar solutions in 60% cyclohexane in THF. The reaction block is then manually moved to an orbital shaker and agitated for one hour at ambient temperature. The reaction block is then placed back on the instrument. The vessels are then drained, and solutions of the aldehydes are dispensed to their respective reaction vessels. The reaction block is then moved to an orbital shaker and agitated for 2–3 days at ambient temperature. Work-up of the reaction on the robot consists of draining the vessels and washing the resin with THF, 20% aqueous DMF, DMF, THF, and then dichloromethane. A total of 21 washes are needed to remove all the impurities in the resin matrix. The resin is then sampled for single bead FT IR analysis. The diagnostic carbonyl shift is a qualitative means of determining whether the reaction has gone to completion.

The anthranilic acid products are then cleaved from the resin using 30% trifluoroacetic acid (TFA) in dichloromethane. The TFA solutions are transferred to pre-tared test tubes contained in a Benchmate II[6] compatible 5×10 position rack, which had been defined on the deck of the robot. This format effectively couples sample concentration and weighing. Sample concentration is achieved using the Zymark Turbovap concentrator, in which the Benchmate II compatible rack fits, for efficient nitrogen blow-down of the samples. The Benchmate II compatible rack containing the desired samples is then placed in a Zymark Turbovap concentrator to remove the solvent (the Turbovap having been modified slightly by coating the manifolds with Teflon to prevent corrosion of the gas nozzles). The forty eight samples each containing approximately 3 mL of 30% TFA in dichloromethane are concentrated in about thirty minutes. The samples are usually chased with a one milliliter portion of methanol, then re-evaporated, to ensure complete removal of the TFA solution. The reaction set is then analyzed by $^1$H NMR and LC-MS (See Table 1).

TABLE 1

| Example | $R_m$ | IR Resin C=O Stretch | $R_n$ | Anthranilic Acid Purity (A % @ $UV_{220}$) |
|---|---|---|---|---|
| 70 | Et | 1733 | — | — |
| 71 | Ph(CH$_2$)$_3$— | 1733 | — | — |
| 72 | H | 1737 | — | — |
| 73 | Et | 1707 | A | 81 |
| 74 | Et | 1704 | B | 92 |
| 75 | Et | 1711 | C | 95 |
| 76 | Et | 1699 | D | 85 |
| 77 | Et | 1703 | E | 95 |
| 78 | Et | 1708 | F | 95 |
| 79 | Et | 1706 | G | 85 |
| 80 | Et | 1709 | H | 90 |
| 81 | Et | 1708 | I | 96 |
| 82 | Et | 1705 | J | 97 |
| 83 | Et | 1704 | K | 77 |
| 84 | Et | 1706 | L | 95 |
| 85 | Et | 1707 | M | 50 |
| 86 | Et | 1705 | N | 93 |
| 87 | Et | 1703 | O | 81 |
| 88 | Et | 1703 | P | 80 |
| 89 | Ph(CH$_2$)$_3$— | 1707 | A | 93 |
| 90 | Ph(CH$_2$)$_3$— | 1705 | B | 88 |
| 91 | Ph(CH$_2$)$_3$— | 1711 | C | 89 |
| 92 | Ph(CH$_2$)$_3$— | 1699 | D | 87 |
| 93 | Ph(CH$_2$)$_3$— | 1703 | E | 88 |
| 94 | Ph(CH$_2$)$_3$— | 1708 | F | 82 |
| 95 | Ph(CH$_2$)$_3$— | 1707 | G | 90 |
| 96 | Ph(CH$_2$)$_3$— | 1708 | H | 86 |
| 97 | Ph(CH$_2$)$_3$— | 1708 | I | 97 |
| 98 | Ph(CH$_2$)$_3$— | 1704 | J | 91 |
| 99 | Ph(CH$_2$)$_3$— | 1704 | K | 76 |
| 100 | Ph(CH$_2$)$_3$— | 1705 | L | 93 |
| 101 | Ph(CH$_2$)$_3$— | 1706 | M | 73 |
| 102 | Ph(CH$_2$)$_3$— | 1705 | N | 80 |
| 103 | Ph(CH$_2$)$_3$— | 1702 | O | 95 |
| 104 | Ph(CH$_2$)$_3$— | 1702 | P | 83 |
| 105 | H | 1712 | A | 76 |
| 106 | H | 1711 | B | 87 |
| 107 | H | 1717 | C | 93 |
| 108 | H | 1706 | D | 48 |
| 109 | H | 1708 | E | 90 |
| 110 | H | 1711 | F | 75 |
| 111 | H | 1708 | G | 50 |
| 112 | H | 1712 | H | 85 |
| 113 | H | 1714 | I | 70 |
| 114 | H | 1711 | J | 81 |
| 115 | H | 1708 | K | 90 |
| 116 | H | 1711 | L | 85 |
| 117 | H | 1711 | M | 74 |
| 118 | H | 1711 | N | 76 |
| 119 | H | 1711 | O | 75 |
| 120 | H | 1711 | P | 89 |

A = 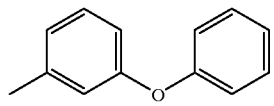

B = 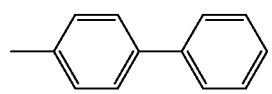

TABLE 1-continued

| Example | $R_m$ | IR Resin C=O Stretch | $R_n$ | Anthranilic Acid Purity (A % @ UV$_{220}$) |
|---|---|---|---|---|
| C = | | | (methylcyclohexyl) | |
| D = | | | (2,5-dimethylfuran) | |
| E = | | | (methylenedioxyphenyl, methylated) | |
| F = | | | (1-methylnaphthalene) | |
| G = | | | (4-methyl-N,N-dimethylnaphthalen-1-amine) | |
| H = | | | (3-bromotoluene) | |
| I = | | | (2,6-dimethylpyridine, methylated) | |
| J = | | | (5-methyl-2-(1-methyl-5-(trifluoromethyl)-1H-pyrazol-3-yl)thiophene) | |
| K = | | | (6-methoxy-2-methylnaphthalene) | |
| L = | | | (2-methylnaphthalene) | |
| M = | | | (3,5-dimethoxytoluene) | |
| N = | | | (4-tert-butyltoluene) | |
| O = | | | (4-(3-(dimethylamino)propoxy)toluene) | |
| P = | | | (4-heptyloxytoluene) | |

EXAMPLE 121

3-(3,4-Dimethoxybenzenesulfonyl)-5-methylhexanoic Acid Hydroxyamide

Step A: Wang resin (20 g, 15 mmol) is swelled in 300 mL of anhydrous DMF for 15 minutes. Then a solution of diethyl phosphonoacetic acid (8.83 g, 45 mmol) in 50 mL of DMF is added followed by pyridine (7.12 g, 90 mmol) and 2,6-dichlorobenzoyl chloride (9.4 g, 45 mmol). The mixture is agitated for 20 hours at room temperature. The resin is filtered and washed successively with DMF (3×), H$_2$O (3×), DMF (3×), THF (10×) and Et$_2$O (10×) followed by drying in vacuo at 40° C. for 20 hours. IR (micro) u C=O 1738 cm$^{-1}$.

Step B: The loaded resin from Step A (1 g, 0.75 mmol) is swelled in anhydrous THF (10 mL) for 15 minute followed by the addition of a 0.5 M solution of potassium bis(trimethylsilyl)amide in toluene (4 mL) at 0° C. The mixture is allowed to warm up to room temperature and is shaken for 30 minutes. The solvent is then drained to the top of the resin followed by the addition of anhydrous cyclohexane (10 mL) and isovaleraldehyde (0.17 g, 2 mmol). The mixture is shaken for approximately 72 hours and worked up as described in Step A. IR (micro) u C=O 1718 cm$^{-1}$.

Step C: To a solution of 3,4-dimethoxybenzenethiol (11.9 g, 70 mmol) in anhydrous THF (54.4 mL) at 0° C. is added a 2.5 M solution of n-butyllithium (5.6 mL, 14 mmol) and the solution is stirred at room temperature for 15 minutes.

The resin from Step B (0.25 g, 0.19 mmol) is swelled in anhydrous THF (2.5 mL) for 15 minutes and 4 mL of the above prepared 1 N thiol/thiolate stock solution is added. The mixture is shaken for approximately 100 hours and worked up as described in Step A. IR (micro) u C=O 1732 $cm^{-1}$.

Step D: The resin from step C (0.25 g, 0.19 mmol) is swelled in 1,4-dioxane (5 mL) for 15 minutes and a solution of m-chloroperoxybenzoic acid (0.44 g, 2.5 mmol) in 2 mL of 1,4-dioxane is added. The mixture is shaken for 16 hours and worked up as described in Step A.

Step E: The resin from Step D (0.25 g, 0.19 mmol) is treated with 1:1 dichloro-methane/trifluoroacetic acid (3 mL) for 1–2 hours. The resin is filtered and washed with dichloromethane (2×1 mL). The combined filtrates are concentrated in vacuo to provide 3-(3,4-dimethoxybenzenesulfonyl)-5-methylhexanoic acid (9.8 mg). $^1$H NMR (300 MHz, $CDCl_3$) δ 0.85 (d, 3H), 0.92 (d, 3H), 1.4 (m, 1H), 1.6–1.8 (m, 2H), 2.55 (dd, 1H), 2.9 (dd, 1H), 3.65 (m, 1H), 3.92 (s, 3H), 3.95 (s, 3H), 7.0 (d, 1H), 7.32 (s, 1H), 7.5 (d, 1H). MS (APCI; Loop) m/z 348 $(M+NH_4)^+$, 331 $(M+H)^+$.

Step F: The hydroxylamine bound Wang resin (50 mg, 0.037 mmol) is swelled in anhydrous DMF (1 mL) for 15 minutes followed by the addition of 1-(3-dimethyl-aminopropyl)-3-ethylcarbodiimide hydrochloride (30 mg, 0.16 mmol) and a solution of the carboxylic acid from Step E in 1 mL of anhydrous DMF. The mixture is shaken for 20 hours and worked up as described in Step A.

Step G: The resin from Step F is treated with 1:1 dichloromethane/trifluoroacetic acid (2 mL) for 1.5 hours. The resin is filtered and washed with dichloro-methane (2×1 mL). The combined filtrates are concentrated in vacuo to provide 3-(3,4-dimethoxybenzenesulfonyl)-5-methylhexanoic acid hydroxyamide (9.8 mg). MS (H-isp; LCMS) m/z 363 $(M+NH_4)^+$, 346 $(M+H)^+$.

EXAMPLES 122–147

The following hydroxamic compounds are synthesized using appropriate starting materials and following the steps of example 121:

EXAMPLE 122

5-(4-Butoxyphenyl)-3-(3,4-dimethoxybenzenesulfonyl)-pentanoic Acid Hydroxyamide

MS (APCI; LCMS) m/z 466 $(M+H)^+$.

EXAMPLE 123

3-(3,4-Dimethoxybenzenesulfonyl)hexanoic Acid Hydroxyamide

MS (H-isp; LCMS) m/z 332 $(M+H)^+$.

EXAMPLE 124

3-(3,4-Dimethoxybenzenesulfonyl)-4-methylpentanoic Acid Hydroxyamide

MS (H-isp; LCMS) m/z 332 $(M+H)^+$.

EXAMPLE 125

3-(3,4-Dimethoxybenzenesulfonyl)-5-methylhexanoic Acid Hydroxyamide

MS (H-isp; LCMS) m/z 346 $(M+H)^+$.

EXAMPLE 126

3-(3-Benzyloxyphenyl)-3-(3,4-dimethoxybenzenesulfonyl)-N-hydroxypropionamide

MS (H-isp; LCMS) m/z 472 $(M+H)^+$.

EXAMPLE 127

3-(2-Benzyloxyphenyl)-3-(3,4-dimethoxybenzenesulfonyl)-N-hydroxypropionamide

MS (APCI; LCMS) m/z 472 $(M+H)^+$.

EXAMPLE 128

3-(3-Benzyloxy-4-methoxyphenyl)-3-(3,4-dimethoxybenzenesulfonyl)-N-hydroxypropionamide MS (APCI; LCMS) m/z 502 $(M+H)^+$.

EXAMPLE 129

3-(3,4-Dimethoxybenzenesulfonyl)-N-hydroxy-3-(3-phenoxyphenyl)propionamide

MS (APCI; LCMS) m/z 458 $(M+H)^+$.

EXAMPLE 130

3-(3-(4-Chlorophenoxy)phenyl)-3-(3,4-dimethoxybenzenesulfonyl)-N-hydroxypropionamide MS (H-isp; LCMS) m/z 492 $(M+H)^+$.

EXAMPLE 131

3-(3,4-Dimethoxybenzenesulfonyl)-N-hydroxy-3-(3-(4-methoxy-phenoxy)phenyl)propionamide MS (H-isp; LCMS) m/z 488 $(M+H)^+$.

EXAMPLE 132

2-[Biphenyl-4-yl-(3,4-dimethoxybenzenesulfonyl)methyl]-4-methylpentanoic Acid Hydroxyamide via 2-[Biphenyl-4-yl-(3,4-dimethylbenzenesulfonyl)-methyl]-4-methylpentanoic Acid $^1$H NMR (300 MHz, $CDCl_3$) δ 0.9–1.1 (2xd, 6H), 1.6 (m, 1H), 1.9 (m, 1H), 2.35 (m, 1H), 3.55 (s, 3H), 3.7 (m, 1H), 3.9 (s, 3H), 4.3 (d, 1), 6.6–7.5 (series m, 12H). MS (APCI; LCMS) m/z 500 $(M+NH_4)^+$, 483 $(M+H)^+$ yields 2-[Biphenyl-4-yl-(3,4-dimethoxybenzenesulfonyl)methyl]-4-methylpentanoic acid hydroxyamide (4.9 mg). MS (APCI; LCMS) m/z 515 $(M+NH_4)^+$, 498 $(M+H)^+$.

EXAMPLE 133

2-[(3,4-Dimethoxybenzenesulfonyl)-(4-phenoxyphenyl)methyl]-N-hydroxy-4-(2-methoxyethoxy)butyramide MS (APCI; LCMS) m/z 560 $(M+H)^+$.

EXAMPLE 134

2-[(3,4-Dimethoxybenzenesulfonyl)-(4-phenoxyphenyl)methyl]-N-hydroxy-butyramide

MS (APCI; LCMS) m/z 486 $(M+H)^+$.

EXAMPLE 135

4-Benzenesulfonyl-2-[biphenyl-4-yl-(3,4-dimethoxybenzenesulfonyl)methyl]-N-hydroxybutyramide MS (isp; Loop) m/z 610 (M+H)+.

EXAMPLE 136

2-[Biphenyl-4-yl-(3,4-dimethoxybenzenesulfonyl)methyl]-N-hydroxy-4-phenyl-butyramide MS (APCI; LCMS) m/z 546 (M+H)+.

EXAMPLE 137

2-[Biphenyl-4-yl-(3,4-dimethoxybenzenesulfonyl)methyl]-N-hydroxy-4-(2-methoxy-ethoxy)-butyramide MS (isp; Loop) m/z 544 (M+H)+.

EXAMPLE 138

2-[Biphenyl-4-yl-(3,4-dimethoxybenzenesulfonyl)methyl]-N-hydroxybutyramide

MS (APCI; LCMS) m/z 470 (M+H)+.

EXAMPLE 139

2-[Biphenyl-4-yl-(3,4-dimethoxybenzenesulfonyl)methyl]-4-methylpentanoic Acid Hydroxyamide MS (APCI; LCMS) m/z 498 (M+H)+.

EXAMPLE 140

2-[Biphenyl-4-yl-(3,4-dimethoxybenzenesulfonyl)methyl]-N-hydroxy-3-methyl-butyramide MS (APCI; LCMS) m/z 484 (M+H)+.

EXAMPLE 141

2-[Biphenyl-4-yl-(3,4-dimethoxybenzenesulfonyl)methyl]-7-phenylheptanoic Acid Hydroxyamide MS (APCI; LCMS) m/z 588 (M+H)+.

EXAMPLE 142

2-[Biphenyl-4-yl-(3,4-dimethoxybenzenesulfonyl)methyl]-5-phenylpentanoic Acid Hydroxyamide MS (APCI; LCMS) m/z 560 (M+H)+.

EXAMPLE 143

2-[(3,4-Dimethoxybenzenesulfonyl)-(4-phenoxyphenyl)methyl]-N-hydroxy-3-methyl-butyramide MS (APCI; LCMS) m/z 500 (M+H)+.

EXAMPLE 144

2-[(3,4-Dimethoxybenzenesulfonyl)-(4-phenoxyphenyl)methyl]-7-phenylheptanoic Acid Hydroxyamide MS (APCI; LCMS) m/z 604 (M+H)+.

EXAMPLE 145

3-(3,4-Dimethoxybenzenesulfonyl)-2-ethylhexanoic Acid Hydroxyamide

Modified procedure for Step C: Reaction temperature=60° C., Reaction time=2×20 hours.

MS (APCI; LCMS) m/z 360 (M+H)+.

EXAMPLE 146

3-(3,4-Dimethoxybenzenesulfonyl)-2-(3-phenyl-propyl)hexanoic Acid Hydroxyamide

Modified procedure for Step C. Reaction temperature=60° C., Reaction time=2×20 hours.

MS (APCI; LCMS) m/z 450 (M+H)+.

EXAMPLE 147

2-[(3-Benzyloxyphenyl)-(3,4-dimethoxybenzenesulfonyl)methyl]-5-phenylpentanoic Acid Hydroxyamide Modified procedure for Step C. Reaction temperature=60° C., Reaction time=2×20 hours.

MS (APCI; Loop) m/z 590 (M+H)+.

EXAMPLES 148–161

Step A: The hydroxylamine bound Rink resin (0.1 g, 0.031 mmol) is swelled in anhydrous DMF (1 mL) for 15 minutes followed by the addition of 1-(3-dimethyl-aminopropyl)-3-ethylcarbodiimide hydrochloride (30 mg, 0.16 mmol) and a solution of the appropriate carboxylic acid prepared as in Example 73, Steps A–E in 1 mL of anhydrous DMF. The mixture is shaken for 20 hours and worked up as described in Example 73, Step A.

Step B: The resin from Step A (0.1 g, 0.031 mmol) is treated with 9:1 dichloromethane/trifluoroacetic acid (2 mL) for 1 hour. The resin is filtered and washed with dichloromethane (2×1 mL). The combined filtrates are concentrated in vacuo to provide the following hydroxamic acids:

EXAMPLE 148

N-[2-(3,4-Dimethoxybenzenesulfonyl)-3-hydroxycarbamoyl-propyl]-N Methyl-benzamide MS (APCI; Loop) m/z 437 (M+H)+.

EXAMPLE 149

N-[2-(3,4-Dimethoxybenzenesulfonyl)-3-hydroxycarbamoyl-butyl]-N Methyl-benzamide MS (APCI; Loop) m/z 451 (M+H)+.

EXAMPLE 150

Methyl-phenyl-carbamic Acid 3-(3,4-dimethoxybenzenesulfonyl)-4-hydroxycarbamoyl-butyl Ester MS (APCI; Loop) m/z 452 (M+H)+–15.

EXAMPLE 151

[3-(3,4-Dimethoxybenzenesulfonyl)-4-hydroxycarbamoyl-butyl]methyl-carbamic Acid Benzyl Ester MS (APCI; Loop) m/z 481 (M+H)+.

EXAMPLE 152

3-(3,4-Dimethoxybenzenesulfonyl)hexanedioic
Acid-1-hydroxyamide-6-(methyl-phenyl-amide)

MS (APCI; Loop) m/z 451 (M+H)+.

EXAMPLE 153

3-(3,4-Dimethoxybenzenesulfonyl)heptanedioic
Acid-1-hydroxyamide-7-(methyl-phenyl-amide)

MS (APCI; Loop) m/z 465 (M+H)+.

EXAMPLE 154

3-(3,4-Dimethoxybenzenesulfonyl)-6-(1,3-dioxo-1,
3-dihydro-isoindol-2-yl)hexanoic Acid
Hydroxyamide MS (APCI; Loop) m/z 477 (M+H)+.

EXAMPLE 155

7-(3,4-Dihydro-2H-quinolin-1-yl)-3-(3,4-
dimethoxybenzenesulfonyl)-7-oxo-heptanoic Acid
Hydroxyamide MS (APCI; Loop) m/z 491 (M+H)+.

EXAMPLE 156

7-(3,4-Dihydro-2H-quinolin-1-yl)-3-(3,4-
dimethoxybenzenesulfonyl)-6-oxo-hexanoic Acid
Hydroxyamide MS (APCI; Loop) m/z 477 (M+H)+.

EXAMPLE 157

7-Benzo(1,3)dioxol-5-yl-3-(3,4-
dimethoxybenzenesulfonyl)heptanoic Acid
Hydroxyamide MS (APCI; Loop) m/z 466 (M+H)+.

EXAMPLE 158

3-(3,4-Dimethoxybenzenesulfonyl)-3-(thien-3-yl)-N-
hydroxypropionamide

MS (APCI; Loop) m/z 372 (M+H)+.

EXAMPLE 159

3-(3,4-Dimethoxybenzenesulfonyl)-5-
phenylpentanoic Acid Hydroxyamide

MS (APCI; Loop) m/z 394 (M+H)+.

EXAMPLE 160

3-(3,4-Dimethoxybenzenesulfonyl)-5-(3-
phenoxyphenyl)pentanoic Acid Hydroxyamide MS (APCI; Loop) m/z 486 (M+H)+.

EXAMPLE 161

5-(4-Benzyloxyphenyl)-3-(3,4-
dimethoxybenzenesulfonyl)pentanoic Acid
Hydroxyamide MS (APCI; Loop) m/z 500 (M+H)+.

EXAMPLE 162

2-{(3,4-dimethoxybenzenesulfonyl)-[4-(4-
fluorobenzyloxy-phenyl]methyl}-4-methylpentanoic
Acid Hydroxyamide Step A: Wang resin (2 g, 1.5 mmol) is swelled in 20 mL of anhydrous DMF for 15 minutes. Then a solution of phosphonoacetic acid in DMF (1.13 g, 4.5 mmol) is added followed by pyridine (0.71 g, 9 mmol) and 2,6-dichlorobenzoyl chloride (0.94 g, 4.5 mmol). The mixture is agitated for 20 hours at room temperature. The resin is filtered and washed successively with DMF (3×), H$_2$O (3×), DMF (3×), THF (10×) and Et$_2$O (10×) followed by drying in vacuo at 40° C. for 20 hours. IR (micro) u C=O 1730 cm$^{-1}$.

Step B: The loaded resin from Step A (0.5 g, 0.375 mmol) is swelled in anhydrous THF (5 mL) for 15 minute followed by the addition of a 0.5 M solution of potassium bis (trimethylsilyl)amide in toluene (2 mL) at 0° C. The mixture is allowed to warm up to room temperature and is shaken for 30 minutes. The solvent is drained to the top of the resin followed by the addition of anhydrous cyclohexane(10 mL) and the aldehyde (0.25 g, 1 mmol). The mixture is shaken for approximately 72 hours and worked up as described in Step A. IR (micro) u C=O 1704 cm$^{-1}$.

Step C: To a solution of 3,4 dimethoxybenzenethiol(11.9 g, 70 mmol) in anhydrous THF (54.4 mL) at 0° C. is added a 2.5 M solution of n-butyllithium (5.6 mL, 14 mmol) and the solution is stirred at room temperature for 15 minutes.

The resin from step B (0.2 g, 0.15 mmol) is swelled in anhydrous THF (2.5 mL) for 15 minutes and 4 mL of the above prepared 1 N thiol/thiolate stock solution is added. The mixture is shaken for approximately 100 hours and worked up as described in step A. The thiol addition does not go to completion, as evidenced by IR spectra (u C=O 1703 cm$^{-1}$). The reaction is driven to completion by repeating the above procedure twice. IR (micro) u C=O 1731 cm$^{-1}$.

Step D: The resin from Step C (0.2 g, 9.15 mmol) is swelled in dioxane (5 mL) for 15 minutes and a solution of m-chloroperoxybenzoic acid (0.44 g, 2.5 mmol) in 2 mL of dioxane is added. The mixture is shaken for 16 hours and worked up as described in step A.

Step E: The resin from Step D (0.2 g, 0.15 mmol) is treated with 1:1 dichloro-methane/trifluoroacetic acid (3 mL) for 1–2 hours. The resin is filtered and washed with dichloromethane (2×1 mL). The combined filtrates are concentrated in vacuo to provide 2-{(3,4-dimethoxybenzenesulfonyl)-[4-(4-fluorobenzyloxyphenyl]methyl}-4-methylpentanoic acid (40 mg). $^1$H NMR (300 MHz, CDCl$_3$) δ 0.7–1.1 (2xd, 6H), 1.55 (m, 1H), 1.85 (m, 1H), 2.35 (m, 1H), 3.65 (s, 3H), 3.85 (s, 3H), 4.18 (d, 1H), 4.9 (s, 2H), 6.6–7.4 (series of m, 11H). MS (H-isp; Loop) m/z 548 (M+NH$_4$)+, 531 (M+H)+.

Step F: The hydroxylamine bound Rink resin (0.1 g, 0.031 mmol) is swelled in anhydrous DMF (1 mL) for 15 minutes followed by the addition of 1-(3-dimethylaminopropyl)-3-ethylcarbodiimide hydrochloride (20 mg, 0.1 mmol) and a solution of the carboxylic acid from step 5 in 1 mL of anhydrous DMF. The mixture is shaken for 20 hours and worked up as described in step A.

Step G: The resin from Step F (0.1 g, 0.031 mmol) is treated with 9:1 dichloro-methane/trifluoroacetic acid (2 mL) for 1 hour. The resin is filtered and washed with dichloromethane (2×1 mL). The combined filtrates are concentrated in vacuo to provide 2-{(3,4-dimethoxybenzenesulfonyl)-[4-(4-fluorobenzyloxy-phenyl] methyl}-4-methylpentanoic acid hydroxyamide (2.3 mg). MS (H-isp; LCMS) m/z 546 (M+H)+.

EXAMPLES 163–183

The following hydroxamic compounds are synthesized using appropriate starting materials and following the steps of Example 162:

EXAMPLE 163

3-(3,4-Dimethoxybenzenesulfonyl)-7-phenyl-2-(4-phenylbutyl)heptanoic Acid Hydroxyamide MS (APCI; LCMS) m/z 554 (M+H)+.

EXAMPLE 164

2-[1-(3-(3,4-Dimethoxybenzenesulfonyl)-5-phenylpentyl]-N 1-hydroxy-N 4-methyl-N 4-phenylsuccinamide MS (APCI; LCMS) m/z 568 (M)+.

EXAMPLE 165

3-(3,4-Dimethoxybenzenesulfonyl)-7-phenyl-2-(3-phenylpropyl)heptanoic Acid Hydroxyamide MS (APCI; LCMS) m/z 540 (M+H)+.

EXAMPLE 166

3-(3,4-Dimethoxybenzenesulfonyl)-2-isopropyl-7-phenylheptanoic Acid Hydroxyamide MS (APCI; LCMS) m/z 464 (M+H)+.

EXAMPLE 167

3-(3,4-Dimethoxybenzenesulfonyl)-2-isobutyl-7-phenylheptanoic Acid Hydroxyamide

MS (APCI; LCMS) m/z 478 (M+H)+.

EXAMPLE 168

3-(3,4-Dimethoxybenzenesulfonyl)-7-phenyl-2-propylheptanoic Acid Hydroxyamide

MS (APCI; LCMS) m/z 464 (M+H)+.

EXAMPLE 169

3-(3,4-Dimethoxybenzenesulfonyl)-7-phenyl-2-(4-phenyl-butyl)heptanoic Acid Hydroxyamide MS (APCI; LCMS) m/z 450 (M+H)+.

EXAMPLE 170

3-(3,4-Dimethoxybenzenesulfonyl)-2-[2-(2-methoxyethoxy)ethyl]-7-phenylheptanoic Acid Hydroxyamide MS (APCI; LCMS) m/z 524 (M+H)+.

EXAMPLE 171

3-(3,4-Dimethoxybenzenesulfonyl)-2-benzenesulfonylethyl-7-phenylheptanoic Acid Hydroxyamide MS (APCI; LCMS) m/z 590 (M+H)+.

EXAMPLE 172

3-(3,4-Dimethoxybenzenesulfonyl)-7-phenyl-2-(5-phenylpentyl)heptanoic Acid Hydroxyamide MS (APCI; LCMS) m/z 568 (M+H)+.

EXAMPLE 173

4-Benzenesulfonyl-2-{(3,4-dimethoxybenzenesulfonyl)-[4-(4-fluorobenzyloxy)phenyl]methyl}-N-hydroxy-butyramide MS (APCI; LCMS) m/z 658 (M+H)+.

EXAMPLE 174

2-{(3,4-Dimethoxybenzenesulfonyl)-[4-(4-fluorobenzyloxy)phenyl]methyl}-N-hydroxy-4-phenyl-butyramide MS (APCI; LCMS) m/z 594 (M+H)+.

EXAMPLE 175

2-{(3,4-Dimethoxybenzenesulfonyl)-[4-(4-fluorobenzyloxy)phenyl]methyl}-N-hydroxy-4-(2-methoxyethoxy)butyramide MS (APCI; LCMS) m/z 592 (M+H)+.

EXAMPLE 176

2-{(3,4-Dimethoxybenzenesulfonyl)-[4-(4-fluorobenzyloxy)phenyl]methyl}-N-hydroxy-butyramide MS (APCI; LCMS) m/z 518 (M+H)+.

EXAMPLE 177

2-{(3,4-Dimethoxybenzenesulfonyl)-[4-(4-fluorobenzyloxy)phenyl]methyl}-pentanoic Acid Hydroxyamide MS (APCI; LCMS) m/z 532 (M+H)+.

EXAMPLE 178

2-{(3,4-Dimethoxybenzenesulfonyl)-[4-(4-fluorobenzyloxy)phenyl]methyl}-4-methylpentanoic Acid Hydroxyamide MS (APCI; LCMS) m/z 546 (M+H)+.

EXAMPLE 179

2-{(3,4-Dimethoxybenzenesulfonyl)-[4-(4-fluorobenzyloxy)phenyl]methyl}-N-hydroxy-3-methylbutyramide MS (APCI; LCMS) m/z 532 (M+H)+.

EXAMPLE 180

2-{(3,4-Dimethoxybenzenesulfonyl)-[4-(4-fluorobenzyloxy)phenyl]methyl}-7-phenylheptanoic Acid Hydroxyamide MS (APCI; LCMS) m/z 636 (M+H)+.

EXAMPLE 181

2-{(3,4-Dimethoxybenzenesulfonyl)-[4-(4-fluorobenzyloxy)phenyl]methyl}-5-phenylpentanoic Acid Hydroxyamide MS (APCI; LCMS) m/z 608 (M+H)+.

EXAMPLE 182

2-{(3,4-Dimethoxybenzenesulfonyl)-[4-(4-fluorobenzyloxy)phenyl]methyl}-N 1-hydroxy-N 4-methyl 4-phenyl-succinimide MS (APCI; LCMS) m/z 637 (M+H)+.

EXAMPLE 183

2-{(3,4-Dimethoxybenzenesulfonyl)-[4-(4-fluorobenzyloxy)phenyl]methyl}-6-phenylhexanoic Acid Hydroxyamide MS (APCI; LCMS) m/z 622 (M+H)$^+$.

EXAMPLE 184

3-(4-Methoxybenzenesulfonyl)-3-(4-ethoxyphenyl)propionic Acid Hydroxyamide

Step A: Wang resin (20 g, 15 mmol) is swelled in 300 mL of anhydrous DMF for 15 minutes. Then a solution of diethyl phosphonoacetic acid (8.83 g, 45 mmol) in 50 mL of DMF is added followed by pyridine (7.12 g, 90 mmol) and 2,6-dichlorobenzoyl chloride (9.4 g, 45 mmol). The mixture is agitated for 20 hours at room temperature. The resin is filtered and washed successively with DMF (3×), H$_2$O (3×), DMF (3×), THF (10×) and Et$_2$O (10×) followed by drying in vacuo at 40° C. for 20 hours. (micro) u C=O 1738 cm$^{-1}$.

Step B: The loaded resin from Step A (1 g; 0.63 mmol) is swelled in anhydrous THF (10 mL) for 15 minute followed by the addition of a 1 M solution of lithium bis(trimethylsilyl)amide in THF (1.6 mL; 1.57 equiv.) at 0° C. The mixture is allowed to warm up to room temperature and is shaken for 30 minutes. The solvent is then drained to the top of the resin followed by the addition of anhydrous cyclohexane (10 mL) and 4-ethoxy-benzaldehyde (0.5 g; 3.3 mmol). The mixture is shaken for approximately 72 hours. The resin is then filtered and washed successively with DMF (3×), H$_2$O (3×), DMF (3×), THF (10×) and Et$_2$O (10×) followed by drying in vacuo at 40° C. for 20 hours. IR (micro) u C=O 1709 cm$^{-1}$.

Step C: To a solution of 4-methoxybenzene thiol (0.6 mL; 5 mmol) in anhydrous THF (1 mL) at 0° C. is added n-butyllithium (2.5 M in hexanes; 0.02 mL; 0.05 mmol) and the solution is stirred at room temperature for 15 minutes. The resin from step B (1 g; 0.63 mmol) contained in a polypropylene peptide synthesis cartridge is swelled in anhydrous THF (10 mL) for 15 minutes. The above-prepared 1 N thiol/thiolate stock solution is added. The mixture is shaken for approximately 100 hours. The resin is then filtered and washed successively with DMF (3×), H$_2$O (3×), DMF (3×), THF (10×) and Et$_2$O (10×) followed by drying in vacuo at 40° C. for 20 hours. IR (micro) u C=O1734 cm$^{-1}$.

Step D: The resin from Step C (1 g, 0.63 mmol) is swelled in 1,4-dioxane (5 mL) for 15 minutes and a solution of m-chloroperoxybenzoic acid (0.863 g; 5 mmol) in 2 mL of 1,4-dioxane is added. The mixture is shaken for 16 hours, the resin is then filtered and washed successively with DMF (3×), H$_2$O (3×), DMF (3×), THF (10×) and Et$_2$O (10×) followed by drying in vacuo at 40° C. for 20 hours.

Step E: The resin from Step D (1 g, 0.63 mmol) is treated with 1:1 dichloromethane/trifluoroacetic acid (8 mL) for 1–2 hours. The resin is filtered and washed with dichloromethane (2×1 mL). The combined filtrates are concentrated in vacuo to provide 3-(4-methoxybenzenesulfonyl)-3-(ethoxyphenyl)propionic acid (84 mg; 34%). $^1$H NMR (300 MHz, CDCl$_3$-d3) δ 1.42 (t, J=9.0 Hz, 3H); 3.08 (dd, J=10.8 Hz, 1H); 3.44 (dd, J=7.2 Hz, 1H); 3.86 (s, 3H); 4.02 (q, J=9.0 Hz, 2H); 4.54 (dd, J=7.1 Hz, 1H); 6.72 (d, J=12.6 Hz, 2H); 6.82 (d, J=12.3 Hz, 2H); 6.98 (d, J=12.4 Hz, 2H); 7.42 (d, J=12.3 Hz, 2H); 7.52 (bs, 1H). MS (H-isp; LCMS); m/z=387 [M+Na]$^+$, 382 [M+NH$_4$]$^+$, 365 [M+H]$^+$.

Step F: The hydroxylamine bound Rink resin (200 mg, 0.04 mmol) is swelled in anhydrous DMF (1 mL) for 15 minutes followed by the addition of 1-(3-dimethylaminopropyl)-3-ethylcarbodiimide hydrochloride (38 mg, 0.2 mmol) and a solution of the carboxylic acid from step 5 (84 mg; 0.2 mmol) in 1 mL of anhydrous DMF. The mixture is shaken for 20 hours. The resin is then filtered and washed successively with DMF (3×), H$_2$O (3×), DMF (3×), THF (10×) and Et$_2$O (10×) followed by drying in vacuo at 40° C. for 20 hours.

Step G: The resin from Step F (200 mg; 0.04 mmol) is treated with 1:1 dichloromethane/trifluoroacetic acid (3 mL) for 30 minutes. The resin is filtered and washed with dichloromethane (2×1 mL). The combined filtrates are concentrated in vacuo to provide 3-(4-methoxybenzenesulfonyl)-3-(4-ethoxyphenyl)propionic acid hydroxyamide (9.6 mg). MS (H-isp; LCMS); m/z=402 [M+Na]$^+$, 380 [M+H]$^+$.

EXAMPLES 185–189

The following hydroxamic compounds are synthesized using appropriate starting materials and following the steps of Example 184.

EXAMPLE 185

3-(4-Methoxybenzenesulfonyl)-3-(4-biphenyl)propionic Acid Hydroxy Amide) MS (H-isp; LCMS); m/z=412 [M+H]$^+$. A%=89% @220 nm.

EXAMPLE 186

3-(4-Methoxybenzenesulfonyl)-3-(4-phenoxyphenyl)propionic Acid Hydroxy Amide MS (H-isp; LCMS); m/z=428 [M+H]$^+$. A%=75% @220 nm.

EXAMPLE 187

3-(4-Methoxybenzenesulfonyl)-3-(4-benzyloxyphenyl)-propionic Acid Hydroxy Amide MS (H-isp; LCMS); m/z=442 [M+H]$^+$. A%=60% @220 nm.

EXAMPLE 188

3-(4-Methoxybenzenesulfonyl)-3-(4-fluorobenzyloxyphenyl)-propionic Acid Hydroxy Amide MS (H-isp; LCMS); m/z=460 [M+H]$^+$. A%=68% @220 nm.

EXAMPLE 189

3-(4-Methoxybenzenesulfonyl)-3-(4-(3-trifluoromethylphenoxy)-phenyl-propionic Acid Hydroxy Amide MS (H-isp; LCMS); m/z=496 [M+H]$^+$. A%=74% @220 nm.

The following examples are prepared using the process illustrated in Scheme 15:

EXAMPLE 190

N-benzyl-4-(methyl-O-methylhydroxylbenzylimine-O'-2'-bromobenzoxy)-phenoxymethyl-copoly(styrene-1% divinylbenzene)resin

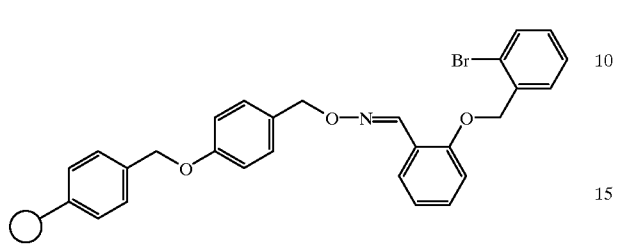

To a suspension of the hydroxylamine resin (0.5 g, 0.81 mmol, loading 1.62 mmol/g) in NMP (4 ml) and trimethylorthoformate (4 ml) is added 2-(2'-bromobenzoxy)benzaldehyde (0.71 g, 2.43 mmol) in NMP (4 ml). The suspension is agitated overnight. The mixture is filtered and washed with NMP (×3), THF (×3) and DCM (×3). The resin is dried in vacuo overnight.

EXAMPLE 191

N-(6,11-Dihydro-dibenzo[b,e]oxepin-11-yl)-hydroxylamine

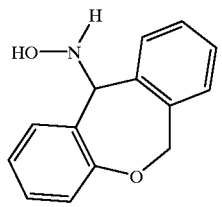

The resin (0.089 g, 100 μmol, loading 1.12 mmol/g) is swelled in dry benzene (2.5 ml) with gentle agitation for 15 minutes. To the suspension is added trihubyltin hydride (0.40 ml, 1.5 mmol) and AIBN (0.008 g, 5 μmol) and the solution is refluxed overnight. The mixture is cooled, filtered and washed with THF (×3), THF:H20 (3:1, ×3), MeOH (×3), THF (×3) and CH$_2$Cl$_2$ (×3). The resin is dried in vacuo overnight.

Trifluoroacetic acid (1 ml) and CH$_2$Cl$_2$(1 ml) are added and the mixture is shaken for 1 hour. The solution is filtered into a tared vial, the resin was washed with CH$_2$Cl$_2$(×3). The solvent is removed in vacuo to N-(6,11-Dihydro-dibenzo[b,e]oxepin-1-yl)-hydroxylamine (0.0256 g, quantitative). LCMS gives 227 [(M)$^+$, 100%].

EXAMPLE 192

N-benzyl-4-(methyl-O-methylhydroxylbenzylimine-O'-2'-bromo-2'-propenoxy)-phenoxymethyl-copoly(styrene-1% divinylbenzene)resin

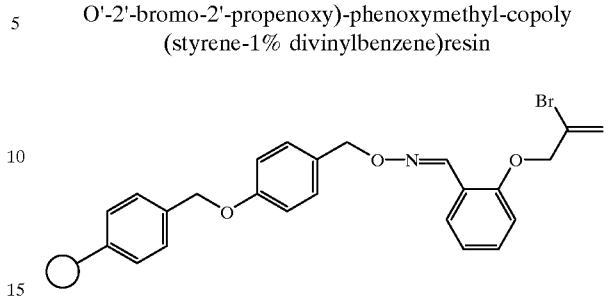

To a suspension of the hydroxylamine resin (1.0 g, 1.62 mmol, loading 1.62 mmol/g) in NMP (8 ml) and trimethylorthoformate (8 ml) is added 2-(2'-bromo-2'-propenoxy)benzaldehyde (1.17 g, 4.86 mmol) in NMP (8 ml). The suspension is agitated overnight. The mixture is filtered and washed with NMP (×3), THF (×3) and DCM (×3). The resin is dried in vacuo overnight.

EXAMPLE 193

N-(3-Methylene-chroman-4-yl)-hydroxylamine

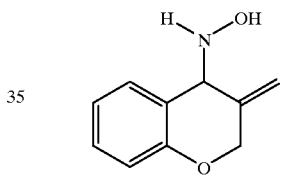

The resin (0.084 g, 100 μmol, loading 1.19 mmol/g) is swelled in dry benzene (2.5 ml) with gentle agitation for 15 minutes. To the suspension ias added tributyltin hydride (0.40 ml, 1.5 mmol) and AIBN (0.008 g, 5 μmol) and the solution is refluxed overnight. The mixture is cooled, filtered and washed with THF (×3), THF:H$_2$O (3:1, ×3), MeOH (×3), THF (×3) and CH$_2$Cl$_2$ (×3). The resin is dried in vacuo overnight. Trifluoroacetic acid (1 ml) and CH$_2$Cl$_2$(1 ml) were added and the mixture is shaken for 1 hour. The solution is filtered into a tared vial, the resin is washed with DCM (×3). The solvent is removed in vacuo to yield N-(3-Methylene-chroman-4-yl)-hydroxylamine (0.0115 g, 65%). LCMS gives 177 [(M)$^+$, 100%].

Scheme 15

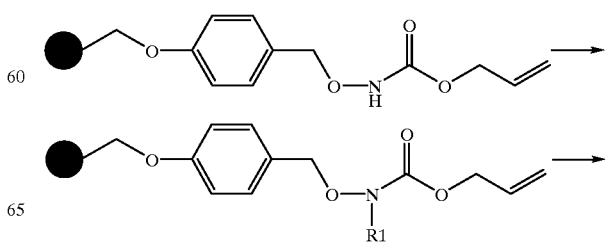

-continued

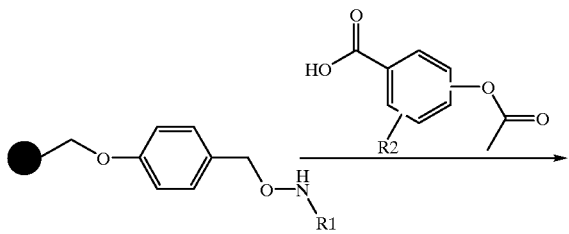

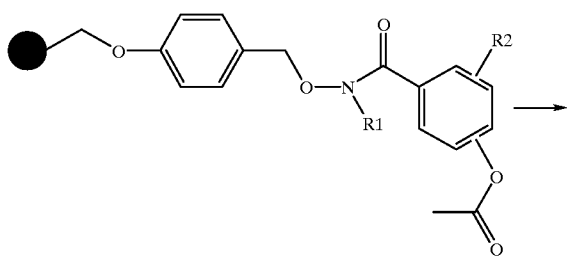

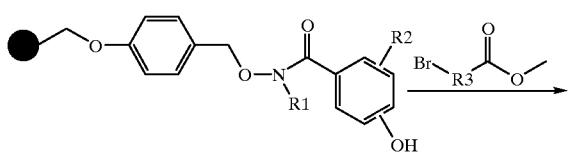

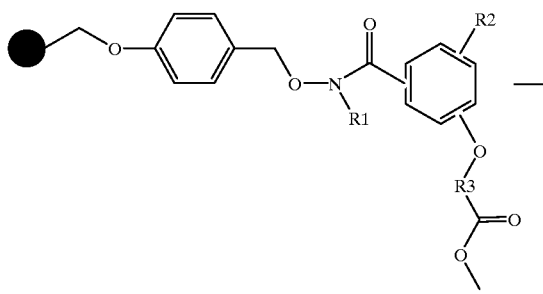

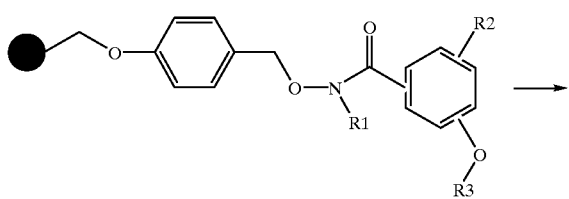

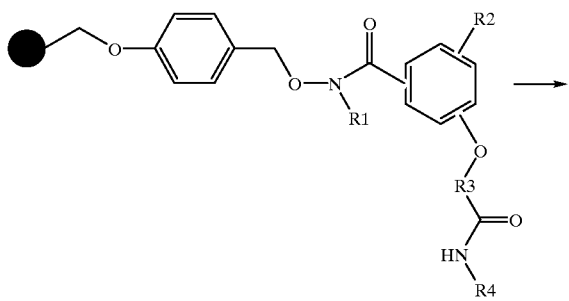

-continued

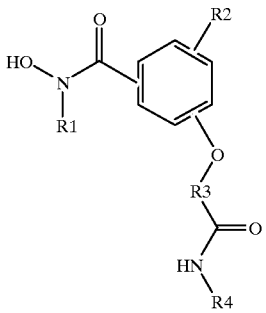

The following chemical library was produced according to Scheme 15.

The Library was produced utilizing the IRORI Accutag-10000 Combinatorial Chemistry system. The Library was generated in an 18×4×8×18 matrix.

EXPERIMENTAL

Procedures

Step 1: N-alkylation

The appropriate MicroKans (576 per reaction, 14.69 mmoles) are sorted into 1 L erlemyer flasks. Dry DMF (570 mL) is added. The Diazabicycloundecane (21.95 mL, 146.8 mmoles) is added. The reaction flasks are covered with aluminum foil and placed into an orbital shaker and agitated (100 rpm) for one hour at ambient temperature. At the end of this period, the appropriate alkyl halide (176.2 mmoles) and KI (cat., 2 grams) are added. The reaction flasks are placed back into the orbital shaking oven, which is now set to 60° C., and shaken (100 rpm) overnight at 60° C. At the end of this period, the reactions are allowed to cool to room temperature. The reaction mixture is drained. The reaction mixtures are washed individually in the following sequence: Wash with DMF, agitate for 10 minutes and drain (repeat 2×). Wash with MeOH, agitate for 10 minutes and drain. Wash with THF, agitate for 10 minutes and drain (repeat 1×). Wash with anhydrous DMF, agitate for 10 minutes and drain (repeat 1×).

After this washing protocol, more dry DMF (570 mL) is added. The Diazabicycloundecane (21.95 mL, 146.8 mmoles) is added. The reaction flasks are covered with aluminum foil and placed into an orbital shaker and agitated (100 rpm) for one hour at ambient temperature. At the end of this period, the appropriate alkyl halide (176.2 mmoles) and KI (cat., 2 grams) are added. The reaction flasks are placed back into the orbital shaking oven, which is now set to 60° C. the flasks are shaken (100 rpm) overnight at 60° C. At the end of this period, the reactions are allowed to cool to room temperature. The reaction mixture is drained. The reaction mixtures are washed individually in the following sequence: Wash with DMF, agitate for 10 minutes and drain (repeat 1×). Wash with MeOH, agitate for 10 minutes and drain. The MicroKans are randomly combined into two 10 L three neck round bottom flasks and washed in the following sequence: THF (2×5 l), and MeOH (5 l) & DCM, alternating (2×5l), Rinse with THF twice.

Step 2: Alloc Deprotection

The MicroKANS are randomly placed into two 12 L three neck round bottom flasks (approximately 5,184 per flask, 77.76 g of resin, 132.3 mmoles). The THF (2.5 l) and DMSO (2.5 l) are added. Each reaction flask is fitted with an overhead stirrer. Stirring is initiated. The morhpholine (288.2 mL; 3.30 mol), tetrakis(triphenylphosphine) palladium(0) (45.82 g; 0.039) and 0.5 N aqueous hydrochloric acid (158.6 mL; 0.5 N) are added in turn. After stirring for 14 hours, a small portion of resin is removed from one of the MicroKANs from each flask and checked by IR to confirm disappearance of the carbamate absorbance. Since both samples show disappearance of this diagnostic peak, the reactions are processed. The reaction solvent is drained. The reactions are washed individually according to the following procedure. Add DMF (5 l). Stir for approximately 20 min and drain. Repeat 2x. Add THF (5 l). Stir for approximately 20 min and drain. Add dichloromethane (5 l). Stir for approximately 20 min and drain. Add dichloromethane (5 l) followed by concentrated aqueous hydrochloric acid (25 ml). Stir for approximately 20 min and drain. Add a solution of 0.5% sodium diethyldithiocarbamate in DMF (5 l). Stir for approximately 20 min and drain. Add DMF (5 l). Stir for approximately 20 min and drain. Repeat 1x. Add MeOH (5 l). Stir for approximately 20 min and drain. Add THF (5 l). Stir for approximately 20 min and drain. Repeat 1x. Add MeOH (5 l). Stir for approximately 20 min. and drain. Add dichloromethane (5 l). Stir for approximately 20 min. and drain. Repeat 1x. Add diethylether (5 l). Stir for approximately 20 min. and drain. Repeat 1x. After the final washing the MicroKANs are dried by blowing a stream of nitrogen through the flask with intermittent agitation. After sufficient drying, the MicroKANs are sorted for the next reaction.

Step 3: Amide Bond Formation

The appropriate MicroKans (2592 per reaction, 66.10 mmoles) are sorted into 5 L 3-neck round bottom flasks. Dry DMF (2.5 L) is added. The reaction flasks are fitted with an overhead stirrer. The acetylsalicylic acid (119.1 g, 661 mmoles) is added and stirring initiated. After about 15 minutes, the EDCI (126.7 g, 661 mmoles) is added, and the reaction mixture is stirred for 60 hours. At the end of this period, the reaction mixture is drained. DMF (2.5 L) is added to the reaction flask. After stirring for 15 minutes, the reaction flasks are drained. This is repeated, and the Micro-Kans are randomly combined into two 12 l three neck round bottom flasks. The MicroKans are washed according to the following protocol. Add DMF (5 l). Stir for approximately 20 min and drain. Add MeOH (5 l). Stir for approximately 20 min and drain. Repeat 1x. Add THF (5 l). Stir for approximately 20 min and drain. Repeat 2x. Add MeOH (5 l). Stir for approximately 20 min. and drain. Repeat 1x. Add DMF (5 l). Stir for approximately 20 min and drain. Repeat 1x.

Step 4: Deacteylation

The above reaction flasks containing the Microkans are charged with a solution of 20% piperidine in DMF (5 L). After stirring for 15 hours, the reaction mixtures are drained and washed according to the following protocol. Add DMF (5 l). Stir for approximately 20 min and drain. Repeat 1x. Add THF (5 l). Stir for approximately 20 min and drain. Repeat 1x. Add MeOH (5 l). Stir for approximately 20 min and drain. Add dichloromethane (5 l). Stir for approximately 20 min. and drain. Add MeOH (5 l). Stir for approximately 20 min and drain. Add dichloromethane (5 l). Stir for approximately 20 min. and drain. Add diethylether (5 l). Stir for approximately 20 min. and drain. Repeat 1x. After the final washing the MicroKANs are dried by blowing a stream of nitrogen through the flask with intermittent agitation. After sufficient drying, the MicroKANs are sorted for the next reaction.

Step 5: Phenol Alkylation

The appropriate MicroKans (1296 per reaction, 33.05 mmoles) are sorted into 2 L Erlemyer flasks. Anhydrous DMF (1.2 L) and DBU (74.11 ml, 495,6 mmoles) are added. Hand swirl briefly. The reaction flasks are placed in the Shaker oven and agitated at RT for one hour. At the end of this period, the Cesium Carbonate (flasks 1–4, 6 and 8) and Potassium Carbonate (flasks 5 and 7) are added to the reaction flasks, which are yhrn hand swirled briefly. Then the appropriate halo-ester is added and the flask is hand swirled briefly, sfter which the flasks are replaced in the shaker oven. The oven is heated to 60° C., and the flasks are agitated for 15 hours. At the end of this period, the reactions are allowed to cool and then drained. They are washed individually according to the following protocol. Add DMF (1 l). Hand agitate briefly and drain. Repeat 2x. Add DMF:water (1 L, 1:1). Hand agitate briefly and drain. Add water (1 l). Hand agitate briefly and drain. Repeat 2x. Add DMF (1 l). Hand agitate briefly and drain. Add THF (1 l). Hand agitate briefly and drain. Repeat 1x. Add anhydrous DMF (1 l). Hand agitate briefly and drain. Repeat 1x.

After this washing protocol, more dry DMF (1.2 L) and DBU (74.11 ml, 495,6 mmoles) are added. The reaction flasks are hand swirled briefly and placed in the Shaker oven and agitated at room temperature for one hour. At the end of this period, the Cesium Carbonate (flask 1–4, 6 and 8) and Potassium Carbonate (flasks 5 and 7 y are added to the reaction flasks, which are then hand swirled briefly. The appropriate halo-ester is added and the flasks are hand swirled briefly, and then replaced in the shaker oven. The oven is heated to 60° C., and agitation is continued for 15 hours, at the end of which period the reaction flasks are allowed to cool and drained. They are washed individually according to the following protocol. Add DMF (1 l). Hand agitate briefly and drain. Repeat 2x. Add DMF:water (1 L, 1:1). Hand agitate briefly and drain. Repeat 1x. The Micro-Kans are randomly combined into two 10 L three neck round bottom flasks, and washed in the following sequence: Add DMF (5 l). Stir for approximately 20 min and drain. Add THF (5 l). Stir for approximately 20 min and drain. Repeat 1x. Add MeOH (5 l). Stir for approximately 20 min. and drain. Add dichloromethane (5 l). Stir for approximately 20 min. and drain. Add MeOH (5 l). Stir for approximately 20 min. and drain. Add dichloromethane (5 l). Stir for approximately 20 min. and drain. Add MeOH (5 l). Stir for approximately 20 min. and drain. Add diethylether (5 l). Stir for approximately 20 min. and drain. Repeat 1x. After the final washing, the MicroKANs are dried by blowing a stream of nitrogen through the flask with intermittent agitation. After sufficient drying, the MicroKANs are sorted for the next reaction.

Step 6: Ester Cleavage

The appropriate MicroKans (2448 per reaction, 62.42 mmoles) are sorted into four 5 L 3-neck round bottom flasks. Each flask is charged with THF (1.5 L). The methanol (0.75 L) is then added. The reaction flasks are fitted with an overhead stirring apparatus. After stirring for 10 minutes, the aqueous solution of lithium hydroxide (1.5 mol; 750 mL: 2.0 M) is added and stirring continued for 15 hours. At the end of this period, the reaction flasks are drained and washed individually according to the following protocol. Add THF (1.5 l). Stir for approximately 20 min and drain. Repeat 1x. Add MeOH (1.5 l). Stir for approximately 20 min. and drain.

Repeat 1x. Add DMF (1.5 l). Stir for approximately 20 min and drain. Repeat 1x. Add DMF:water (1.5 L, 1:1). Stir for approximately 20 min and drain. Repeat 1x. Add DMF (1.5 l). Stir for approximately 20 min and drain. Repeat 1x. Add THF (1.5 l). Stir for approximately 20 min and drain. Repeat 1x. Add dichloromethane (1.5 l). Stir for approximately 20 min. and drain. Add MeOH (1.5 l). Stir for approximately 20 min. and drain. Add dichloromethane (1.5 l). Stir for approximately 20 min. and drain. Add MeOH (1.5 l). Stir for approximately 20 min. and drain. Add dichloromethane (1.5 l). Stir for approximately 20 min. and drain. Add diethylether (1.5 l). Stir for approximately 20 min. and drain. Repeat 1x. After the final washing, the MicroKANs are dried by blowing a stream of nitrogen through the flask with intermittent agitation. After sufficient drying, the MicroKANs are sorted for the next reaction.

Step 7: Amide Bond Formation

The appropriate MicroKans (576 per reaction, 14.69 mmoles) are sorted into 2 L Erlenmeyer flasks. Dry DMF (570 mL) is added. The EDCI (28.16 g, 146.9 mmoles) is added and the flasks swirled by hand briefly. Then HOBt (19.85 g, 146.9 mmoles) is added and the flasks are swirled by hand briefly, followed by addition of the appropriate amine (132.2 mmoles). Then the flasks are hand swirled briefly, and replaced in the shaker oven, where they are agitated for 15 hours at room temperature. At the end of this period, the reaction flasks are drained and then washed individually according to the following protocol. Add DMF (500 ml). Hand agitate briefly and drain. Repeat 2x. Add methanol (500 ml). Hand agitate briefly and drain. Repeat 1x. The MicroKans are randomly combined into two 10 L three neck round bottom flasks and washed in the following sequence: Add THF (5 l). Stir for approximately 20 min and drain. Repeat 1x. Add MeOH (5 l). Stir for approximately 20 min. and drain. Add dichloromethane (5 l). Stir for approximately 20 min. and drain. Add MeOH (5 l). Stir for approximately 20 min. and drain. Add dichloromethane (5 l). Stir for approximately 20 min. and drain. Add MeOH (5 l). Stir for approximately 20 min. and drain. Add diethylether (5 l). Stir for approximately 20 min. and drain. Repeat 1x. After the final washing, the MicroKANs are dried by blowing a stream of nitrogen through the flask with intermittent agitation. After sufficient drying, the MicroKANs are sorted for the cleavage process.

Step 8. Cleavage

The MicroKANs are sorted into individual wells of IRORI AccuCleave 96 cleavage stations. Each well is charged with a TFA: dichloromethane mixture (1:1, 1200 mL). After agitating for approximately forty minutes, the reaction wells are drained into 2 mL microtubes in an 96-well format. The reaction wells are again charged with dichloromethane (600 mL). After manual agitation, this too is drained into the 2 mL microtubes in an 96-well format. The cleavage cocktail is removed in vacuo using a Savant Speedvac. The concentrated products from the cleavage mother plates are reconstituted with THF and transferred into two daughter plates utilizing a Packard MultiProbe liquid handler. The daughter plates are concentrated in vacuo utilizing a GeneVac centrifuge evaporator. Examples are listed below as follows:

| Structure | Mass Spec | % Purity (ELS) |
|---|---|---|
| 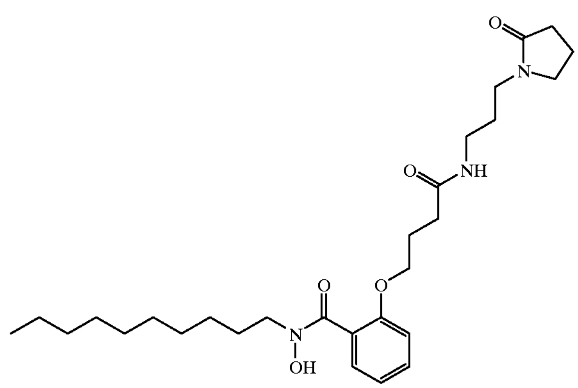 | 503.69 | 99.5 |
| 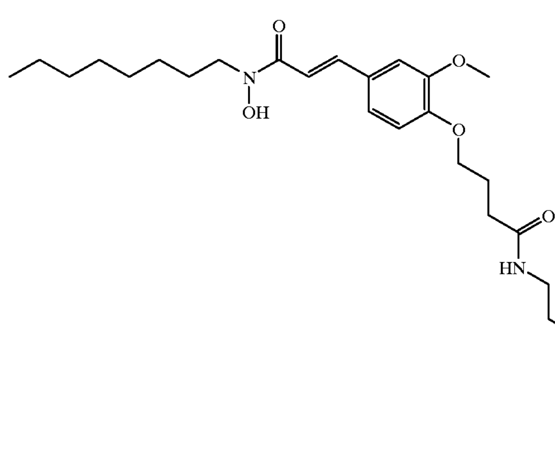 | 462.63 | 99.5 |

-continued

| Structure | Mass Spec | % Purity (ELS) |
|---|---|---|
| 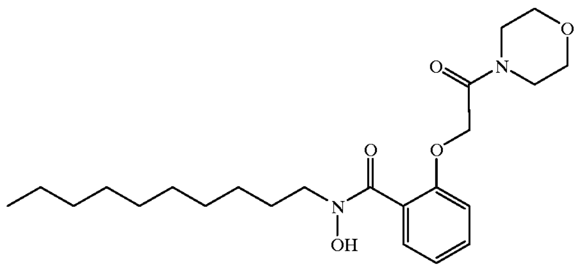 | 420.55 | 99.3 |
| 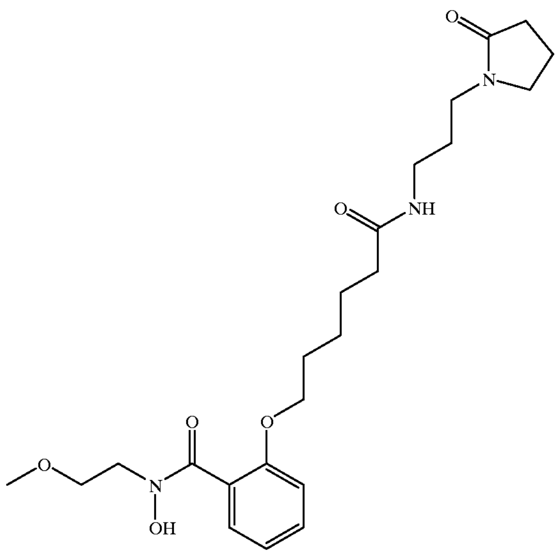 | 449.55 | 99 |
| 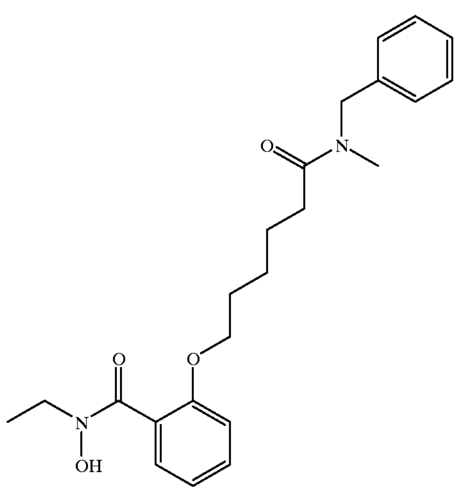 | 398.5 | 98.7 |

-continued

| Structure | Mass Spec | % Purity (ELS) |
|---|---|---|
| *(structure)* | 407.56 | 98.7 |
| *(structure)* | 323.39 | 98.3 |
| *(structure)* | 421.58 | 96.8 |
| *(structure)* | 522.69 | 95.1 |

-continued
| Structure | Mass Spec | % Purity (ELS) |
|---|---|---|
| 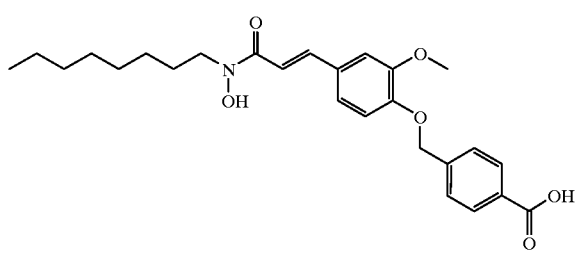 | 455.55 | 94.2 |
| 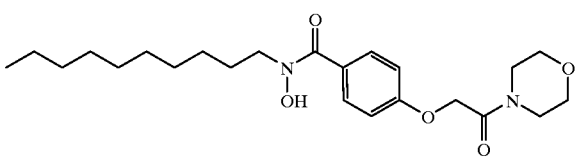 | 420.55 | 94.1 |
| 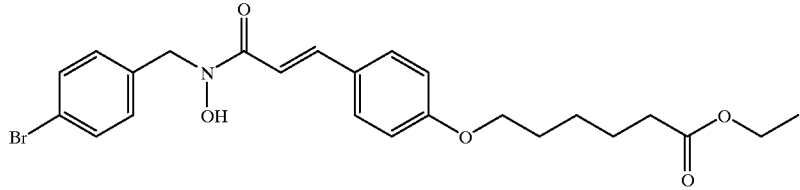 | 490.4 | 93.5 |
| 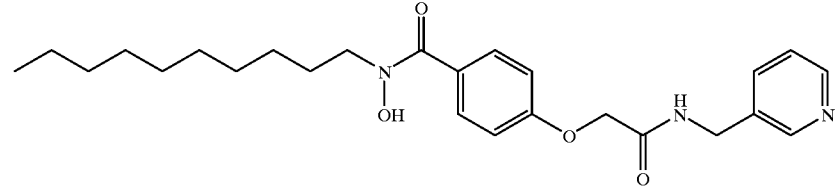 | 441.57 | 93.5 |
| 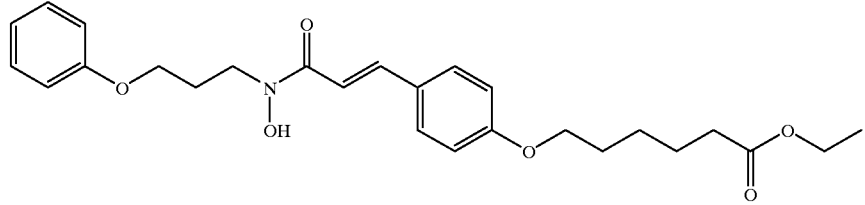 | 455.55 | 93.2 |
| 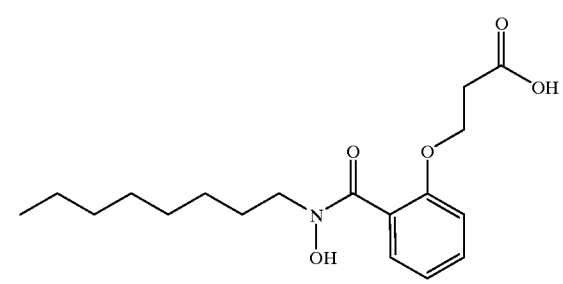 | 337.42 | 93.2 |

-continued

| Structure | Mass Spec | % Purity (ELS) |
|---|---|---|
| 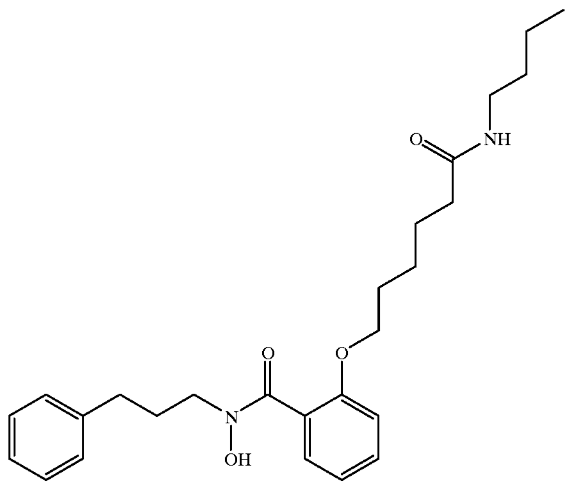 | 440.59 | 93.1 |
| 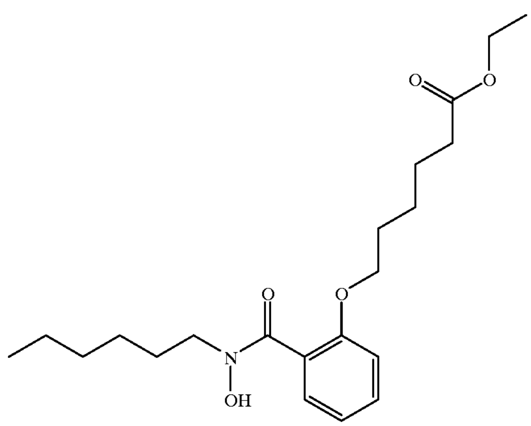 | 379.5 | 92.9 |
| 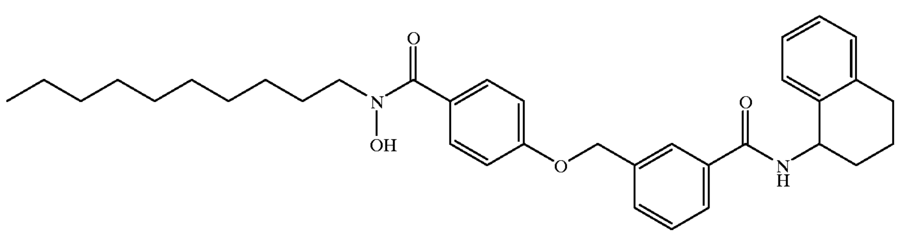 | 556.75 | 92.8 |

-continued

| Structure | Mass Spec | % Purity (ELS) |
|---|---|---|
| 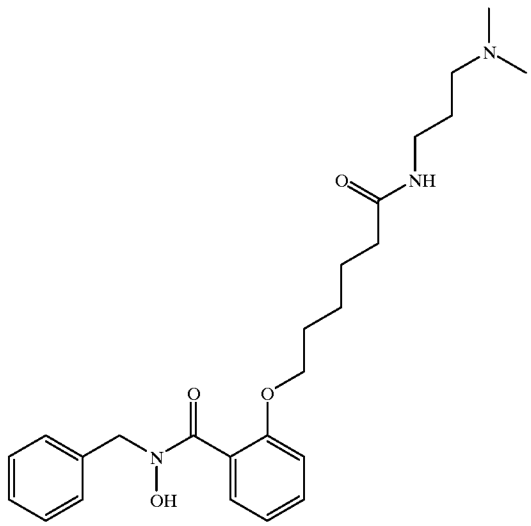 | 441.57 | 92.4 |
| 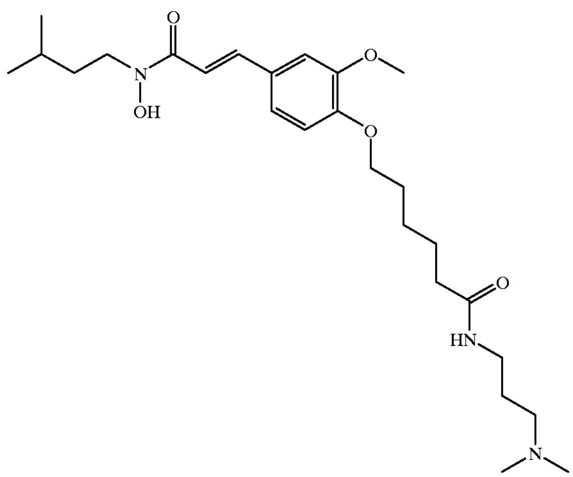 | 477.65 | 91.9 |
| 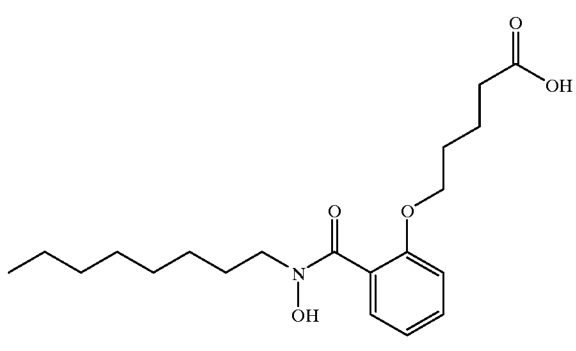 | 365.47 | 91.7 |
| 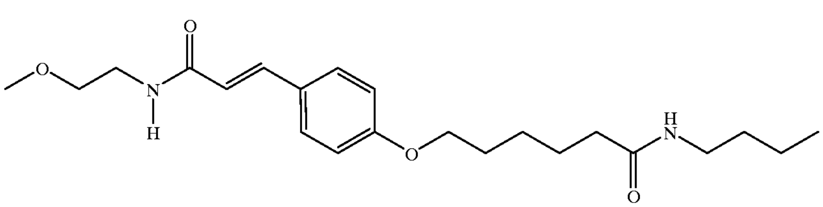 | 406.52 | 91.4 |

-continued
| Structure | Mass Spec | % Purity (ELS) |
|---|---|---|
| 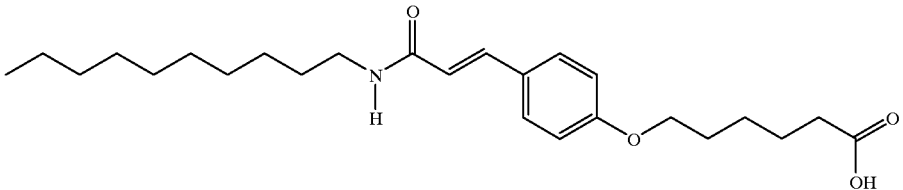 | 433.59 | 90.8 |
| 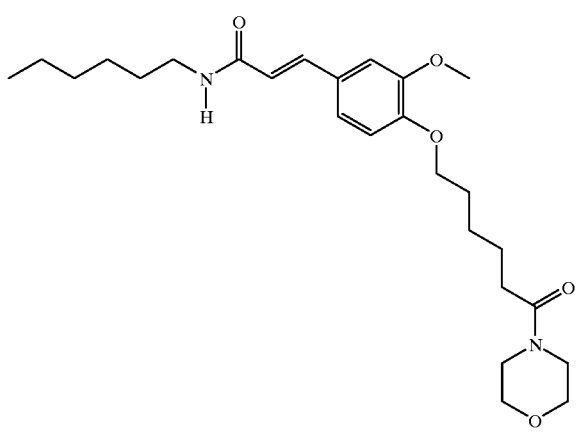 | 476.62 | 89.2 |
| 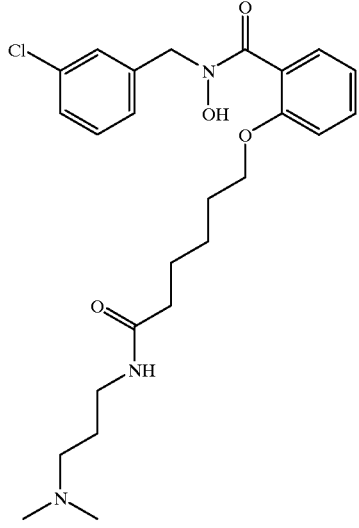 | 476.02 | 88.2 |

EDS

The energy dispersive x-ray measurements are made with an Electroscan Scanning Electron Microscope with an attached PGT digital detector. The beads are mounted on aluminum stubs and tested without a conductive coating. The net x-ray counts are reported after correction for the background. No corrections are made for atomic number, fluorescence or absorption.

What is claimed is:

1. A polymeric fluorophenyl hydroxylamine resin compound of formula

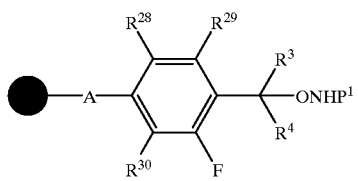

wherein

is a solid support;

A is absent or a group of formula —$X^1$—Z— wherein $X^1$ is —CHR— or —CHR—Y—CO—$(CH_2)_n$— wherein R is H, alkyl, phenyl, or phenyl substituted with —H, alkyl, alkoxy, halogen, nitrile or —$NO_2$, $R^{28}$, $R^{29}$, and $R^{30}$ are ring system substituents, or $R^{28}$ and $R^{29}$ taken together with the carbon atoms through which they are linked form a 6 membered aryl or a 5 to 6 membered heteroaryl, Y is —O— or —NH—, n is an integer from 1 to 6, and Z is —O— or —NH—;

$R^3$ and $R^4$ are independently —H, alkyl, phenyl, or phenyl substituted with one or more substituents selected from alkyl, alkoxy, halogen nitrile and —$NO_2$; and $P^1$ is H or an amine protecting group.

2. A polymeric fluorophenyl hydroxylamine resin compound according to claim 1 herein A is O—; and $R^{28}$, $R^{29}$, and $R^{30}$ are fluoro groups.

3. A polymeric fluorophenyl hydroxylamine resin compound according to claim 2 wherein one of $R^3$ and $R^4$ is H and the other is H or 2,4-dimethoxyphenyl.

4. A polymeric fluorophenyl hydroxylamine resin compound according to claim 3 wherein $P^1$ is H.

5. A polymeric fluorophenyl hydroxylamine resin compound according to claim 4 wherein $P^1$ is allyloxycarbonyl.

6. A polymeric fluorophenyl hydroxylamine resin compound according to claim 4 which is 4-(O-methylhydroxylamine)-2,3,5,6-tetrafluorophenoxymethyl-copoly(styrene-1% divinylbenzene)resin or 4-(2',4'-dimethoxyphenyl-O-methylhydroxylamine)-2,3,5,6-tetrafluorophenoxymethyl-copoly(styrene-1% divinylbenzene)resin.

* * * * *